United States Patent
Kalafut et al.

(10) Patent No.: US 10,957,442 B2
(45) Date of Patent: Mar. 23, 2021

(54) FACILITATING ARTIFICIAL INTELLIGENCE INTEGRATION INTO SYSTEMS USING A DISTRIBUTED LEARNING PLATFORM

(71) Applicant: GE Precision Healthcare LLC, Wauwatosa, WI (US)

(72) Inventors: John Kalafut, Pittsburgh, PA (US); Keith Dreyer, Fort Lauderdale, FL (US); Mark Michalski, Boston, MA (US); Stuart Pomerantz, Boston, MA (US); Sean Doyle, Boston, MA (US); Neil Tenenholtz, Cambridge, MA (US)

(73) Assignee: GE Precision Healthcare, LLC, Wauwatosa, WI (US)

( * ) Notice: Subject to any disclaimer, the term of this patent is extended or adjusted under 35 U.S.C. 154(b) by 101 days.

(21) Appl. No.: 16/237,525

(22) Filed: Dec. 31, 2018

(65) Prior Publication Data

US 2020/0211692 A1    Jul. 2, 2020

(51) Int. Cl.
*G16H 30/20*    (2018.01)
*G06N 20/00*    (2019.01)
(Continued)

(52) U.S. Cl.
CPC ............ *G16H 30/20* (2018.01); *G06F 40/30* (2020.01); *G06N 20/00* (2019.01); *G06T 7/0012* (2013.01); *G06T 11/60* (2013.01)

(58) Field of Classification Search
CPC ......... G16H 30/20; G06F 40/30; G06T 11/60; G06T 7/0012; G06N 20/00
See application file for complete search history.

(56) References Cited

U.S. PATENT DOCUMENTS 10,140,888 B2 *  11/2018  Campanatti, Jr. ...... G09B 23/28
10,593,035 B2 *   3/2020  Onal ..................... G06T 7/0012
(Continued)

FOREIGN PATENT DOCUMENTS

WO    2018236497 A1    12/2018

OTHER PUBLICATIONS

PCT/US2019/068877 filed Dec. 30, 2019—International Search Report—Written Opinion dated Mar. 26, 2020, 10 pages.

*Primary Examiner* — Wesley J Tucker
(74) *Attorney, Agent, or Firm* — Amin, Turocy & Watson, LLP

(57) ABSTRACT

Techniques are described that facilitate integrating artificial intelligence (AI) informatics in healthcare systems using a distributed learning platform. In one embodiment, a computer-implemented is provided that comprises interfacing, by a system operatively coupled to a processor, with a medical imaging application that provides for viewing medical image data. The method further comprises, facilitating, by the system, generation of structured diagnostic data according to a defined ontology in association with usage of the imaging application to perform a clinical evaluation of the medical image data. The method further comprises providing, by the system, the structured diagnostic data to one or more machine learning systems, wherein based on the providing, the one or more machine learning systems employ the structured diagnostic data as training data to generate or train one or more diagnostic models configured to provide artificial intelligence-based diagnostic evaluations of new medical image data.

20 Claims, 23 Drawing Sheets

(51) Int. Cl.
*G06F 40/30* (2020.01)
*G06T 7/00* (2017.01)
*G06T 11/60* (2006.01)

(56) References Cited

U.S. PATENT DOCUMENTS

| | | | |
|---|---|---|---|
| 2007/0081706 A1* | 4/2007 | Zhou | G16H 50/20 |
| | | | 382/128 |
| 2017/0076451 A1* | 3/2017 | Pauly | G06F 16/63 |
| 2019/0027252 A1* | 1/2019 | Calhoun | A61B 6/5217 |
| 2019/0066835 A1* | 2/2019 | Lyman | A61B 6/503 |
| 2019/0355483 A1* | 11/2019 | Smurro | H04L 65/1069 |
| 2020/0065940 A1* | 2/2020 | Tang | G06K 9/6256 |
| 2020/0160980 A1* | 5/2020 | Lyman | G06Q 20/14 |

* cited by examiner

LOCAL DEVICE DEPLOYMENT

FACILITATING ARTIFICIAL INTELLIGENCE INTEGRATION INTO SYSTEMS USING A DISTRIBUTED LEARNING PLATFORM

TECHNICAL FIELD

This application relates to computer-implemented techniques for integrating artificial intelligence informatics into various systems, including healthcare systems, using a distributed learning platform.

BACKGROUND

The healthcare industry has innumerable opportunities to leverage artificial intelligence (AI) and machine learning to achieve more accurate, proactive, and comprehensive patient care. AI offers a number of advantages over traditional analytics and clinical decision-making techniques. From reducing administrative burdens to supporting precision medicine, AI is showing promise across clinical, financial, and operational domains. Learning algorithms can become more precise and accurate as they interact with training data, allowing humans to gain unprecedented insights into diagnostics, care processes, treatment variability, and patient outcomes. However, even organizations with industry-leading analytics competencies in hand are facing complex challenges when it comes to applying AI to clinical care.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described herein that facilitate integrating AI informatics into healthcare systems using a distributed learning platform.

According to an embodiment, a system is provided that comprises a processor; and a memory that stores executable instructions that, when executed by the processor, facilitate performance of operations. These operations can comprise facilitating access by a plurality of disparate machine learning systems to a plurality of disparate healthcare systems and sources associated with disparate entities and that provide healthcare information regarding clinical and operational aspects of various healthcare domains. The operations further comprise, facilitating generation by the plurality of disparate machine learning systems, of a plurality of AI models configured to generate inferences regarding clinical and operational aspects of the various healthcare domains. The operations further comprise, facilitating storing of the AI models in a centralized, network accessible database, and facilitating application of relevant subsets of the respective models in association with performance of clinical and operational workflows of various healthcare organizations to generate the inferences.

In another embodiment, a system is provided that comprises a memory that stores computer executable components, and a processor that executes the computer executable components stored in the memory. The computer executable components can comprise an interface component that facilitates accessing a medical imaging application that provides for viewing medical image data. The computer executable components can further comprise a diagnostic data generation component that facilitates generating structured diagnostic data according to a defined ontology in association with viewing the medical image data using the imaging application. The computer executable component can further comprise a data collection component that provides the structured diagnostic data to one or more machine learning systems, wherein based on reception of the structured diagnostic data, the one or more machine learning systems employ the structured diagnostic data as training data to generate or train one or more diagnostic models configured to provide artificial intelligence-based diagnostic evaluations of new medical image data.

In another embodiment, a system is provided that comprises a processor; and a memory that stores executable instructions that, when executed by the processor, facilitate performance of operations. These operations can comprise accessing a centralized, network accessible healthcare model database comprising a plurality of AI models configured to generate inferences regarding clinical and operational aspects of various healthcare domains, wherein respective models of the plurality of AI models were developed by disparate machine learning systems. The operations further comprise identifying one or more models of the plurality of AI models that are relevant to medical image data of a patient selected for evaluating using a medical imaging visualization application, wherein the one or more models are configured to determine at least one of, feature information that identifies and characterizes one or more defined features reflected in the medical image data or diagnosis information regarding a medical condition reflected in the medical image data. The operations further comprise, applying the one or more models to the medical image data to generate at least one of, the feature information or the diagnosis information, and based on the applying, providing at least one of, the feature information or the diagnosis information to the medical imaging visualization application for rendering via the medical imaging visualization application.

In another embodiment, a system is provided that comprises a processor; and a memory that stores executable instructions that, when executed by the processor, facilitate performance of operations. These operations can comprise selecting one or more diagnostic models of the plurality of AI models that are relevant to medical image data of a patient selected for evaluating using a medical imaging visualization application. The operations further comprise applying the one or more diagnostic models to the image data to generate an interpretation of the medical image data, wherein the interpretation identifies and characterizes one or more features reflected in the medical image data or provides diagnosis information regarding a medical condition reflected in the medical image data. The operations further comprise providing the interpretation information representative of the interpretation via the medical imaging application and receiving feedback data regarding accuracy of the interpretation based on the providing. The operations further comprise generating structured training data that associates the image data with the interpretation information and the feedback data, and refining the one or more diagnostic models based on the structured training data using one or more machine learning techniques.

In some embodiments, elements described in connection with the disclosed systems can be embodied in different forms such as a computer-implemented method, a computer program product, or another form.

DETAILED DESCRIPTION

Figure 1:
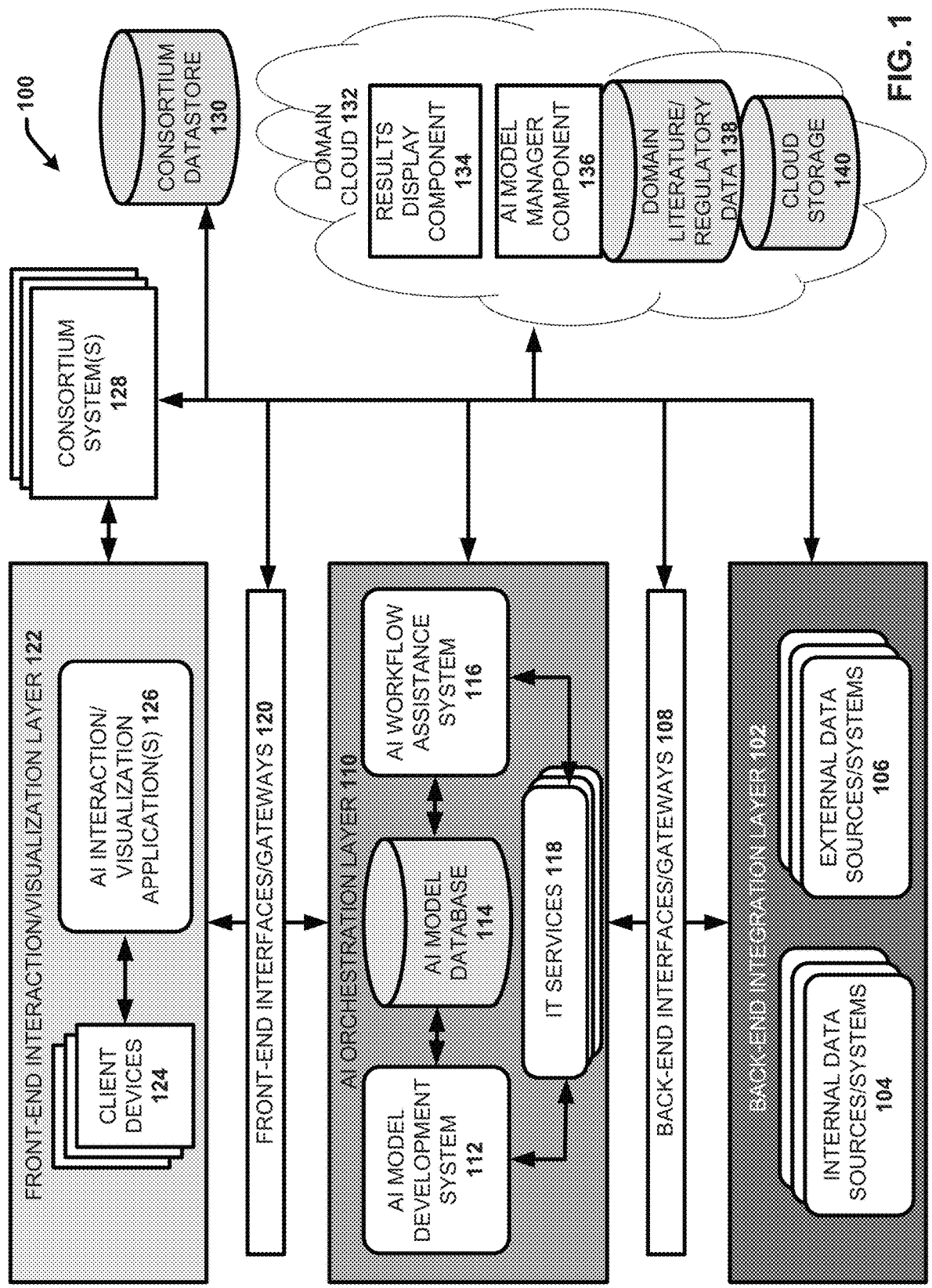
FIG. 1 illustrates a block diagram of an example, non-limiting system that facilitates integrating AI informatics into various systems using a distributed learning architecture, in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

The discloses subject matter is directed to techniques for integrating AI informatics into various systems, such as healthcare systems, using a distributed learning platform. For example, the application of machine learning methods and, more broadly, AI techniques, in the delivery of healthcare holds much promise to reduce waste, decrease costs and improve diagnostic and therapeutic accuracy and effectiveness. Diagnostic medicine is already served well by various analytical and numerical methods that can detect patterns, features and artifacts in signal and image-based data. The question is how to integrate it successfully into our healthcare systems. AI companies and health care providers face a range of obstacles on the path towards integration of new technologies into various domains of the healthcare field.

One of the greatest challenges is creating the infrastructure that can support that work. For the healthcare industry at large, there is currently no infrastructure for AI platforms. For example, data is the core of AI-driven health care. Though data is the foundation upon which machine learning technologies rely, the increasingly abundant amount of health care data remains highly dispersed in siloes or proprietary formats that make it difficult to combine with external sources. Imaging analytics is a good example of the complexity associated with using AI informatics tools used to evaluate medical image data. For example, AI can be used in medical imaging to automatically characterize features in images to make radiologists more efficient, minimize errors, and help them make their reports more quantitative and useful for the patients they serve. However, when trying to classify features in a computed tomography (CT) scan, for example, the imaging algorithm could need anywhere from hundreds to millions of images to learn consistent patterns and in all possible variants. Accordingly, integration of AI based imaging analytics alone requires a unique infrastructure that facilitates storing, accessing and processing such large data sets.

Not only are data access, storage and processing demands an issue, but interoperability between diverse systems involved in data storage, transfer, and processing is also a major factor in enabling AI integration into healthcare systems. For example, infrastructure shortcomings, such as an electronic health record (EHR) that doesn't lend itself to interoperability with model development systems can make it difficult to access the specific data elements required to develop and train AI models. This kind of fragmentation can be a significant problem for hospitals or health systems when implementing clinical AI decision support tools that aren't native to their current systems.

In addition to data storage, access and interoperability requirements, to develop models configured to provide AI based clinical solutions, the models must be trained and validated using mass amounts of accurately annotated training data. Machine learning algorithms can be categorized into two broad classes, supervised and unsupervised. Unsupervised learning methods have been investigated and researched the past few decades and, while encouraging, the maturity and robustness of these methods do not warrant themselves yet to the rigor needed for routine clinical practice. Supervised learning techniques, however, have been showing great promise due to computational and theoretical breakthroughs in the past five years. In a supervised paradigm, the learning system is first given examples of data by which human teachers or annotators apply classification labels to a corpus of data. The class labels are then used by the learning algorithm to adapt and change it's internal, mathematical representation (such as the behavior of artificial neural networks) of the data and mapping to some predication of classification etc. The training consists of iterative methods using numerical, optimization techniques that reduce the error between the desired class label and the algorithm's prediction. The newly trained model is then given new data as an input and, if trained well, can classify or otherwise provide assessment of novel data.

Because the supervised training paradigm is dependent upon rich and varied data, it is imperative that training data be accurate and represent most of the variants the algorithm could 'see' when new data is presented to it. For example, consider development of a diagnostic model configured to evaluate chest x-rays to classify them as normal versus abnormal. There could be hundreds of different variables that would make an x-ray abnormal. Thus, to train the diagnostic model, a corpus of data would be needed that shows all the possible representations of all those different variables compared to representations that would be classified as normal. That could add up to thousands or even millions of images, all of which would need to be labeled and annotated in a consistent manner.

Currently techniques for generating annotated training data for machine learning in healthcare informatics are inefficient, burdensome and prone to error. For example, to create the training data needed to generate accurate medical imaging diagnostic models, human experts must label the images and define which elements are normal and which should be flagged. In this regard, the mapping of image features based on the physics of the acquisition to underlying physiology, function and anatomy is the core of the science and art of diagnostic radiology, cardiology and pathology. Thus, to create sufficient training data for medical imaging-based diagnostics, human annotators must evaluate image data sets to detect and interpret a large variety of pathophysiology and artifacts in medical imagery and further accurately and consistently label the artifacts. The collection of data sets in a retrospective training setting by which a human expert sorts through and highlights and classifies findings on pre-selected exams can be extremely tedious, expensive and time-consuming. In addition, because it involves fallible and opinionated human experts defining what the algorithm will be looking for, it's also an opportunity for unconscious bias to creep in. Annotation is thus a considerable part of the challenge of creating machine learning algorithms in the healthcare field.

One or more embodiments of the disclosed subject matter are directed to systems, computer-implemented methods, apparatus and/or computer program products that facilitate integrating AI informatics into healthcare systems using a distributed learning platform or architecture. The distributed learning architecture can distribute and connect the various hardware and software components needed for developing healthcare-based AI models and applying the healthcare-based AI models in actual workflows by various healthcare systems. The distributed learning architecture can further facilitate a continuous cycle of self-sustained model optimization and expansion based on model validation feedback received in association with usage of the models in the actual workflows and the collaboration and sharing of diverse annotated and raw training data between disparate healthcare systems and services using one or more centralized health data consortiums.

In various embodiments, the distributed learning architecture can amass large datasets (labeled and unlabeled) from various disparate systems and data sources. In this regard, the distributed learning architecture can provide infrastructure solutions that allow seamless access to large volumes of data for teaching and training purposes to produce trustworthy results. In association with collating healthcare data from disparate data sources, the disclosed distributed learning architecture can facilitate interoperability between different systems, including back-end systems providing the data, front-end systems that facilitate viewing and interacting with the data, as well as AI orchestration systems responsible for processing the data to generate and train models and further integrate model application in actual clinical workflows to provide various AI based clinical decision support tools. In this regard, the distributed learning architecture can allow multiple users and clinical systems networked across regions and countries to share (labeled and unstructured) training data and developed models for reuse in multiple applications. The distributed learning architecture can apply anonymization methods are applied to the data for ensuring compliance with security and privacy regulations. One or more components of the distributed learning architecture can further be configured to identify relevant training data included in disparate data sources, parse it, retrieve it, cleanse it, and format it into standardized, structured machine-readable form so that it can be used for model creation.

In one or more embodiments, the distributed learning architecture can also provide techniques for systematically generating high quality annotated training data in clinical settings. In this regard, rather than retrospectively parsing through disparate databases to identify related sets of medical image data for training and further finding and correlating other relevant data associated with the respective images that can be used to facilitate pattern recognition and diagnostic conclusions (e.g., patient clinical history data, previously generated radiologist interpretive pathology reports from clinicians, etc.), and then providing this data to a third party annotation team to review, relate and and manually annotate the training data, the disclosed techniques integrate training data collation and generation into the clinical routine of practicing physicians. In this regard, one or more embodiments of the disclosed subject matter provide techniques and tools by which training data can be collected during the clinical routine of diagnostic physicians performing interpretation of signal and image-based medical data. In accordance with these embodiments, the distributed learning architecture can provide and/or interface with one or more medical imaging applications/systems that facilitate viewing and interacting with medical images in association with diagnostic reporting. For example, in some implementations, the medical imaging application can include an existing web application configured to provide medical imaging visualization and interaction services to clinicians.

In association with interfacing and/or providing access to the medical imaging application for diagnostic reporting, the disclosed techniques can provide various tools that allow clinicians (e.g., radiologists, etc.) interpreting the imaging data to annotate the data in the clinical execution of a diagnostic interpretation. For example, the disclosed techniques can allow for the physician to apply 'markups' on the images or signal artifacts by tagging features/defects of interest in the image data, defining dimensions of the features/defects, (e.g., areas, volumes depths, etc.), and adding descriptive annotation data (e.g., text data, symbols, etc.) to features of interest that further describe relevant characteristics of the features. The disclosed techniques can further restrict or control the terms/vocabulary and semantics that can be used to when annotating the images or signal artifacts, thereby enabling consistent generation of uniform structured data for training purposes. This is incredibly important to ensure ambiguity in training and teaching will be avoided. An additional benefit of this approach is the clarity of communication to clinical care teams that will also use these data in the treatment of a patient. The annotated image data (e.g., including markups and annotations) can be stored in a centralized training data database.

In some embodiments, in addition to annotating image data, the disclosed techniques can also facilitate generating and extracting semantically relevant terms from interpretive text reports generated by the clinicians in association with their evaluation of the medical image and signal data and/or other diagnostic data (e.g., laboratory data, medical notes based on patient evaluations, physiological feedback such as vital signs, and the like). These terms can also be associated with the respective images and/or the other diagnostic data in the training data database. In addition to generating and collating medical image data with markups and annotations, and relevant diagnostic report terms provided by clinicians via their diagnostic report, the disclosed techniques can further collect and collate, other relevant data related to the medical images at the time of interpretation, such as the raw image data (including waveforms), patient history data, laboratory data, physiological feedback data, and the like. The accumulated data can further be cleansed and organized and added to the one or more centralized training data databases for model development and training. The distributed learning architecture can further enable provision of the structured training data (markups, annotations and textual/report data) generated in association with the techniques described above to one or more machine learning systems for model development and training.

Although various embodiments of the disclosed systems are described in association with using AI informatics for diagnostic analysis of medical image data, it should be appreciated that the disclosed systems can be tailored to facilitate clinical decision support in many other clinical and operational healthcare domains to eliminate human error and inefficiency, improve patient quality of care and reduce waste, etc. In this regard, medical imaging is just one out of a thousand use cases in which the disclosed techniques for integrating AI informatics to facilitate making healthcare related decisions and evaluations can be applied. The disclosed distributed learning architecture can be used to share relevant training data, develop AI models and implement the AI models into clinical workflows of various healthcare disciplines in a manner that can at scale across departments, enterprises and regions. For example, in addition to facilitating clinical workflow optimization for radiologists, physicians and other clinicians involved with patient care, the disclosed distributed learning systems can provide for integrating AI informatics at the administrative level to facilitate planning, regulating, and managing medical services. For example, AI informatics can be integrated into patient scheduling and bed management systems to optimize population heath management. In another example, AI informatics can be used to identify areas of a healthcare system associated with waste and facilitate determining techniques for reducing costs and improving return on investment (ROI), or otherwise optimizing clinical and financial outcomes of patient care delivery. AI informatics can be integrated into healthcare billing systems to facilitate improving claim submission and reimbursement efficiency, to facilitate reducing fraud waste and abuse (FWA), and the like.

The disclosed distributed learning techniques can also be extended to various other industries or domains in addition to healthcare. For example, the disclosed distributed learning techniques can be extended to the marketing industry to automatically identify trends and deliver more personalized advertisements and products to consumers. In another example, the disclosed distributed learning techniques can be applied in the transportation industry to facilitate autonomous driving systems, to optimize airline and train scheduling and ROI in real-time based on anticipated delays, and the like. In another example, the disclosed distributed learning systems can provide various AI solutions to business organization to sift through huge data pools, process applications, spot anomalies, draw conclusions and make informed decisions, etc., to facilitate increasing service quality and efficiency while reducing cost. Other industries that can employ the disclosed distributed learning architecture to facilitate integrating AI informatics into their systems can include for example, educational systems, manufacturing systems, legal systems, personalized assistance systems, government regulatory systems, security systems, machine-to-machine (M2M) communication systems, agriculture systems, etc. The possibilities are endless.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a block diagram of an example, non-limiting system 100 that facilitates integrating AI informatics into systems of various domains using a distributed learning architecture, in accordance with one or more embodiments of the disclosed subject matter. Aspects of systems, apparatuses or processes explained in this disclosure can constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described.

In various embodiments, the distributed learning architecture of system 100 can include three interconnected layers including a back-end integration layer 102, an AI orchestration layer 110, and a front-end interaction/visualization layer 122. The back-end integration layer 102 can be coupled to the AI orchestration layer 110 via one or more back-end interfaces/gateways 108, and the front-end interaction/visualization layer 122 can be coupled to the AI orchestration layer via one or more front-end interfaces/gateways 120.

The back-end integration layer 102 can comprise various disparate data sources and systems that provide data and/or services associated with the industry/domain in which system 100 is applied to facilitate integrating AI informatics. For example, in implementations in which system 100 is applied to healthcare, the back-end integration layer 102 can comprise various disparate healthcare data sources and healthcare systems that provide healthcare data and/or services associated with generating or consuming the healthcare data. The back-end integration layer 102 can comprise one or more internal data sources/systems 104, as well as one or more external data sources/systems 106 that provide input data used that can be used for teaching and training one or more AI models directed domain/industry specific solutions.

For example, as applied to healthcare, the one or more internal data sources/systems 104, as well as one or more external data sources/systems 106 that provide input data that can be used for teaching and training one or more AI models to provide various healthcare solutions, referred to herein generally as healthcare AI models. In this regard, the one or more internal and/or external data sources/systems can include medical imaging systems configured to provide medical image data, patient records systems configured to provide patient health information, medical reporting systems configured to provide patient pathology reports, and the like. The back-end integration layer 102 can also comprise healthcare reporting/monitoring systems that provide real-time (or substantially real-time) contextual input information associated with patients, clinicians, and medical supplies/instruments at one or more healthcare facility (e.g., physiological information, location information, workflow information, etc.) that can be used as input when the healthcare models are run in association with performance of actual clinical and/or operational workflows in real-time to enhance performance of these workflows with AI oversight. Various embodiments, the data elements and training data included in the back-end integration layer 102 are searchable and can be accessed by multiple systems (investigators) for building new models and algorithms.

In the embodiment shown, internal data sources/systems 104 are distinguished from external data sources/systems 106 to indicate that the internal data sources/systems 104 can comprise one or more proprietary data sources/systems associated with a single enterprise. For example, although system 100 facilitates integration of disparate healthcare related enterprises, systems and data sources, in one or more implementations, system 100 can be described from the viewpoint of a single enterprises that utilizes, provides and/or manages system 100. For example, in some implementations, the single enterprise can be a health information technology (HIT) company (such as General Electric (GE) Healthcare Corporation) that provides a range of products and services that include medical imaging and information technologies, electronic medical records, medical diagnostics, patient monitoring systems, drug discovery, biopharmaceutical manufacturing technologies and the like. According to this example, the HIT company can also provide and/or enable one or more features and functionalities of system 100, in addition to the provision of their internal healthcare data for used in developing or training healthcare AI models. For example, in some implementations, the HIT system can provide one or more medical imaging visualization services that facilitate accessing, viewing and interacting with medical images (e.g., via a web-application, a local client-side application, a thin application, and the like). In another implementation, the single enterprise can comprise a hospital organization that provides medical services to patients via one or more hospitals, outpatient medical facilities, and the like. Regardless of the nature, operations and/or services provided by the enterprise, the internal data sources/systems 104 can comprise internal data sources/systems that are owned and/or operated by that enterprise. In this regard, the back-end integration layer 102 can amass various healthcare data sources and systems provided by different enterprises/entities at various locations around the world (and/or in the cloud) to enable access to all types of data that can be used as input to train and/or develop AI based healthcare informatics by the AI orchestration layer 110.

Figure 2:
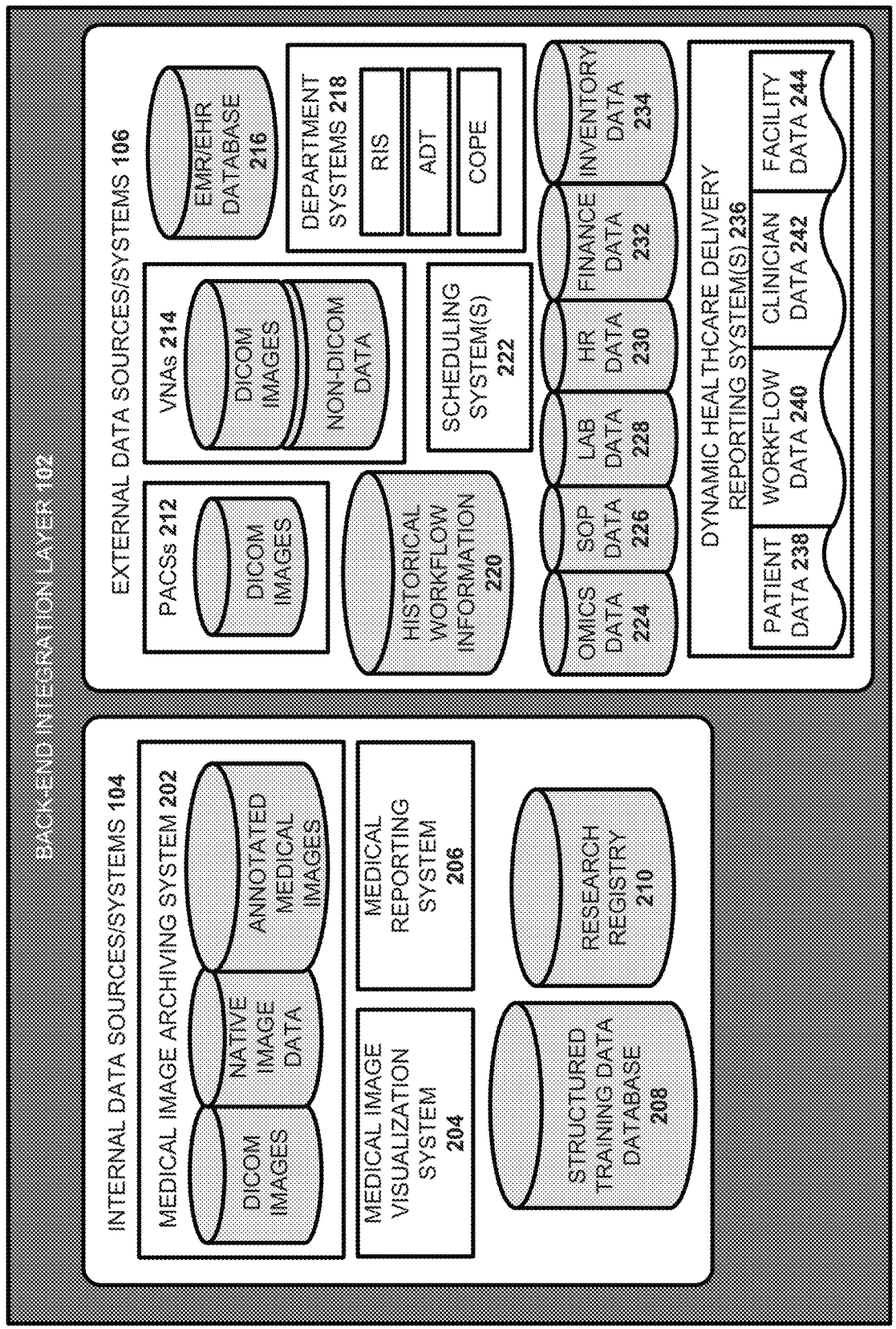
FIG. 2 illustrates a block diagram of an example, non-limiting back-end integration layer of a distributed learning architecture that facilitates integrating AI informatics in healthcare systems, in accordance with one or more embodiments of the disclosed subject matter.

FIG. 2 illustrates a more detailed representation of the back-end integration layer 102 in accordance with one or more embodiments of the disclosed subject matter as applied to healthcare system AI informatics integration. Repetitive description of like elements employed in respective embodiments is omitted for sake of brevity.

In the embodiment shown, the internal data sources/systems 104 can include (but are not limited to): a medical image archiving system 202, a medical image visualization system, a medical reporting system 206, a structured training data database 208, and a research registry 21. The medical image archiving system 202 can comprise a proprietary and/or proprietary archiving system for storing medical image data, including but not limited to: DICOM (digital imaging and communications in medicine) images, native medical image data, and annotated images. DICOM is the worldwide standard for handling, storing, printing, and transmitting information in medical imaging. It includes a file format definition and a network communications protocol. DICOM is used worldwide to store, exchange, and transmit medical images. For example, DICOM incorporates standards for the various imaging modalities such as radiography, ultrasonography, computed tomography, magnetic resonance, mammograph, and the like. DICOM includes protocols for image exchange (e.g., via portable media such as DVDs), image compression, 3D visualization, image presentation, and results reporting. Working with imaging data sets of size and complexity scales needed to develop sophisticated AI imaging diagnostic models can be somewhat easier than with other types of datasets due to the wide adoption of DICOM, a standard that has been in place for medical imaging for more than twenty years. For imaging, DICOM fills the role of connecting all the modalities in the hospital. The printers, displays, MRI machines, and other acquisition devices all communicate using DICOM standards.

As used herein, a native medical image or native medical image data refers to any image data captured by a medical imaging capture device or medical imaging acquisition device that is not necessarily formatted according to DICOM standards. For example, the medical imaging capture device can include but is not limited to: a conventional X-ray device, a digital radiography (DX) X-ray device, a X-ray angiography (XA) device, a panoramic X-ray (PX) device, computerized tomography (CT) device, a mammography (MG) device (including a tomosynthesis device), a magnetic resonance imaging (MRI) device, an ultrasound (US) imaging device, a color flow doppler (CD) device, a position emission tomography (PET) device, a single-photon emissions computed tomography (SPECT) device, a nuclear medicine (NM) imaging device, and the like. Native medical image data can comprise raw pixel data, waveform data, three-dimensional or depth data, point cloud data and the like. In various embodiments, the medical image archiving system 202 can correlate a DICOM image to one or more sets of native image data associated with the DICOM image. In some embodiments, the native image data can be employed by image visualization/processing systems to generate three-dimensional (3D) or reconstructed medical images.

Annotated images can include DICOM images and/or native images with some form of annotation or mark-up applied thereto. The annotation or mark-up can include graphical marks, tags, textual tags, text data, symbol data, audio data, and the like, applied to defined points, areas or volumes of interest in an image. For example, an annotated medical image can include an image of a patient's brain with a graphical mark defining the boundary of a tumor and including text or symbol data that classifies a grade or type of the tumor. In various embodiments, the annotated medical images can comprise annotated medical images generated using unique annotation tools described herein that can be integrated into an imaging visualization application used by physicians to view and evaluate medical images as part of their diagnostic routine. The features and functionalities of these annotation tools are described in greater detail infra with reference to FIG. 7.

In some implementations, the medical image archiving system 202 can comprise a picture archiving and communication system (PACS). A PACS provides economical storage and convenient access to images from multiple modalities (source machine types). Electronic images and reports can be transmitted digitally via a PACS, which eliminates the need to manually file, retrieve, or transport film jackets, the folders used to store and protect X-ray film. The universal format for PACS image storage and transfer is DICOM. Non-image data, such as scanned documents, may be incorporated using consumer industry standard formats like PDF (Portable Document Format), once encapsulated in DICOM. With these implementations, medical image archiving system 202 can include various imaging modalities (e.g., X-ray plain film (PF), CT, MRI, etc.).

The medical image visualization system 204 can include software and/or hardware components that facilitate accessing/retrieving images and/or image data included in the medical image archiving system 202, viewing or reviewing the image data, and/or interacting with the image data in association. In some implementations, the medical image visualization system 204 can provide the annotation tools for annotating medical images, as described infra with reference to FIG. 7. In some embodiments, one or more features and functionalities of the medical image visualization system 204 can be embodied as a web-based service (e.g., via a web-application, a thin-client application, a thick-client application, a hybrid application, etc.). In other embodiments, one or more features and functionalities of the medical image visualization system 204 can be embodied and/or provided at a client device as a local resident application. Although the medical image visualization system 204 is depicted as part of the back-end integration layer 102, one or more components and/or instances of the medical image visualization system 204 can be associated with the AI orchestration layer 110 and/or the front-end interaction/visualization layer 122.

In some embodiments, the medical image visualization system 204 can be configured to generate and/or provide reconstructed medical images. As used herein, reconstructed medical images refers to a computer generated medical image generated based on one or more native medical images. A reconstructed medical image generally refers to a 3D model or volumetric rendering (VR) generated based on several combined native medical images. For example, a 3D reconstructed medical image can include one or more meshes of triangles, quads, point clouds, and/or n-gons. A 3D reconstructed medical image can also include curved surfaces such as non-uniform rational basis splines (NURBS), which are a function of two parameters mapped to a common surface area in three-dimensional space. In some aspects, a 3D reconstructed medical image can have associated color, texture or material properties. The terms 3D image, 3D model, 3D reconstruction, 3D visualization, and 3D rendering are used herein interchangeably.

The medical reporting system 206 can comprise software and/or hardware components that facilitating generating medical reports for patients. For example, the medical reporting system 206 can provide tools that facilitate generating and/or collating clinical report data interpreted and/or provided by reporting clinicians in associating with their clinical/diagnostic workflows, including diagnostic workflows that involve evaluating and interpreting medical image data. In some implementations, the medical reporting system 206 can provide unique tools that facilitate generating structured training data from text (e.g., including speech to text) of medical reports provided by physicians in association with their clinical workflows, as described in greater detail infra with reference to FIG. 7. In some embodiments, one or more features and functionalities of the medical reporting system 206 can be embodied as a web-based service (e.g., via a web-application, a thin-client application, a thick-client application, a hybrid application, etc.). In other embodiments, one or more features and functionalities of the medical reporting system 206 can be embodied and/or provided at a client device as a local resident application. In this regard, although the medical reporting system 206 is depicted as part of the back-end integration layer 102, one or more components and/or instances of the medical reporting system 206 can be associated with the AI orchestration layer 110 and/or the front-end interaction/visualization layer 122.

The structured training data database 208 can comprise structured training data that has been annotated in accordance with a standardized format to facilitate efficient and consistent machine learning and AI model development based on the structured training data. For example, in some implementations, the structured training data can comprise collated annotated medical images, and medical terms/descriptions generated in accordance with the techniques described herein with reference to FIGS. 5 and 7. In this regard, the structured training data database 208 can collate medical image data, medical report data and the like that associates information identifying and defining key data points in the medical image data the medical report data using defined data structure, ontology, vocabulary for the respective types of data sets.

The research registry 210 can include information that indexes and organizes related data objects included in one or more internal data sources into data set cohorts. For example, the research registry can comprise information that identifies a set of images for a patient study, medical report data that interprets the images, patient information that identifies a patient ID associated with the data set, classification information that classifies one or more characteristics of the data set (e.g., negative chest x-ray), and the like. In this regard, the research registry can associate various types of metadata with distinct data sets that facilitates evaluating correlations between various types of data points associated within the respective data sets.

FIG. 2 further provides several examples of some external data sources/systems 106 that can provide useful healthcare related information for generating, training, applying and/or refining healthcare AI models in accordance with various embodiments described herein. In various embodiments, the external data sources/systems 106 can include one or more PACSs 212 of external healthcare systems. For example, many hospital organizations and healthcare IT companies can own and/or operate their own internal PACS. In this regard, the PACS of an external system can include DICOM images that were captured and/or stored for patients and/or clients of the external system. The external data sources/systems 106 can also include one or more a vendor neutral archive (VNA) systems. A VNA is a medical imaging technology in which images and documents (and potentially any file of clinical relevance) are stored (archived) in a standard format with a standard interface, such that they can be accessed in a vendor-neutral manner by other systems. In this regard, VNAs can collect and store images from multiple modalities and departments (e.g., radiology, cardiology, orthopedic, etc.) and pull everything into one big archive. In addition to DICOM images, VNAs can store data objects not directly related to images or DICOM data, such as human-generated requests and reports, health level 7 clinical document architecture (HL7-CDA) documents, and the like. The VNAs can also employ non-DICOM access protocols, such as Cross-Enterprise Document Sharing (XDS and XDS-I). VNAs can also provide cross-domain identity and code resolution (patient ID, accession number, procedure codes), dynamic DICOM tag morphing, and other adaptable features.

The external data sources/systems 106 can further include one or more electronic medical record and/or electronic health record databases 216 for one or more healthcare organizations, and various department systems 218. The various department systems 218 can include hospital healthcare IT systems that manage workflow and information flow for different departments, such as a radiology information system (RIS), a computerized physician order entry (CPOE) system, an admission, discharge and transfer system (ADT), and the like.

In some embodiments, the external data sources/systems 106 can also include one or more scheduling systems 222 of one or more departments for a healthcare organization, such as medical appointment scheduling systems employed by the healthcare facility to schedule and manage medical appointments. The appointment scheduling system can maintain information identifying scheduled appointments, including the patient scheduled, the time and date of the appointment, the medical clinician or department with which the appointment is scheduled, the location of the appointment, the type of the appointment, information regarding the purpose of the appointment, information regarding medical forms and things recommended or required for the patient to bring to the appointment or otherwise do to prepare for the appointment, and the like. In some embodiments, the appointment scheduling system can also track and update information regarding the progress of medical appointments, including information identifying whether a patient is checked into the medical appointment, whether the medical appointment is currently in progress, a current timeline of the medical appointment (e.g., tracking real-time duration of the medical appointment), whether the patient has check out of the medical appointment, and the like.

Some additional data external data sources that can be included in the back-end integration layer 102 can also include, omics data 224, standard operating procedure (SOP) data 226, laboratory (lab) data 228, human resources (HR) data 230, finance data 232, and inventory data 234.

The omics data 224 comprise genetic or omics information for patients. The genetic or omics information can include essentially any type of biological characteristic that could be attributed to a particular medical condition or disease. For example, the patient omics data 224 can include but is not limited to, DNA sequence data, gene expression data, microRNA (miRNA) expression data, copy number variation data, gene mutation data, DNA methylation data, reverse phase protein array (RPPA) data, and the like.

The SOP data 226 can include information defining workflows for various clinical procedures and scenarios of a healthcare organization, such as a hospital, an assisted living facility, and the like. For example, most medical organizations have defined rules or regulations that provide guidelines regarding how to treat patients in association with specific patient conditions, procedures and/or circumstances. These rules or regulations are generally referred to as standard operating procedures (SOPs). For example, emergency room physicians have SOPs for patients who are brought in an unconscious state; nurses in an operating theater have SOPs for the forceps and swabs that they hand over to the operating surgeons; and laboratory technicians have SOPs for handling, testing, and subsequently discarding body fluids obtained from patients. Medical procedures can also be associated with SOPs that provide guidelines that define how to perform the procedure (e.g., steps to perform and how to perform them), how to respond to different patient conditions in association with performance of the procedure, how to respond to complications that arise, and other type of events that may arise over the course of the procedure, and the like. Some healthcare organizations can also establish or adopt SOPs for medical conditions that can define standard medical practices for treating patient's having the medical condition and the respective medical conditions. Some healthcare organizations can also have SOPs regarding providing healthcare to patients having two or more medical conditions (e.g., referred to as comorbidity). In this regard, the SOP data 226 can include information that identifies and/or defines one or more standardized or defined protocols for following in association with performance of a procedure, treating a patient with a condition, and/or responding to a clinical scenario. For example, with respect to a procedure, the workflow information can identify procedural steps or processes to be performed and when, timing of the steps, information regarding how each step/process should be performed, and the like.

In some implementations, the SOP data 226 can include information defining workflow SOPs for a specific healthcare organization or facility. In other implementations, the SOP data 226 can include collated information that defines different workflow SOPs employed by different healthcare organizations as well as different facilities or departments within a single healthcare organization. For example, there is a popular misconception that SOPs are standardized across the universe of practice. However, the very nature of an SOP is that it is not universally applied. For example, the workflow SOPs for treating patient in labor at a small rural clinic may be different than that employed by a large training hospital. In some implementations, different AI healthcare workflow models can be developed that can evaluate workflow adherence to SOPs and/or to recommend appropriate workflow steps for performance in accordance with appropriate SOPs. With these implementations, the different AI healthcare evaluate workflow models can be directed to different SOPs for different environments and/or different healthcare organizations to facilitate determining appropriate aspects of the SOPs for applying to a clinical scenario based on the current context of the clinical scenario.

The lab data 228 can include information regarding laboratory studies results conducted for patients, including clinical laboratory results and laboratory report data that provides a form of diagnostic interpretation of the laboratory results. In various implementations, the lab data 228 can be received from and/or be associated with a laboratory information system (LIS). In some embodiments, a patient's lab data can be included with a patients EMR or EHR (e.g., in the EMR/EHR database 216).

The HR data 230 can include information about clinicians employed by one or more healthcare facilities. This can include information identifying the respective clinicians, their roles (e.g., including authorization to perform various tasks), their responsibilities, their specialties, their employment/work history, salary information, scheduling information, preference information and the like. The HR data 230 can also include learned information about the respective clinicians over time regarding the professional capabilities and performance. For example, the HR data 230 for a physician can include verified information developed for the physician over time the physician's accuracy and/or competency level in association with diagnosing specific types of patient conditions, reading medical images, reading specific types of medical images and/or medical images with certain characteristics, and the like. In this regard, in some implementations, when using information provided by a radiologist for example regarding an interpretation of a medical image for machine learning teaching/training, the value or weight applied to the accuracy of the interpretation can be based on the level of competency or accuracy of the clinician. For example, the accuracy of a particular diagnosis associated with an image or signal used for machine learning can be weighted based on the level of accuracy/competence of the physician providing the interpretation. In another example, the HR data 230 for a physician can include information developed for the physician over time that identifies historical performance of the physician in association with performance of one or more procedures. This can include for example, the number of procedures performed, the outcomes of the procedures, the areas of the workflow for the procedures that the clinicians perform well, number of errors made, types of errors made, where errors tend to be made and the like. The historical performance information can also include information regarding performance of a clinician in association with treating different medical conditions. In this regard, the historical performance information can identify the level of expertise and proficiency of a clinician with respect to treating different types of conditions and performing different types of procedures. The HR data 230 can also include feedback provided by patients, colleagues and the like regarding a clinician's performance, including the level of quality and satisfaction the respective individuals associate with the clinician's performance. In some implementations, the HR data 230 can also include information regarding preferences regarding one or more other clinicians a clinician prefers to work with, one or more other clinicians the clinician does not work well with (e.g., associated with one or more negative outcomes in performance or patient satisfaction), and the like.

The finance data 232 can include any type of financial information pertaining to costs associated healthcare services and/or operations of a healthcare facility. For example, the finance data 232 can include costs associated with different procedures and utilization of different resources, including human resources as well as medical instruments and supplies. In some implementations, the finance data 232 can include historical costs, such as historical costs associated with past procedures, courses of care and the like. For example, with respect to past procedures, the finance data 232 can identify total costs (e.g., to the healthcare organization) of each procedure performed, as well as line item costs associated with individual components of the procedures, including supplies/equipment costs, personnel costs, room/space costs, individual process or procedural steps, and the like. In some implementations, finance data 232 can also include information regarding reimbursement for respective procedures, including total reimbursement and reimbursement for procedural components. In some implementations, the finance data 232 can also include cost information attributed to LOS, procedure complications, and procedural and/or clinical errors (e.g., including cost attributed to litigation associated with the error).

The inventory data 234 can include information regarding medical supplies, instruments, equipment and the like that are used by a healthcare organization in association with performance of medical procedures. In this regard, the inventory information can identify all medical supplies, instruments, equipment that are in stock or otherwise in possession by the medical organization, their status (e.g., used/unused, current/expired, working/broken, etc.), what they are used for, where they are located and the like. The inventory data 234 can also include records of when respective medical supplies, instruments, equipment, etc. were ordered, what they were ordered for (e.g., a specific procedure, a specific clinician, a specific medical department, a specific operating room, etc.), and where the supplies came from. The inventory data 234 can also include same or similar information for supplies that are out of stock, ordered, and to be ordered.

In some embodiments, the external data sources/systems 106 can include one or more dynamic healthcare delivery reporting systems 236 configured to provide real-time (or substantially real-time) contextual information associated with a current state of a healthcare facility, including patient data 238, workflow data 240, clinician data 242 and facility data 244, for example. The information provided by the dynamic healthcare delivery reporting systems 236 can be considered dynamic because at least some of the information can dynamically change over a course of patient care. For example, at least some of the information can change from second to second, minute to minute, over a course of an hour, over a course of a day, and the like.

The patient data 238 can include real-time information related to a patient's current physiological state or condition. For example, in some implementations, the patient data 238 can include information received in association with initiation of treatment of a patient that provides an assessment of a condition or diagnosis of a patient for which medical care is being provided to the patient. The patient data 238 can further include any information gathered over the course of care relating to the physiological state or condition of the patient. For example, the patient data 238 can include information regarding tracked physiological parameters of a patient (e.g., vital signs and various other physiological parameters), timing associated with the tracked physiological parameters (e.g., onset, duration, etc.), changes in a physiological status or state of a patient, changes in appearance of the patient, physical range of motion or movements capable of being performed by the patient, expressed symptoms and side effects of the patient, expressed levels of pain experienced by the patient, information regarding a mental state of the patient, and the like. For example, for labor patients, there are key data and decision points that can affect the outcome of the baby including lifelong cognitive and physical functions. For instance, these key data points can include but are not limited to: timing of onset of labor, timing of decision to induce, timing of the active phase, timing of rupture of the membrane, timing and dosage of certain administered pharmaceuticals, changes in dilation, fetal heart rate, fetal deceleration, maternal temperature, maternal hypertension, timing of hypoxia onset, and the like. According to this example, for labor patients, the patient data 238 can include information corresponding to or related to these key data point. In some implementations, the patient data can also identify a current location of a patient relative to a healthcare facility (e.g., in an ambulance on the way to the emergency room, within a room of the healthcare facility, etc.). In some embodiments, the specific physiological parameters that are tracked can be predefined based on a condition or the patient or course of care for the patient. For example, the physiological data that is relevant to a patient undergoing a course of labor can be different to those of a patient receiving a heart transplant. Accordingly, the specific patient data that is collected and reported in real-time can be tailored to the specific context of a patient's condition and treatment.

The types of dynamic healthcare delivery reporting systems 236 from which the patient data 238 is received can vary. In some implementations, the patient data 238 can be received directly from one or more medical monitoring devices associated with the patient (e.g., mother and infant(s) in for labor patients) and configured to read and report monitored physiological parameters. For example, the medical monitoring devices can include a device worn by, within (e.g., an implantable medical device (IMD), and/or physically connected to the patient and configured to capture and/or monitor physiological information (e.g., physiological parameters) that can be sent to or otherwise received in real-time or substantially real-time. For example, these physiological parameters can include but are not limited to information regarding: heart rate, blood pressure, SpO2, respiratory rate, temperature, hypertension, hydration level, glucose level, cortisol level, potassium level, etc. In another example, the patient data 238 can be provided by one or more medical monitoring devices configured to detect presence of various bacteria, viruses, pathogens, presence and/or levels of various biomarkers and/or known substances produced by the body. Other potential information that can be detected by medical monitoring devices can include but is not limited information regarding a patient's folic acid, calcium, magnesium, creatine kinase, vitamin B12, vitamin D, ferritin, total cholesterol, hemoglobin, HDL, LDL, triglycerides, fatty acids, insulin, hemoglobin, hormones (e.g. thyroid hormones (thyroid-stimulating hormone (TSH), metabolic hormones, reproductive hormones, etc.), liver enzymes, electrolytes (e.g. sodium, potassium, chloride, etc.), platelets, white blood cells, red blood cells, iron, etc.

For example, in some embodiments, the dynamic healthcare delivery reporting systems 236 can include blood-sampling sensors (e.g. as glucose meters), tissue-embedded sensors (e.g. pacemakers and defibrillators), ingestibles embedded in pills that dissolve, epidermal sensors (e.g. patches and digital tattoos), wearables embedded in clothing or accessories, and external sensors (e.g. blood-pressure cuffs and pulse oximeters). In another example, the dynamic healthcare delivery reporting systems 236 can include bio-sensing contact lenses configured to be worn in the patient's eye and sense/detect various biomarkers in tear fluid. In another example, the dynamic healthcare delivery reporting systems 236 can include an implantable cardioverter-defibrillator (ICD) that is implanted within the patient and configured to perform conventional functions of an ICD as well as additional sensing of biomarkers in bodily fluids. In yet another example, the dynamic healthcare delivery reporting systems 236 can include a urinary catheter configured to be worn by the user to facilitate urinary functions while also being configured to detect biomarkers in urine. In another example, the dynamic healthcare delivery reporting systems 236 can include a device configured to determine physiological information about the user based on detection of one or more biomarkers included in sweat generated by the patient. In yet another example, the dynamic healthcare delivery reporting systems 236 can include a blood-testing device that is implanted into the body (e.g. under the skin) or worn in the form of a patch and configured to detect biochemical information regarding at least one of: glucose levels, cortisol levels, potassium levels, blood oxygen levels, blood alcohol levels, inflammation, nitric oxide levels, drug levels/residues present in the body, pathogens present in the body, or bacteria present in the body, folic acid levels, calcium levels, magnesium levels, creatine kinase levels, vitamin B12 levels, vitamin D levels, ferritin levels, total cholesterol levels, hemoglobin, HDL, LDL, triglycerides, fatty acids, insulin, hormones (e.g. thyroid hormones (thyroid-stimulating hormone (TSH), metabolic hormones, reproductive hormones, etc.), liver enzymes, electrolytes (e.g. sodium, potassium, chloride, etc.), platelets, white blood cells, red blood cells, iron, etc.

In another example, the dynamic healthcare delivery reporting systems 236 can include can include a device that is configured to detect and determine physiological information regarding electrical activity of the brain (also referred to as neurofeedback). According to this example, the dynamic healthcare delivery reporting systems 236 can include a near-infrared spectroscopy (NIRS) spectroscopy sensor configured to determine hemodynamic information such as working memory performance levels, stress levels and attention levels of the patient. The neurofeedback can also include brain activity information determined by an electroencephalogram (EEG) sensor worn by the patient. For example, EEG measurements can include voltage fluctuations in the time and/or frequency domain that can be correlated to mental performance with respect to various defined cognitive function areas, including but not limited to: attention, familiarity, mental effort, working memory, linguistic acquisition, social learning, and medication.

It should be appreciated that the above described medical monitoring devices (and the associated types of physiological information capable of being detected/determined by these devices), are merely exemplary and that other existing and future implantable/wearable devices capable of detecting additional types of physiological information can be employed.

In other implementations, the patient data 238 can include information observed by or determined by a clinician and entered into an electronic tracking system that records and reports observed changes in physiological states of a patient. For example, the electronic tracking system can receive information observed and/or determined by a first responder, paramedic, nurse, physician, etc., regarding the physiological state or condition of the patient over the course of care. The manner in which this patient data 238 is input to the electronic tracking system can vary (e.g., as text, a voice to text input, natural language input, and the like). In another example, the patient data 238 can be received from an electronic symptom tracking system that receives information entered by the patient (or an authorized agent of the patient) regarding self-reported medical symptoms or other information about how the patient is feeling mentally and/or physically (e.g., level of pain experienced, level of energy, stress level, mood information, etc.).

The workflow data 240 can include real-time information regarding the clinical workflow followed for a patient over the course of care, including clinical events that occur over the course of care. In this regard, the workflow data 240 can identify and describe medical treatment provided to a patient by one or more clinicians over the course of care. This can include but is not limited to: procedures performed, specific steps of the procedures performed, relevant aspects/parameters associated with respective steps, timing and order of the steps, medical instruments/supplies used, clinicians involved in performance of procedural steps, roles and actions performed by the respective clinicians, medications administered, dosage of the medications administered, timing of patient check-ups, and the like. Like patient data, the specific workflow events that are tracked and reported in-real time can vary based on the clinical context of each patient. For example, with respect to a patient in labor, the workflow data 240 can include information regarding treatment provided by clinicians to the patient over the course of labor (e.g., administering of drugs, surgical procedural steps, etc.), including information identifying the clinicians and the specific actions they performed and clinical decisions made (e.g., decision to induce). In another example, with respect to a surgical procedure, the workflow information can include specific parameters related to the physical actions performed by the surgeon. For instance, the workflow information can identify the location of incision, the size of the incision, the physical relation of a medical instrument to an anatomical part of the patients' body (e.g., captured via one or more sensors associated with the medical instrument, such as a camera, a pressure sensor, etc.), and the like.

The types of the dynamic healthcare delivery reporting systems 236 from which the workflow data 240 is received can vary. In some embodiments, at least some of the workflow data can be received from an electronic tracking system configured to receive user input recording workflow events over a course of patient care. For example, the user input can be provided by one or more clinicians involved with treating the patient or monitoring the treatment of the patient. In another embodiment, at least some workflow data 240 regarding actions performed by clinicians, locations of clinicians and the like, can be received from one or more motion or movement sensors worn by clinicians. In another embodiment, at least some of the workflow data 240 can be received from an image data monitoring system configured to capture and/or receive live video at a healthcare facility. For example, the live video can be received from cameras worn clinicians, patient, and other entities at the healthcare facility. In another example, the live video can be received from one or more stationary cameras located at various locations throughout the facility. According to this embodiment, the image data monitoring system can be configured to employ live video processing techniques to automatically identify objects, people, and other things included in the image data. The video processing techniques can also be configured to determine actions performed by clinicians, patients and the like, based on the image data. In another embodiment, at least some of workflow data 240 can be received from an audio monitoring system configured to receive and evaluate audio, including speech, in real-time. For example, the audio monitoring system can determine words spoken, actions, performed and the like, based on analysis of the audio.

The clinician data 242 can include real-time information associated with respective clinicians that can influence their ability to provide quality patient care. In this regard, the clinician data 242 can identify the current clinicians that are available for performing patient care (e.g., clinicians that are on the clock, clinicians that are on-call), current locations of respective clinicians, and current activities being performed by clinicians (e.g., administering anesthesia to patient John Doe in operating room 303), and the like. The clinician data 242 can also track the current workload of a clinician, including the number of patients being treated and scheduled to be seen, type of extent of treatment required by the clinician for each patient, and the like. The clinician data 242 can also include information regarding the current physiological and mental status of clinicians (e.g., fatigue, stress levels, etc.).

The types of dynamic healthcare delivery reporting systems 236 from which the clinician data 242 is received can vary. In some embodiments, at least some of the clinician data 242 can be received from one or more devise worn by or otherwise physically coupled to the clinicians. For example, clinician data 242 including information regarding the physiological and/or mental states of the clinicians can be received from various types of biofeedback sensors worn by the clinicians. In another example, information regarding current locations of clinicians can also be tracked by devices worn by or coupled to the clinicians. The locations of clinicians can also be determined using various other automated object location tracking techniques. In another example, information regarding current workloads of clinicians (e.g., including number of patients being treated, type of treatment required, etc.) can be received from scheduling systems, patient tracking systems, and the like.

The facility data 244 can include dynamic contextual data regarding a current context or state of a healthcare facility. This can include contextual information that can change over the course of a minute, an hour, a day, and the like. For example, the facility data 244 can include real-time information regarding the status and availability of resources provided by the facility, including rooms, medical equipment and medical supplies. The facility data 244 can also include real-time activity information that tracks the events and activities occurring throughout the healthcare facility in real-time (e.g., what clinical and non-clinical actions are being performed at respective locations of the healthcare facility). The types of dynamic healthcare delivery reporting systems 236 from which the facility data 244 is received can vary. For example, the facility data can be received from automated video monitoring systems, inventory monitoring systems, and the like.

The external data sources/systems 106 can also include historical workflow information 220 database. The historical workflow information 220 can include historical information recorded for past patients regarding any monitored parameters associated with their course of care. In one or more embodiments, this can include historical patient data (e.g., patient data 238), historical workflow data (e.g., workflow data 240), historical clinician data (e.g., clinician data 242) and/or historical facility data (e.g., facility data 244) provided by the dynamic healthcare delivery reporting systems 236 associated with a past patient's course of care. For example, for respective past patients, the historical workflow information 220 can identify a condition or diagnosis of the patient, information identifying or describing the physiological state/condition of the patient at the time of arrival at the healthcare facility (or at the time when treatment was initiated), detailed parameters regarding what treatment was provided to the patient, including clinical actions that were taken in association with treatment and when, the clinical reactions or outcomes of the respective actions, what clinicians performed respective actions, states of the clinicians at the time of performance of the respective actions, physiological states of the patient associated with respective actions, contextual state of the healthcare facility over the course of care (e.g., adequately staffed or not, number of patients admitted, status of medical resources available, etc.), and the like.

In various embodiments, the historical workflow information 220 can be used (e.g., by the AI model development system 112 of the AI orchestration layer 110, as discussed infra) to develop and/or train various AI models configured to make inferences, evaluations, determinations, and/or recommendations regarding clinical and/or operational actions, events, conditions, and/or issues associated with one or more clinical and/or operational workflows of a healthcare organization. On the other hand, the various types of healthcare data provided by the dynamic healthcare delivery reporting systems 236 can be used (e.g., by the AI workflow assistance system 116 of the AI orchestration layer 110, as discussed infra) as new input to the respective models during actual, live operations of the healthcare organization to generate and provide, in real-time or substantially real-time, inferences, evaluations, determinations, and/or recommendations regarding clinical and/or operational actions, events, conditions, and/or issues associated with one or more clinical and/or operational workflows of a healthcare organization.

It should be appreciated that various additional data sources can be employed to provide input data points that can be used in association with developing and applying AI healthcare models configured to provide AI informatic and inferences in various clinical and healthcare domains. In this regard, the internal data sources/systems 104 and/or the external data sources/systems 106 of the back-end integration layer 102 can include any potential information source or system that can provide and/or employ insight regarding any facet of operation and performance of the healthcare organization, facility, research instruction and the like, from the patients and healthcare personnel to physical tools and structures associated with the integrated healthcare organization. In this regard, the types of healthcare data that can be used as input for AI healthcare model training and model application is not limited to those describe herein.

With reference again to FIG. 1, the AI orchestration layer 110 can provide various processing functions associated with developing and provisioning AI informatics in various domains/industries. In this regard, the AI orchestration layer 110 can provide orchestration functions associated with developing and refining domain specific AI models by one or more machine learning model development systems based on the vast amounts of diverse domain related data provided by the back-end integration layer 102. The AI orchestration layer 110 can further facilitate integrating and applying the one or more AI models into actual industry operational workflows. In the embodiment shown, the AI orchestration layer 110 can include AI model development system 112, AI model database 114, AI workflow assistance system 116, and one or more other IT services 118.

The AI model database 114 can provide one or more AI models configured to provide AI informatics associated with various domains/industries. For example, as applied to healthcare, the AI model database 114 can provide one or more healthcare AI models configured to provide AI informatics associated with various healthcare domains. In this regard, the models included in the AI model database 114 can be configured to process various types of healthcare input data provided by the back-end integration layer 102 to generate various clinical and/or operational inferences, determinations, evaluations, recommendations, etc., based on the data. For example, the models included in the AI model database 114 can include one or more diagnostic models configured to generate diagnostic information based on medical image and signal data, patient physiological information (e.g., including signs/symptoms), patient medical history/record information, patient laboratory information/test results, patient omics data, and the like. According to this example, the diagnostic models can be configured to not only generate diagnosis information that diagnosis a patient condition or state, but also provide information regarding a level of confidence of the diagnosis (e.g., 76% probability of a diagnosis of condition A, 24% probability of diagnosis of condition B, etc.).

In another example, the models included AI model database 114 can include medical ordering models configured to determine information regarding how to treat a patient based on a diagnosis of the patient, a current state of the patient, medical history of the patient, signs and symptoms, demographic information, insurance information and the like. For instance, the ordering models can generate information regarding recommended medical tests/studies to be performed, procedures to be performed, medications to administer, physical activities to perform (or not perform) rehabilitation/therapy activities to perform, dietary restrictions, etc. In another example, the AI model database 114 can include one or more healthcare AI models configured to generate information regarding recommended courses of care for specific patients and specific clinical and/or operational contexts that facilitate optimal clinical and/or financial outcomes. The AI models can also include models configured to identify clinical and operational variances in workflows relative to SOPs, clinical complications, responses to remediate clinical complications, and the like. In another example, the AI models can include models configured to provide recommendations regarding assigning clinicians to specific patients (e.g., based on learned performance and competency levels of the clinician, the condition of the patient, preferences of the clinician preferences of the patient, etc.). In another example, the AI models can include one or more models configured to determine recommendations regarding how to prioritize placement of patients to a limited number of beds in a medical facilate based on patient needs, a state of the healthcare facility, predicted occupancy levels and the like.

The types of outputs generated by the AI models included in the AI model database 114, the number of models and the diversity of the models can vary. It should be appreciated that a wide array of sophisticated healthcare AI informatics and associated models are possible given the granularity, diversity and massive amount of healthcare data that can be provided by the back-end integration layer 102, as well as the distributed learning processing functionality afforded by system 100 as discussed herein. In this regard, the various example AI models discussed above merely provide a small taste of the possible applications of AI informatics in healthcare that can be enabled by the distributed learning architecture of system 100. The distributed learning architecture of system 100 is also designed such that existing models included in the AI model database 114 can be regularly updated and refined, and new models can be added to the AI model database 114 over time as new input data is received, new technology arises, and the like.

The AI model development system 112 can provide the analytical tools for developing and training the various healthcare AI models included in the AI model database 114 based at least in part on the healthcare input data provided by the back-end integration layer 102. In this regard, the AI orchestration layer 110 can be coupled to the back-end integration layer 102 via one or more back-end interfaces/gateways 108. The one or more back-end interfaces/gateways 108 can provide flexible interfaces allowing for the training data to be consumed by the AI model development system 112. For example, in one or more embodiments, the back-end interfaces/gateways 108 can provide domain and site-specific interfaces to back-end enterprise systems and sources (e.g., as an adapter/abstraction layer). In this regard, the AI orchestration layer 110 can enable access to training data from curated data repositories provided by the various disparate data sources of the back-end integration layer 102.

The AI workflow assistance system 116 can provide the analytical tools for applying the healthcare AI models post-development/training to facilitate enhancing clinical and operational workflows of various healthcare systems. In this regard, the AI workflow assistance system 116 can provide interoperability to assert the healthcare AI models included in the AI model database 114 as part of clinical routine, while further facilitating continuous updating and versioning of the models by the AI model development system 112. For example, in one or more embodiments, the AI workflow assistance system 116 can interface with one or more software applications employed by a healthcare organization to facilitate clinical and/or operational workflows of the healthcare organization. For instance, one example software application can include a medical imaging visualization/interaction application configured to provide functions associated with viewing and evaluating medical images by physicians (or patients, or other appropriate entities). According to this example, the AI workflow assistance system 116 can facilitate identifying and calling one or more applicable AI models from the AI model database 114 in association with usage of the imaging application by a physician and applying the one or more AI models to generate automated (e.g., AI based) diagnostic evaluations of the images being viewed by the physician. The AI workflow assistance system 116 can further facilitate providing the AI model results to the physician (e.g., via the imaging application) during the clinical workflow. In some embodiments, the AI model development system 112 can further regularly receive feedback regarding results generated by the AI healthcare models when applied to actual workflows and employ the feedback to regularly update and/or optimize the one or more healthcare AI models provided in the AI model database 114.

The AI orchestration layer 110 can also include one or more additional IT services 118 that can provide various services associated with integrating one or more features and functionalities of the AI orchestration layer 110 with other systems, devices (e.g., client device 124) and/or applications associated with the front-end interaction/visualization layer 122 and the back-end integration layer 102. For example, the one or more additional IT services 118 can facilitate provision of healthcare AI data models (e.g., included in the AI model database 114 and/or provided by the AI model development system 112) for use by various entities and systems. The one or more additional IT services 118 can also facilitate querying the models included in the AI model database 114, as well as data elements and training data included in the back-end integration layer 102 by multiple systems (investigators) for building new models and algorithms. The AI orchestration layer 110 can thus maximize reuse and sharing of the data models and training data that scales across different enterprises, enterprise departments and regions. In some implementation, the one or more additional IT services 118 can also provide tools for systematically and uniformly generating structured data (e.g., included in the structured training data database 208) for training the common data models and new healthcare AI models.

Various exemplary embodiments of the disclosed subject matter are directed to AI informatics in medical imaging. Medical imaging is one of the fastest-moving areas of discovery in the AI healthcare arena. For example, AI can be used to generate automated evaluations of medical image data, offering radiologists, pathologists, ophthalmologists, and practitioners in other image-rich disciplines the opportunity to augment their workflows. The various features and functionalities of system 100 described herein provide for generating major improvements to AI tools in the medical imaging domain.

In this regard, give the amount and diversity of the training data provided by the back-end integration layer 102, and the processing capabilities afforded by the distributed model development environment of the AI model development system 112, highly precise medical image analysis algorithms can be developed with enhanced analytical functions over those capable of being performed by humans. For example, when humans view and evaluate medical images, they look at reconstructed transforms of raw image data. However, the raw data pieces of the source image data (e.g., pixel data, waveform data, etc.) could have patterns in features that cannot be seen by the human eye which could be correlated to specific anatomical features, defects, diagnosis, and the like. Because the back-end integration layer 102 can provide both DICOM and reconstructed versions of images as well as the raw image data used to generated the reconstructed version of the images, AI algorithms can be generated by the AI model development system 112 that are intelligent enough to identify correlations in data points in image data on this level of granularity to generate inferences on the data. In addition, because the back-end integration layer 102 provides various additional types of multi-dimensional input data that can be associated with medical image data set for a patient, such as the patient's medical history, omics data, demographic data, etc., the AI model development system 112 can further identify patterns and correlations between many additional relevant data points to facilitate evaluating medical images to identify defined features in the images, diagnostic interpretations of the images and the like.

In addition, to the level of granularity in the intelligence capabilities that can be achieved based on the amount and diversity of the training data, the degree of efficiency and accuracy in generating medical image AI models is greatly enhanced by the mechanisms for generating structured/annotated training data described herein. In this regard, as discussed in greater detail infra with reference to FIGS. 5 and 7, annotated medical images and associated textual report data providing interpretations of the annotated medical images can be efficiently generated for teaching and training purposes over the course of the clinical routine performed by physicians. The techniques for generating the annotated medical images and textual report data can further facilitate uniformity and consistency in the training data by restricting the ontologies, vocabularies, terms and the like, that is used to annotate the medical images and describe the images in the textual reports. As a result, highly precise, structured medical image training data can be regularly generated over time in an efficient manner, allowing for not only generating enough sample to develop and train the image algorithms, but further continuously update and optimize the algorithms as new training data is received. In this regard, the medical imaging algorithms can become smart enough to not only generate diagnostic evaluations of the image data, but further highlight and identify key features in the image data for presenting to the radiologist when the images are viewed in clinical practice. In essence, the algorithms can become sophisticated enough to automatically or self-annotate the medical images.

Further, in addition to developing and training such highly intelligent AI image analysis informatics, the disclosed techniques provide for actually integrating and applying the medical image AI models in clinical workflows of radiologists by the AI workflow assistance system 116. As a result, the superior AI algorithm solutions afforded by system 100 will create significant time savings with the generation of radiology reports, as well as highlight key findings. This technology will have a profound effect, including enhanced diagnosis and incidental findings of images, predictive image analysis, and workflow efficiency with data analysis, report generation, and prioritization of key findings.

Furthermore, system 100 provides for receiving feedback during the clinical workflow from an interpreting physician regarding whether and to what degree one or more results generated by the AI image analysis models is correct. For example, in association with viewing and evaluating a medical image of the brain, one or more AI imaging algorithm can provide information identifying a tumor in the image and describing a degree of malignancy of the tumor. The interpreting clinician can further provide feedback that indicates whether and to what degree the AI model results are correct. This feedback can be associated with the image and fed back to the AI model development system 112 to further refine the one or more models.

Figure 3:
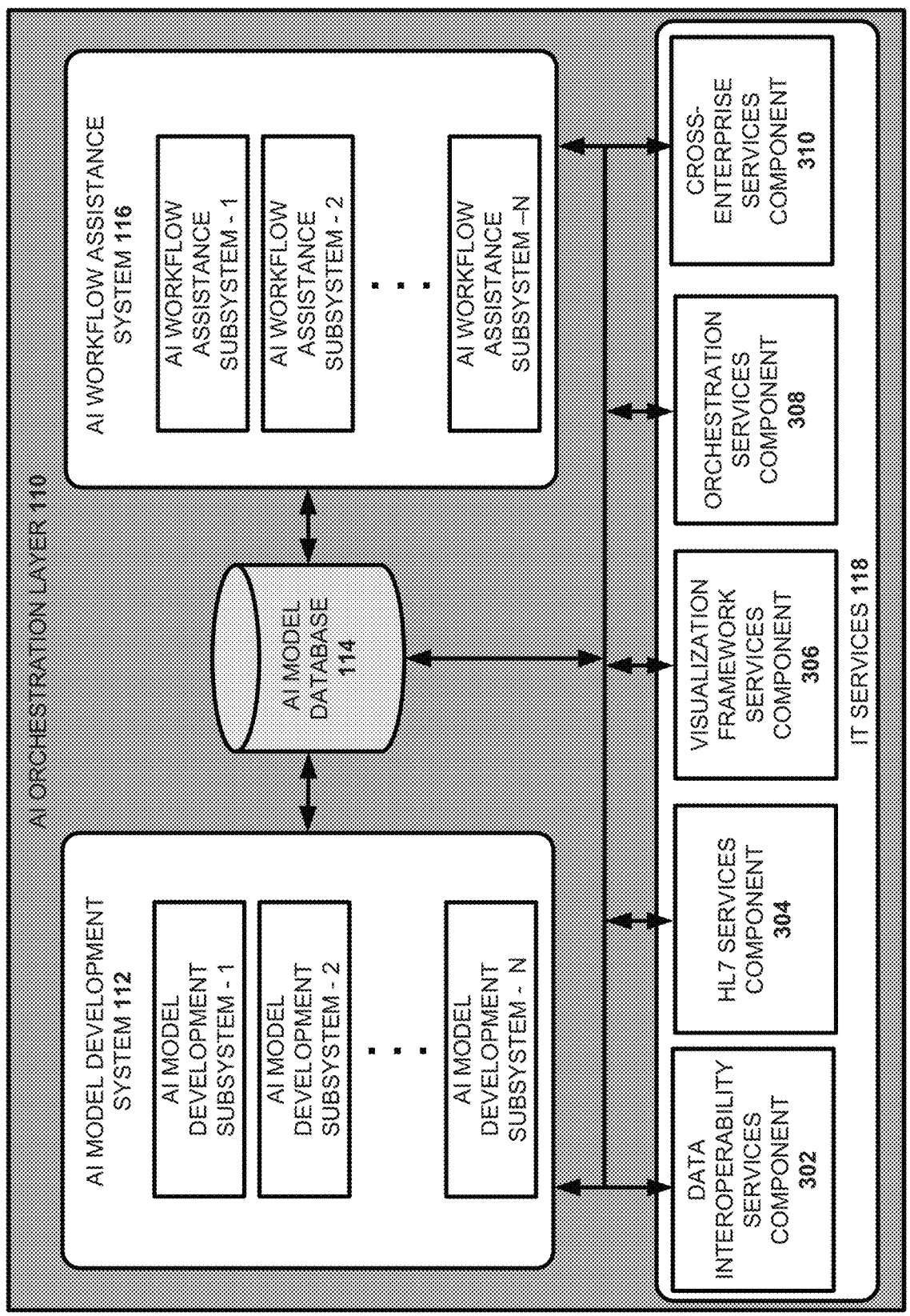
FIG. 3 illustrates a block diagram of an example, non-limiting AI orchestration layer of a distributed learning architecture that facilitates integrating AI informatics in healthcare systems, in accordance with one or more embodiments of the disclosed subject matter.

FIG. 3 illustrates a more detailed representation of the AI orchestration layer 110 in accordance with one or more embodiments of the disclosed subject matter. Repetitive description of like elements employed in respective embodiments is omitted for sake of brevity.

In one or more embodiments, the AI model development system 112 can comprise a collaborative model building, training/development environment that includes a plurality of disparate yet collaborative AI model building systems. Although synthesizing vast amounts of domain/industry related information from disparate sources enables generation of more targeted and accurate AI models, the challenge of analyzing so much data is quickly outpacing many solo providers abilities. The AI model development system 112 tackles this obstacle by leveraging the machine learning libraries, tools and powerhouses of many different AI development systems. In this way, the AI orchestration layer 110 can be agnostic in the marketplace as to "who" is doing the teaching and training piece for the development of the various AI models included in the AI model database 114, as well as "where" the teaching and training processing is being performed. In this regard, this distributed learning architecture of the AI model development system 112 supports many machine learning development scenarios, including on premises development, cloud-based development, and multi-regional data center development.

For example, in the embodiment shown, the AI model development system 112 can include a plurality of AI model development subsystems, respectively identified as AI model development subsystem 1, AI model development subsystem 2, and so on. The number of AI model development subsystems can vary (e.g., can include any wherein N is an integer). These AI model development subsystems can include one or more internal model development systems (e.g., provided by the same entity as that owns and/or operates the one or more internal data sources/systems 104), one or more external or third-party model development systems, cloud-based model development systems, on premises model development systems, and the like. For example, in some implementations, one or more of the AI model development subsystems can be associated with an internal learning factory provided by the same entity associated with the internal data sources/systems 104. One or more of the AI model development subsystems can also include one or more external or third-party systems configured to provide AI algorithm teaching and training tools, machine learning algorithm libraries and models, and the like (e.g., Partners Health Systems (PHS)™ Corporation, NVIDIA™ Corporation, and the like).

Figure 5:
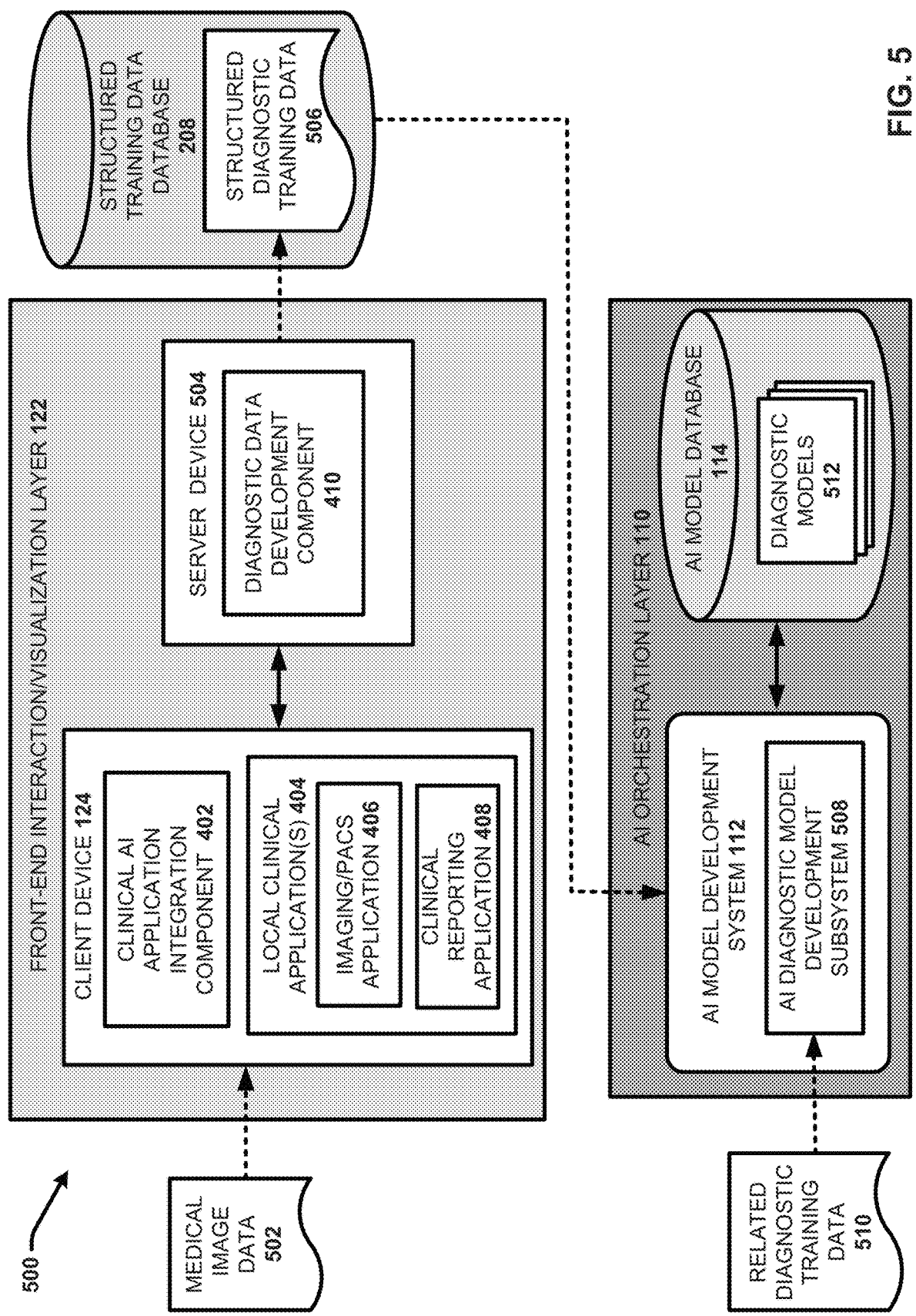
FIG. 5 illustrates a block diagram of an example, non-limiting system that facilitates generating one or more diagnostic models in association with integrating AI informatics in healthcare systems using a distributed learning architecture, in accordance with one or more embodiments of the disclosed subject matter.
Figure 7:
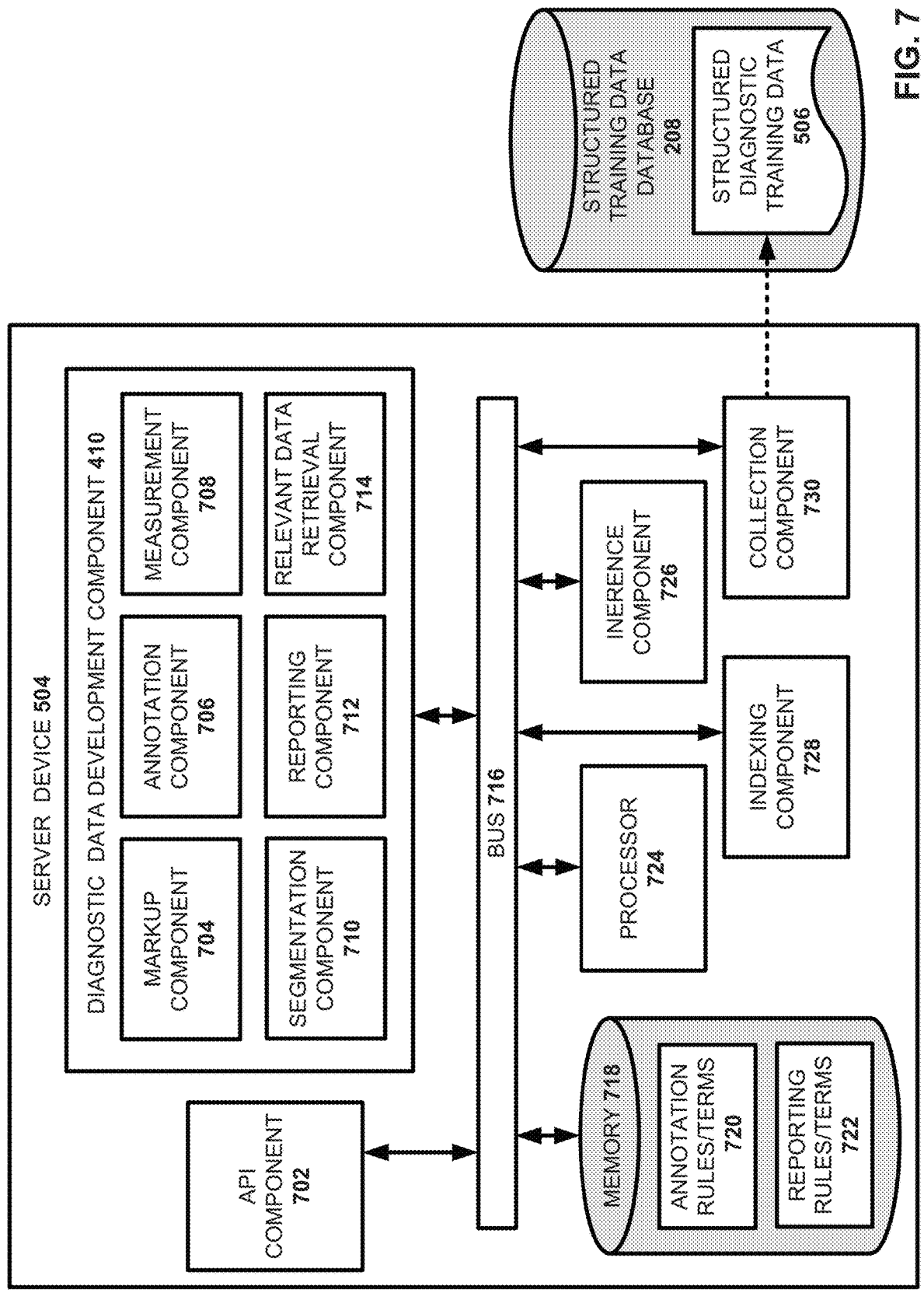
FIG. 7 illustrates a block diagram of an example, non-limiting server device that facilitates generating structured diagnostic training data in association with integrating AI informatics in healthcare systems using a distributed learning architecture, in accordance with one or more embodiments of the disclosed subject matter.

In one or more implementations, the various AI model building subsystems can be configured to provide various proprietary and non-proprietary machine learning tools and services to collectively generate the one or more AI healthcare models included in the AI model database 114 based at least in part on the healthcare data provided by the back-end integration layer 102 (which can include structured annotated training data generated using the techniques described herein in greater detail with reference to FIGS. 5 and 7). For example, the machine learning techniques can include various supervised machine learning techniques, including but not limited to deep learning techniques, neural networks, convolutional neural networks, support vector machines (SVM), linear regression, decision trees, naive Bayes, nearest neighbor, and other data driven techniques. In some implementations, the machine learning techniques can also include unsupervised machine learning techniques, semi-supervised machine learning techniques, reinforcement learning, and the like.

Another challenge to the integration of AI informatics into various healthcare domains resides in the need for highly targeted models with defined scopes that solve specific healthcare problems in a meaningful manner. For example, each clinical question requires a different model and a different set of input data and level or type of training. The AI model development system 112 can tackle this problem by distributing generation of different models tailored to different clinical and/or operational questions/problems to different training and development subsystems. For example, in one or more embodiments, the model building and development subsystems can be respectively configured to generate different targeted analytical models that facilitate generating inferences in different healthcare domains, including clinical domains (e.g., medical imaging, diagnostics, medical ordering, etc.), and operational domains (e.g., workflow optimization, waste management, billing and claims, etc.). For example, one AI model development subsystem of the AI model development system 112 can be configured to generate AI models directed to evaluating medical image data for diagnostics while another subsystem can be configured to generate AI models directed to determining medical orders, or prescriptions, or determining optimal workflows, and the like. In another example, within a specific healthcare field, different AI model development subsystems can be further tailored to address different subfields associated therewith. For example, with respect to the medical imaging field, different subfields can be defined based different image acquisition technologies (e.g., x-ray, CT image data, MRI image data, etc.), different data types (e.g., a non-contrast CT scan verses a CT angiography data set), different areas of the body, different conditions, and the like. In this regard, each of the AI models included in the AI model database 114 can respectively be tailored to address a specific input data set and generate a specific output. The level of specificity of each model can vary. Furthermore, some AI models can be related in a manner such that an output of one model can be used as an input for another. For example, a first model can be configured to identify tumors in medical image data, and a second model can be configured to evaluate the identified tumors to determine levels or grades of identified tumors, etc.

The AI workflow assistance system 116 can facilitate running or applying the trained models included in the AI model database 114 to make actual inferences regarding a domain specific problem the respective AI models are configured to solve. For example, as applied to healthcare, the AI workflow assistance system 116 can facilitate running or applying the trained models included in the AI model database 114 to make actual inferences regarding clinical and administrative workflows. For example, as discussed in greater detail infra with reference to FIGS. 9-11 and 12A-12D, the AI workflow assistance system 116 can facilitate applying trained medical image AI models to medical image data to facilitate radiologists, pathologists, and the like, when interpreting and evaluating medical image data. For instance, in some implementations, the AI workflow assistance system 116 can apply one or more medical imaging models to process medical image data, and potentially other related input data (e.g., patient medical history, omics data, laboratory data, etc.), to generate diagnostic information regarding a patient condition reflected in the image, to generate automated medical report information providing an interpretation of the medical image data, and the like. In some implementations, one or more medical imaging models included in the AI model database 114 can be trained to not only generate a diagnostic interpretation of the image data, but to further visually identify features of interest included in a medical image. For example, the one or more imaging models can identify and define a boundary of a tumor or lesion represented in a medical image. With these implementations, the AI workflow assistance system 116 can further integrate with a medical imaging visualization application employed by the radiologist to facilitate generating graphical marks on the medical image as presented to the radiologist via the application (e.g., on device display), that highlight, encircle, mark or otherwise visually call out the identified tumor or lesion.

The integration of medical imaging AI models into radiologist workflows described above merely provides one example use case of the AI workflow assistance system 116. In this regard, the AI workflow assistance system 116 can be configured to integrate appropriate healthcare AI models into various clinical and operational workflows. For example, the AI workflow assistance system 116 can be configured to facilitate applying medical ordering models after a diagnosis or evaluation of a patient medical condition has been established to facilitate providing recommendations regarding orders for subsequent aspects of treatment of the patient. In another example, the AI workflow assistance system 116 can be configured to monitor courses of patient care in real-time using one or more AI models to identify variances from SOPs and provide recommendations regarding clinical actions to perform over the course of care of the patient based the condition of the patient, the state of the healthcare facility, the medical instruments available, and the like. In another example, the AI workflow assistance system 116 can be configured to evaluate bed requests at an inpatient medical facilitate using one or more AI models configured to generate prioritization information regarding how to fulfill the bed requests and assign patients to a limited number of beds.

In this regard, similar to the distributed learning environment provided by the AI model development system 112 wherein different model development subsystems can be configured to develop and train different AI models in specific healthcare domains and subdomains, the AI workflow assistance system 116 can include a plurality of AI workflow assistance subsystems that can respectively be configured to apply the respective models to facilitate different types of workflows. In this regard, in one or more embodiments, each AI workflow assistance subsystem (respectively identified as AI workflow assistance subsystem –1, AI workflow assistance subsystem –2, and so on), can be configured to evaluate a different set of input data and apply one or more different AI models to generate different clinical and/or operational inferences, recommendations, and oversight for different types of clinical and/or operational problems.

Accordingly, the different AI workflow assistance subsystems can respectively provide clinical decision support in various healthcare domains and contexts. Clinical decision support refers to any tool that provides clinicians, administrative staff, patients, caregivers, or other members of the care team with information that is filtered or targeted to a specific person or situation. In this regard, the AI workflow assistance system 116 can provide a variety of clinical decision support tools, such as tools that provide diagnostic interpretations of medical image and signal data, tools reduce clinical variation and duplicative testing, tools that suggest next steps for treatments, tools that alert providers to available information they may not have seen, tools that catch potential problems such as dangerous medication interactions, and the like. In addition, the respective AI workflow assistance subsystem can be configured to provide clinical decision support by not only selecting and applying the appropriate AI models to a clinical context or workflow, but further delivering the right information (evidence-based guidance using the appropriate AI model or models and in response to a clinical need) to the right people (entire care team—including the patient) through the right channels (e.g., EHR, mobile device, patient portal) in the right intervention formats (e.g., order sets, flow-sheets, dashboards, patient lists) at the right points in workflow (for decision making or action).

The AI orchestration layer 110 as shown in FIG. 3 further provides some example IT services 118 that can be included in the AI orchestration layer 110. In the embodiment shown, these example IT services 118 can include a data interoperability services component 302, an HL7 services component 304, a visualization framework services component 306, an orchestration services component 308, and a cross-enterprises services component 310.

The data interoperability services component 302 can facilitate configuring healthcare data retrieved from various disparate data sources of the back-end integration layer 102 into a standard format that can be consumed by the AI model development system 112 and the AI workflow assistance system 116. In this regard, the data interoperability services component 302 can facilitate efficient data exchange and usage by various disparate enterprises in association with collaboration between the systems to generate AI models and integrate AI analytics.

The health level 7 (HL7) services component 304 can facilitate data exchange and retrial between disparate data sources and systems provided by the back-end integration layer 102 in accordance with HL7 standards. HL7 refers to a set of international standards for transfer of clinical and administrative data between software applications used by various healthcare providers. For example, hospitals and other healthcare provider organizations typically have many different computer systems used for everything from billing records to patient tracking. These systems should communicate with each other when they receive new information, or when they wish to retrieve information. HL7 specifies a number of flexible standards, guidelines, and methodologies by which various healthcare systems can communicate and share information processed in a uniform and consistent manner.

The visualization framework services component 306 can include one or more processing components that provide a library and set of core services related to accessing, processing, viewing and/or interacting with medical image data. For example, the visualization framework services component 306 can provide an imaging channel to medical image data sources (e.g., provided by the medical image archiving system 202, the PACSs 212, the VNAs 214, etc.) to enable accessing, parsing and retrieving medical images. The visualization framework services component 306 can further facilitate accessing and using one or more medical imaging visualization systems (e.g., medical image visualization system 204) that provide one or more applications for viewing and interacting with medical images, generating reconstructed medical images, and the like.

The orchestration services component 308 can provide various processing functions that facilitate the features and functionalities of the AI model development system 112 and the AI workflow assistance system 116. For example, the orchestration services component 308 can facilitate synchronization with the radiology desktop (study and patient context), calling of appropriate analytic services models, interaction with back-end services like reporting systems/data interfaces, and the like. The orchestration services component 308 can also provide the business logic to drive the teaching and training collaboration between the various subsystems of the AI model development system 112.

The cross-enterprises services component 310 can include one or more processing components that enable interrogation of multiple information systems provided in the back-end integration layer 102. For example, the cross-enterprises services component 310 can include adapters (Fast Healthcare Interoperability Resources (FHIR)-based) to enable ingestion of EHR data in accordance with standards for governing patient security and anonymity. In some embodiments, the cross-enterprises services component 310 can also allow for the interrogation of remote PACS and the streaming of studies into the visualization framework services component 306 provided by the visualization framework services component 306 to allow a creation of a unified patient jacket. The cross-enterprises services component 310 can further provide intelligent patient-matching mechanisms (ontology-based) and access of master patient index (MPI) information to facilitate identifying and gathering all relevant information for dataset pertaining to one or more patients for consumption by the AI model development system 112 and the AI workflow assistance system 116. For example, the cross-enterprises services component 310 can extract data from disparate data sources provided by the back-end integration layer 102 that is related to a specific patient, group of patients, imaging study and the like, and packet the data into a unified data set that facilitates evaluating correlations between various types of data points associated within the respective data sets. In some implementations, the cross-enterprises services component 310 can identify relevant and related data provided by various data sources included in the back-end integration layer 102 needed for development of specific AI models, extract it, and further normalize it so it can be efficiently used for model creation. For example, the cross-enterprises services component 310 can identify related data objects included in one or more data sources of the back-end integration layer 102 can generate data set cohorts. For instance, with respect to AI medical image analysis models, the cross-enterprises services component 310 can identify set of images for a patient study, medical report data that interprets the images, patient information that identifies a patient ID associated with the data set, classification information that classifies one or more characteristics of the data set (e.g., negative chest x-ray), and the like.

With reference again to FIG. 1 the front-end interaction/visualization layer 122 can facilitate user interaction in association with consuming data and services provided by the back-end integration layer 102 and/or the AI orchestration layer 110. For example, (with reference to FIGS. 1 and 3) in one or more embodiments in which system 100 is applied to healthcare, the front-end interaction/visualization layer 122 can facilitate accessing and consuming medical imaging visualization services provided by the visualization framework services component 306, the using a suitable client device (e.g., of one or more client devise 124). The front-end interaction/visualization layer 122 can also integrate unique tools that facilitate generating structured straining data for the development of domain specific AI models and applying the AI models in actual operational workflows. For example, as applied to healthcare systems, the front-end interaction/visualization layer 122 can provide a zero-footprint visualization layer that serves as a means to generate structured annotated training data in routine clinical practice by clinicians, as well as means to serve as a diagnostic, visualization layer that delivers AI results and feedback into the clinical workflow. In the embodiment shown, the front-end interaction/visualization layer 122 can include one or more client devices 124 and one or more AI interaction/visualization applications 126.

The client devices 124 can include various types of devices associated with users of system 100 via which the users can consume data and services provided by system 100. For example, some suitable client devices can include but are not limited to a desktop computer, a laptop computer, a television, an Internet enabled television, a mobile phone, a smartphone, a tablet personal computer (PC), or a personal digital assistant (PDA), a heads-up display (HUD), an augmented reality (AR) device, a virtual reality (VR) device, a wearable device, an implanted medical device (IMD), a medical instrument or device capable of receiving and applying computer readable instructions (e.g., an imaging device, robotics instrument, etc.), and the like. In the various embodiments, one or more of the client devices 124 can be configured to provide for rending information to a user of the client device using as suitable output component, such as a display, a speaker, a sensory or haptic feedback device, and the like. For example, in some embodiments, one or more of the client devices 124 can include a desktop computer of a radiologist via which the radiologist accesses and/or executes a medical imaging visualization/interaction application to view and interact with medical images.

The term user or end-user as used herein can refer to any entity that uses data and/or services provided by system 100. In this regard, a user or end-user can include can include human users as well as machines, devices, and systems. For example, in some contexts, an end-user can include a physician that uses the new annotation techniques described herein to generate structured training data during clinical practice. In another context, an end-user can include a hospital administrator that receives clinical decision support (e.g., afforded by the AI workflow assistance system 116 using one or more appropriate healthcare AI models included in the AI model database 114), in association with determining patient placements to beds at an inpatient medical facility. In yet another example, an end-user can include a robotic medical instrument configured to receive and automatically apply AI model-determined instructions regarding how to articulate or position a probe within a body of a patient.

The AI interaction/visualization applications 126 can include one or more applications that facilitate integrating unique tools that facilitate generating structured training data and providing healthcare AI model analytical results in clinical and/or operational workflows. For example, the AI interaction/visualization applications 126 can include one or more applications that provide interaction paradigms patterns/for more efficiently presenting unstructured input data and training tools to annotators in association with generating structured/annotated training data. In another example, the AI interaction/visualization applications 126 can include an application that facilitates integration of AI model results and feedback into the clinical workflow by presenting or otherwise providing the end user with clinical decision support and facilitating reception of user feedback to further validate and tailor the healthcare AI models.

The manner of deployment of the AI interaction/visualization applications 126 can vary. For example, in some embodiments the AI interaction/visualization applications 126 can comprise one or more web-applications. For example, in some implementations, the web-applications can include angular-based applications. In other implementations, the web-applications can be non-angular web applications. In accordance with this embodiment, the AI interaction/visualization applications 126 (angular-based or not angular-based) can be configured to consumes the imaging services provided by the visualization framework services component 306. As a web-application, the AI interaction/visualization applications 126 can comprise their own cod-based binary/object code. In other embodiments, the AI interaction/visualization applications 126 can comprise one or more cloud-applications, one or more thin client applications, one or more thick client applications, one or more native client applications, one or more hybrid client applications, or the like. In this regard, although the AI interaction/visualization applications 126 are shown as being part of the front-end interaction/visualization layer 122, in other embodiments, the AI interaction/visualization applications 126 and/or one or more components of the AI interaction/visualization applications 126 can be part of the AI orchestration layer 110.

Figure 4:
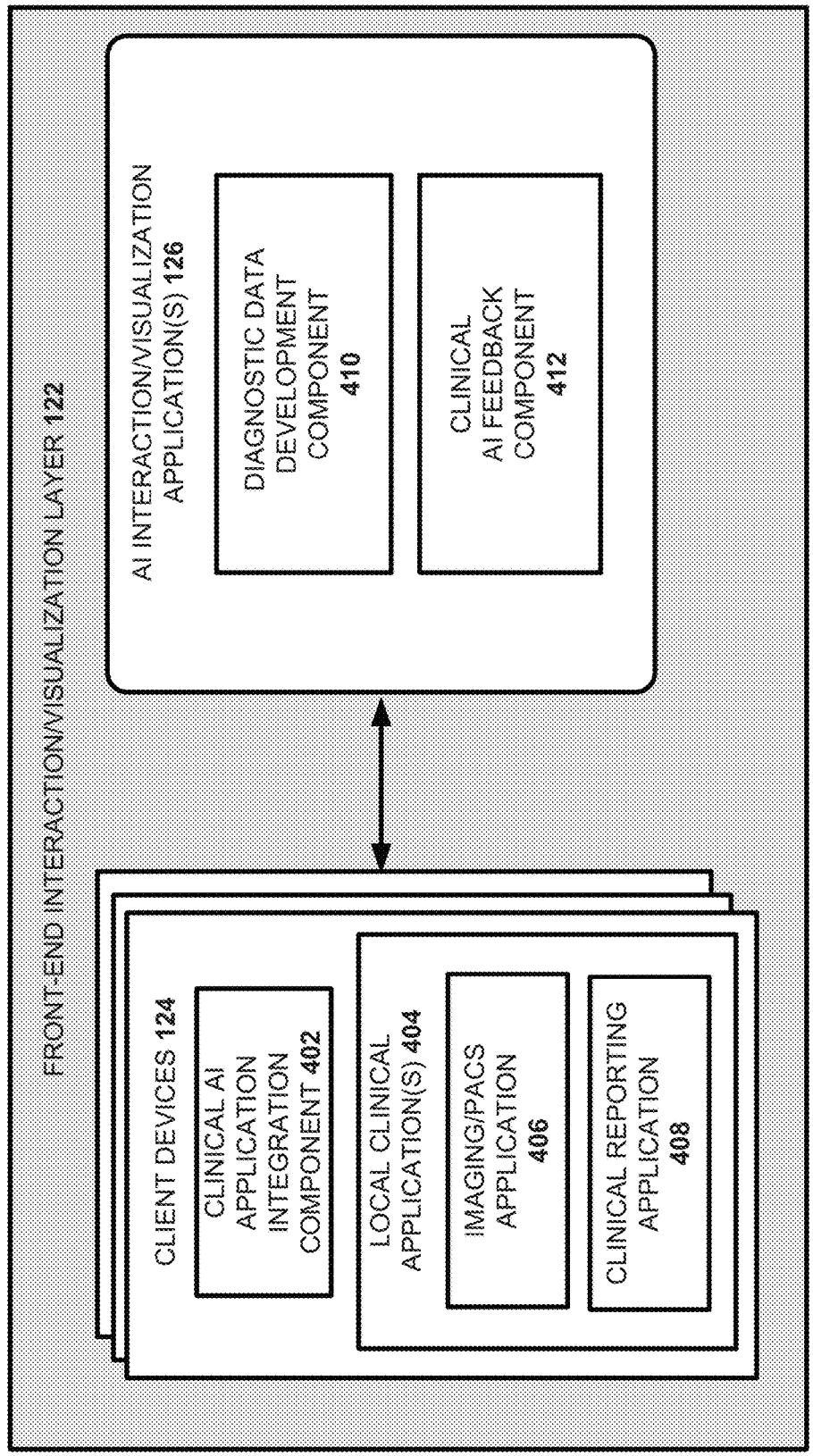
FIG. 4 illustrates a block diagram of an example, non-limiting front-end interaction/visualization layer of a distributed learning architecture that facilitates integrating AI informatics in healthcare systems, in accordance with one or more embodiments of the disclosed subject matter.

FIG. 4 illustrates a block diagram of a more detailed representation of the front-end interaction/visualization layer 122 in accordance with one or more embodiments of the disclosed subject matter in association with integrating AI informatics into healthcare systems. Repetitive description of like elements employed in respective embodiments is omitted for sake of brevity.

In some embodiments, the AI interaction/visualization applications 126 can comprise two separate applications, one for facilitating annotating and generating structured training data, and another for delivering the AI model results in association with application of the models to clinical and/or operational workflows. For example, in the embodiment shown, the two separate applications are represented by diagnostic development component 410 and clinical AI feedback component 412. The diagnostic data development component 410 is described in greater detail infra with reference to FIGS. 5-8, and the clinical AI feedback component 412 is described in greater detail infra with reference to FIGS. 9-11 and 12A-12D.

In the embodiment shown, the client device 124 comprises local clinical applications 404, including an imaging/PACs application and a clinical reporting application 408. The imaging/PACs application 406 can comprise a medical imaging application such as those described herein (e.g., in association with medical image visualization system 204), which facilitates accessing, viewing and interacting with medical images via a graphical user interface (GUI) displayed at the client device 124. The clinical reporting application 408 can include a reporting application such as those described herein (e.g., in association with medical reporting system 206) that facilitates generating medical reports, such as medical reports that provide information describing interpretations of medical images and/or other diagnostic data associated a patient, medical reports that describe an in-person medical evaluation of a patient, and the like. Although the imaging/PACS application 406 and the clinical reporting application 408 are shown as separate applications, in some embodiments, these applications can be combined into a single application/service. In some implementations, the imaging/PACs application 406 and the clinical reporting application 408 can include entirely local client applications configured to load and review medical images in an offline mode. In other implementations, the imaging/PACs application 406 and the clinical reporting application 408 can comprise web-applications, thin-client applications, thick-client applications, hybrid applications, etc. configured to access medical images and other patient data as well as image processing/visualization services provided by one or more medical imaging/visualization systems (e.g., using the visualization framework services component 306).

In accordance with this example embodiment, the client device 124 can include a device associated with a physician (e.g., a radiologist's desktop) that provides local/resident medical imaging/reporting software (e.g., the imaging/PACs application 406 and the clinical reporting application 408) at the client device 124 (e.g., stored in memory of the client device 124 and executed by a processor of the client device 124). For example, the medical imaging/reporting software can comprise legacy and/or proprietary medical imaging software provided by and used by a particular healthcare system, wherein the medical image/reporting software does not include the AI features and functionalities of the AI interaction/visualization applications 126. In particular, many hospital IT systems use existing medical imaging software applications for accessing and viewing medical images, generating medical reports and the like. With this embodiment, the client device 124 can continue to use the legacy medical imaging/reporting software provided by the hospital IT system, yet also employ the features and functionalities of the AI interaction/visualization applications 126 via the clinical AI application integration component 402.

For example, the clinical AI application integration component 402 can function as a local desktop agent that facilitates interoperability between the AI interaction/visualization applications 126 and the local clinical applications using a respective application program interfaces (APIs) of the local clinical applications 404 and the AI interaction/visualization applications 126, respectively. This solves the problem of lack of interoperability between integrating the AI informatics provided by the AI interaction/visualization applications 126 and the existing medical imaging/reporting systems employed by some hospital IT systems. Accordingly, the clinical AI application integration component 402 facilitates integration and provision of AI insight and information in association with usage of existing medical imaging/reporting technology, thereby eliminating the need for the hospital IT system having to implement millions of dollars in new software. For example, the clinical AI application integration component 402 can provide information and notifications to the local clinical applications 404 regarding AI inferences and results determined by the AI interaction/visualization applications 126 in association with evaluating medical images and associated information being consumed by the local clinical applications 404.

In other embodiments, the front-end interaction/visualization layer 122 can provide and/or employ a new AI medical imaging/visualization application and/or AI reporting application that combines the various features and functionalities of existing PACS and reporting systems (e.g., imaging/PACS application 406 and clinical reporting application 408), as well as the features and functionalities of the AI interaction/visualization applications 126, into a single application. With these embodiments, the unified application can comprise a web-application, a thin client application, a hybrid application, and the like. In some implementations, the features and functionalities of this unified application can be provisioned by the visualization framework services component 306.

With reference again to FIG. 1, in some embodiments, in addition to the three primary layers (e.g., the back-end integration layer 102, the AI orchestration layer 110, and the front-end interaction/visualization layer 122), system 100 can also include one or more consortium systems 128, a consortium datastore 130 and a domain cloud 132. These additional components of system 100 can be communicatively coupled to one another and the respectively layers to facilitate sharing of information and services between the respective components of system 100.

The consortium systems 128 can partner applications that can be provided with the healthcare AI models included in the AI model database 114, as well as the structured training data developed in accordance with the techniques described herein. For example, the can be partners involved in the controlled network of system 100 with whom data sets that have been annotated and marked up using the consistent tooling described herein can be shared. The consortium systems 128 can also provide additional data sets for model training and development. The consortium datastore can compile information and data provided by the consortium systems 128 as well as the information developed by the AI orchestration layer for efficient and seamless access and utilization.

The domain cloud 132 can provide anther means for combining relevant domain data and services from multiple source into a network accessible cloud-based environment. For example, in embodiments in which system 100 is employed to facilitate integrating AI informatics into various healthcare systems, the domain cloud 132 can correspond to a health cloud. For example, the domain cloud 132 can include cloud storage 140 that combines electronic medical records, medical device data, even wearables, into a single location. In some embodiments, the structured diagnostic data, including annotated medical images, medical report terms, and the like generated using the techniques described herein (with reference to FIGS. 5 and 7), can also be stored in the cloud storage 140. The domain cloud 132 can include a results display component 134 that facilitates receiving and view AI results generated by the AI workflow assistance system 116 by various entities across the globe. The domain cloud 132 can also include an AI model manager component 136 that can facilitate identifying, accessing and employing appropriate AI healthcare models included in the AI model database 114 by the consortium systems 128.

The domain cloud 132 can also include domain literature/regulatory data 138. The domain literature/regulatory data 138 can include essentially any form of information related to the domain that system 100 is applied to that can be queried and retrieved via a network (e.g., the Internet) that can be used by the AI orchestration layer 110 to develop and train AI models and/or apply the AI healthcare models in practice. For example, in embodiments in which system 100 is applied to healthcare, the domain literature/regulatory data 138 can include can include various sources of electronic literature providing medical information, including textbook data used to train clinicians in various areas and specialties of healthcare delivery, information describing known medical conditions and diagnosis, information describing known medical procedures and complications, information describing pharmaceuticals, information describing medical instruments, supplies and devices, medical research data, and the like. The domain literature/regulatory data 138 can also include information regarding guidelines and/or restrictions providing standards for exchanging/sharing of patient information (e.g., in accordance with the Health Insurance Portability and Privacy Act (HIPPA), as well as clinical regulations for practicing medicine (e.g., in accordance with the Federal Drug Administration (FDA) and the like).

The deployment architecture of system 100 can vary. However, it should be appreciated that although not shown, the various systems, services, devices, applications, components and the like, of system 100, can be coupled to at least one memory that stores the computer executable components or the front-end interaction/visualization layer 122, the AI orchestration layer 110, and the back-end integration layer 102. Further the various systems, services, devices, applications, components and the like, of system 100 can be communicatively coupled to at least one processor that executes the computer executable components. In various embodiments, one or more of the various systems, services, devices, applications, components and the like, of system 100 can be deployed in a cloud architecture, a virtualized enterprise architecture, or an enterprise architecture wherein one the front-end components and the back-end components are distributed in a client/server relationship. With these embodiments, the features and functionalities of one or more of the various systems, services, devices, applications, components and the like, of system 100 can be deployed a web-application, a cloud-application, a thin client application, a thick client application, a native client application, a hybrid client application, or the like, wherein one or more of the front-end components are provided at a client device 124 (e.g., a mobile device, a laptop computer, a desktop computer, etc.) and one or more of the back-end components are provided in the cloud, on a virtualized server, a virtualized data store, a remote server, a remote data store, a local data center, etc., and accessed via a network (e.g., the Internet). Various example deployment architectures for system 100 are described infra with reference to FIGS. 15-20.

While one or more systems, services, devices, applications, components and the like, of system 100 are illustrated as separate components, it is noted that the various components can be comprised of one or more other components. Further, it is noted that the embodiments can comprise additional components not shown for sake of brevity. Additionally, various aspects described herein may be performed by one device or two or more devices in communication with each other. For example, one or more systems, services, devices, applications, components and the like, of system 100 can be located on separate (real or virtual) machines and accessed via a network (e.g., the Internet).

FIG. 5 illustrates a block diagram of an example, non-limiting system 500 that facilitates generating one or more diagnostic models in association with integrating AI informatics in healthcare systems using a distributed learning architecture, in accordance with one or more embodiments of the disclosed subject matter. In various embodiments, system 500 is a subsystem of system 100. In this regard, system 100 can include system 500 and vice versa. Various elements of system 100 (e.g., the back-end integration layer 102) are removed from system 500 merely to enable a more focused description of system 100 in association with implementation of system 100 to generate structured diagnostic training data (e.g., structured diagnostic training data 506). Thus, system 500 can include one or more elements of system 100 that are not shown in system 500 (and vice versa). Repetitive description of like elements employed in respective embodiments is omitted for sake of brevity.

System 500 presents an example embodiment of system 100 in association with application of system 100 to facilitate generating the structured diagnostic training data 506 based in part on evaluation of medical image data 502 by physicians during routine clinical practice. For example, the medical image data 502 can include DICOM medical images, native medical images in a non-DICOM format, reconstructed medical images, and the like. With reference to FIGS. 1, 2, 3 and 5, in various embodiments, the medical image data 502 can be provided by one or more data sources/systems of the back-end integration layer 102 (e.g., the medical image archiving system 202, the medical image visualization system 204, the one or more PACSs 212, and/or the one or more VNAs). The AI orchestration layer 110 can further facilitate identification, exaction and provision of the relevant medical image data 502 (e.g., for a particular patient, study, group of patients/studies, etc.) being evaluated to the client device 124 for rendering. For example, in some implementations, the visualization framework services component 306 can facilitate identification, exaction and provision of the relevant medical image data 502 to the client device 124 during runtime in association with usage of the imaging/PACS application 406 by the client device 124.

Figure 6:
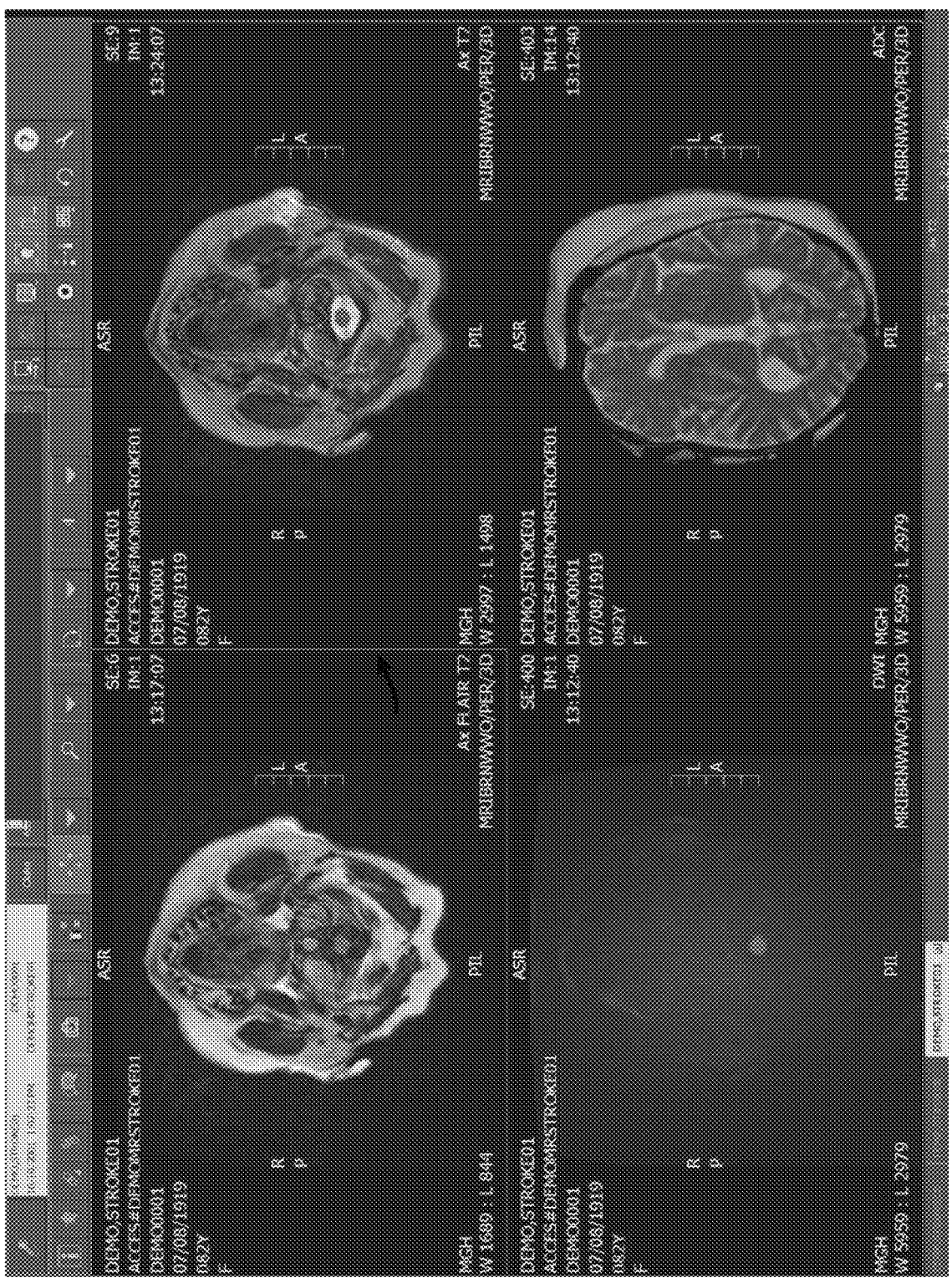
FIG. 6 presents an example visualization comprising medical images that can be generated and presented to a physician in association usage of a medical imaging application, in accordance with one or more embodiments of the disclosed subject matter.

System 500 is described in association with evaluation of the medical image data 502 by a physician (e.g., a radiologist) at a client device 124 accessible to the physician in association with routine clinical practice using an imaging/PACS application 406 and a clinical reporting application 408. In this regard, the imaging/PACS application 406 can facilitate generating a graphical user interface (GUI) via which the medical image data 502 can be presented to the clinician for viewing (e.g., via a display of the client device 124). For example, FIG. 6 presents an example visualization comprising medical images that can be generated and presented to a physician in association usage of the imaging/PACS application 406 or a similar application. In the embodiment shown, several different MRI views of a patient MRI brain scan are presented in different windows for viewing by the physician.

With reference again to FIG. 5, in some implementations, the imaging/PACS application 406 can further provide various interactive functions that allow the physician to select and load specific images or imaging studies for viewing, interact with the images as displayed, transition from viewing different types of images and perspectives, generate and/or view reconstructed (3D) images, edit the images, and the like. The clinical reporting application 408 can similarly provide an interactive user facing application that can facilitate entering information by the physician (e.g., using a predefined template or form, in free form text, in speech to text, etc.) describing an interpretation of the medical image data, describing an in-person evaluation of a patient, describing an interpretation of other diagnostic information received for the patient (e.g., lab data, vital signs and other physiological signals provided by a non-image based medical device, etc.), and the like.

Although the imaging/PACS application 406 and the clinical reporting application 408 are shown as local applications to the client device 124, it should be appreciated that system 500 is not limited to this deployment architecture. For example, in one embodiment, the imaging/PACS application 406 and/or the clinical reporting application 408 can be stored in memory (not shown) of the client device 124 and executed by a processor (not shown) or the client device 124. In other embodiments, one or more features and functionalities of the imaging/PACS application 406 and/or the clinical reporting application 408 can be located at one or more external devices, (e.g., an external server, virtual machine, etc.) and accessed by the client device 124 via a suitable network.

In various embodiments, the diagnostic data development component 410 can be provided by one or more devices external to the client device 124 and accessed by the client device 124 via one or more suitable networks. For example, in the embodiment shown, the diagnostic data development component 410 can be provided by a server device 504 that is remote from the client device 124. In this regard, the diagnostic data development component 410 can be stored in memory (not shown) of the server device 504 and executed by a processor (not shown) of the server device 504. With this implementation, the client device 124 can include and employ a local desktop agent (e.g., the clinical AI application integration component 402) to access and integrate the features and functionalities of the diagnostic data development component 410 into the clinical workflows provided by the imaging/PACS application 406 and/or the clinical reporting application 408. In other embodiments, one or more features and functionalities of the imaging/PACS application 406, the clinical reporting application 408 and the diagnostic data development component 410 can be provided by a single application (e.g., a web-application, a thin client application, a thick client application, a local client application, a hybrid application, etc.).

The diagnostic data development component 410 can provide additional features and functionalities than those provided by conventional medical imaging and reporting applications (e.g., imaging/PACS application 406 and/or clinical reporting application 408) to facilitate the generation of structured diagnostic training data 506 in association with routine clinical usage of such medical imaging and reporting applications. For example, in one or more embodiments, the diagnostic data development component 410 can facilitate integrating new annotation tools with the imaging/PACS application 406 that provide for annotating the medical image data 502 in association viewing and interacting with the medical image data 502 during their routine clinical practice. The techniques for annotating the medical image data 502 can facilitate generating uniformly annotated medical images with mark-ups, text, symbols, and the like, applied thereto (as described infra with reference to FIG. 7). In this regard, in addition to facilitating generation of structured diagnostic data during routine clinical practice of reading and interpreting medical images by radiologists, the diagnostic data development component 410 can facilitating generation of structured diagnostic data according to one or more defined ontologies. An ontology encompasses—representation, formal naming, and definition of the categories, properties, and relations between the concepts, data, and entities that substantiate one, many, or all domains. In this regard, the diagnostic data development component 410 can define the vocabularies that can be used to describe the medical image data, the terms and/or visual marks and symbols that can be used for respective types of features and images, the meanings of the terms and/or visual marks or symbols, the relationships between terms, and the data model or format in which the applied terms/marks descriptions and the like is associated with the medical image data.

In addition to annotated medical image, the diagnostic data development component 410 can further facilitate integrating new medical reporting tools with the clinical reporting application 408 that facilitates generating uniform medical report data according to one or more defined ontologies (as also described infra with reference to FIG. 7). For example, the uniform medical report data can provide a diagnostic interpretation of one or more medical image with constant terminology, vocabularies, formats, etc. In the embodiment shown, the annotated medical image data and uniform medical report data are collectively referred to as structured diagnostic training data 506.

The structured diagnostic training data 506 generated by the diagnostic data development component 410 can be stored at one or more centralized databases for access, re-use and sharing to various entities and enterprises. For example, in the embodiment shown, the structured diagnostic training data 506 is stored in the structured training data database associated with one or more internal data systems/sources of the back-end integration layer 102, as described with reference to FIG. 2. In other embodiments, the structured diagnostic training data 506 can be provided in cloud storage 140, at the consortium datastore 130, or another centralized databased accessible by the AI model development system 112 and other collaborative systems and enterprises. Because the structured diagnostic training data 506 is generated in accordance with one or more defined ontologies, common data structures, vocabularies, terms, etc., the structured diagnostic training data 506 can enable efficient teaching of models offline and online based on consistent patterns. In addition, by using coming ontologies, data structures, vocabularies terms, etc., the structured diagnostic training data 506 maximizes reuse, sharing, model development and inferencing that scales across departments, enterprises and regions.

In accordance with various embodiments, the structured diagnostic training data 506 can be used as training data by the AI model development system 112 for generating one or more AI models configured to automatically interpret new medical image data. For example, in the embodiment shown, the AI model development system 112 can include an AI diagnostic model development subsystem 508 that can be configured to employ the structured diagnostic training data 506 (e.g., including annotated medical images and structured diagnostic report data) to develop and/or train one or more diagnostic models 512 using various supervised (and in some implementations unsupervised) machine learning techniques. For example, the structured diagnostic training data can be used to either augment an already existing supervised learning model (enriching the training data) or used to develop a new mathematical model or classifiers. The one or more diagnostic models 512 can be configured to evaluate medical image data (and potential other related input data points) to generate a diagnosis based on the image data, to identify and characterize features of interest and/or defects in the image data, and the like.

In some embodiments, the AI diagnostic model development subsystem 508 can also identify and employ related diagnostic data 510 that is related to the structured diagnostic training data (e.g., corresponding raw image data, corresponding patient EHR data, corresponding patient omics data, medical literature data, etc.) to facilitate uncovering hidden correlations in between data points included in the structured diagnostic training data 506 and the related diagnostic training data that could not be performed by routine human clinical evaluation. The related diagnostic data 510 can be identified and extracted by the AI orchestration layer 110 from the disparate data sources and systems provided by the back-end integration layer 102, the consortium datastore 130, the domain cloud 132 and the like.

In various embodiments, the AI diagnostic model development subsystem 508 can be configured to generate a plurality of different diagnostic models 512 respectively configured to interpret different data sets. For example, the respective diagnostic models can be configured to interpret different types of medical image data (e.g., X-ray, CT scan, contrast CT scan, non-contrast CT scan, MRI, etc.), different types of medical conditions in the image data (e.g., one model looking for tumors or lesions, another looking for fractures), medical images associated with different body parts, etc. In another example, some of the respective diagnostic models 512 can be configured to interpret non-image input data associated with a patient (e.g., omics data, laboratory data, recorded symptoms, recorded physician notes based on an in-person patient evaluation, patient HER data, etc.) to determine diagnostic information for the patient. The level of granularity of the respective diagnostic models 512 can vary. In this regard, although the AI diagnostic model development subsystem 508 is depicted with a single box as a single "subsystem," it should be appreciated that the AI diagnostic model development subsystem 508 can further be divided into a plurality of different subsystems that are respectively configured to generate different types of diagnostic models 512 respectively configured to interpret different data points and generate different outputs.

In some implementations, a group of two or more models can be used to evaluate a data set associated with a patient comprising diverse types of data points (e.g., different types of image data, non-image data, etc.) to facilitate generating diagnostic information for the patient. According to this implementation, the respective diagnostic models 512 can be configured to process subsets of data points included in the data set to generate different outputs related to the patient diagnosis. In some implementations, outputs of some of the diagnostic models 512 can be used as inputs to other ones of the diagnostic models 512 included in the group.

FIG. 7 illustrates a block diagram of an example, non-limiting server device 504 that facilitates generating structured diagnostic training data in association with integrating AI informatics in healthcare systems using a distributed learning architecture, in accordance with one or more embodiments of the disclosed subject matter. Repetitive description of like elements employed in respective embodiments is omitted for sake of brevity.

In addition to the diagnostic data development component 410, the server device 504 can include application program interface (API) component 702, inference component 726, indexing component 728 and collection component 730. The server device 504 can include or be communicatively coupled to at least one memory 718 that stores computer executable components. These computer executable components can include for example, the API component 702, the diagnostic data development component 410, the inference component 726, the indexing component 728 and the collection component 730. The memory 718 can also store annotation rules/terms 720 and reporting rules/terms 722. The server device 504 can further include processor 724 to execute these computer executable components. The server device 504 can also include a system bus 716 to communicatively couple the various components of the server device 504 (e.g., the API component 702, the diagnostic data development component 410, the memory 718, the processor 724, the inference component 726, the indexing component 728 and the collection component 730.

With reference to FIGS. 5 and 7, the API component 702 can facilitate integrating one or more features and functionalities of the diagnostic data development component 410 and inference component 726 with the imaging/PACS application 406 and the clinical reporting application 408 of used by the client device 124. For example, the API component 702 can facilitate accessing the imaging/PACS application 406 and the clinical reporting application 408 in real-time during usage of the respective applications at the client device 124. In this regard, the API component 702 can interface with the clinical AI application integration component 402 and vice versa, to receive information regarding the medical image data 502 being evaluated using the imaging/PACS application 406 and the clinical reporting application 408, and to provide relevant annotation and reporting tools provided by the diagnostic data development component 410 and the inference component 726 to facilitate generating the structured diagnostic training data 506.

In the embodiment shown, the diagnostic data development component 410 can include markup component 704, annotation component 706, measurement component 708, segmentation component 710, reporting component 712 and relevant data retrieval component 714.

The markup component 704 can facilitate applying graphical markings on a feature of interest present in the medical image data 502 as displayed via a GUI at the client device 124. The markup component 704 can further generate structured diagnostic training data 506 including structured markup data that identifies a location of the feature of interest relative to the medical image data. For example, the markup component 704 can allow for the radiologist viewing the medical image data to apply 'markups' on the images or signal artifacts at various locations and depths. These markups can be presented via a set of graphical tools in the imaging software used by the interpreting physician. For example, the markup component 704 can apply overlay or segmentation of defects and areas of interest on the rendered data-set. The graphical representations of the markup areas of the data can be stored in digital means using coordinate pairings and the extent of the boundary of the feature of interest. For example, in various embodiment, the DICOM™ standard Grey Scale Presentation State, for instance, can be used to collect and persist these markups. The markup component 704 can also restrict the manner in which applied markups are related to features of interested in the image data in accordance with one or more defined data models.

The annotation component 706 can facilitate applying an annotation to a feature of interest present in the medical image data 502 as displayed via a GUI at the client device 124. The annotation component 706 can further generate structured diagnostic training data 506 that includes structured annotation data that identifies the feature of interest relative to the medical image data and associates the annotation with the feature. In this regard, not only can the disclosed annotation tools provided for identifying or marking a defect or feature of interest, but also allow physicians to apply defined text and/or symbols annotations to the defect or feature, wherein the text and/or symbols provide additional defined descriptive information about the defect or feature of interest. The annotation component 706 can further restrict and/or control the manner in which text and/or symbols can be applied to medical image data 502 and the terms and/or symbols that can be used in accordance with defined annotation rules (e.g., defined data models and ontologies), terms or vocabularies. For example, in the embodiment shown, the defined annotation rules and terms or vocabularies can be stored in memory 718 as annotation rules/terms 720. By limiting the terms and vocabulary that can be used for annotating medical images, ambiguity in training and teaching will be avoided. An additional benefit of this approach is the clarity of communication to clinical care teams that will also use these data in the treatment of a patient.

In some embodiments, the annotation component 706 can determine or infer one or more annotation terms that are relevant to the medical image data being evaluated and provide the one or more annotation terms to the annotator (e.g., via the GUI) for potential application to the medical image data or a feature of interest identified or marked in the medical image data. The annotation component 706 can further restrict application of annotations to the medical image data based on the one or more relevant annotation terms. For example, based on the type of medical image being viewed, the body part represented in the medical image, the perspective of the image, one or more characteristics of a feature of interest (e.g., the position, area or volume of a feature of interest, pixel coloration data, pixelated pattern data, etc.) included in the medical image data (e.g., a feature of interest marked by the annotator using the markup component 704 and/or extracted by the segmentation component 710), the medical history of the patient, etc., the annotation component 706 can identify a subset of relevant terms and/or symbols defined in the annotation rules/terms 720 that are relevant for potential application to the medical image. In some implementations, the annotation component 706 can employ AI and one or more classifiers to determine or infer the relevant annotation terms. In this regard, the annotation component 706 can employ a heuristic to determine and recommend an appropriate set of vocabulary or terminology for annotating a particular medical image, and/or feature or defect identified in the medical image.

The measurement component 708 can facilitates applying measurements to a feature of interest present in the medical image data as displayed via the GUI and generate structured diagnostic training data 506 including structured measurement data that identifies the feature of interest relative to the medical image data and associates the measurement with the feature. For example, the structured measurement data can define one or more dimensions of the feature of interest (e.g., an area, volume, length, width, etc.). In some implementations, the measurement component can determine the dimension based in part on reception of input selecting or marking the feature of interest on the medical image data via the GUI. In this regard, in association with identifying a feature of interest in a medical image (e.g., a lesion, a tumor, a fracture, a herniated disc, a medical device, inflamed tissue, etc.), the measurement component 708 can allow the radiologist to measure the area or volume of a feature of interest directly on the image data. These measurements are key in determining a medical diagnosis, an appropriate treatment and/or efficacy of treatment. Often these measurements are not 'saved' to the imaging study because the information technology (IT) systems used for managing the image data do not always handle these data types well. With the disclosed techniques, the measurement component 708 can generate and save the measurement data in accordance with a defined data model or standard-based format that can be consistently used by one or more machine learning systems (e.g., of the AI model development system 112) for model training and development.

The segmentation component 710 can apply one or more segmentation tools to identify and segment visually distinct features included in medical image data. The segmentation component 710 can further automatically or semi-automatically extract the segmented features from the medical imaging data and generate structured segmentation data identifying the distinct visual features. For example, in some embodiments, the segmentation component 710 can be configured to extract a feature included in medical image data based on application of a markup to the feature using the markup component 704 and/or the measurement component 708. In this regard, based on user input identifying a feature, defining a dimension of the feature, drawing a circle or box around the feature or the like, the segmentation component 710 can separate the feature from the image data and for further annotation and evaluation. The segmentation component 710 can also store image data of the feature as extracted or segmented from the original image data. In another embodiment, the segmentation component 710 can analyze medical image data to automatically identify visually distinct features based on visual pixel coloration and texture data associated with the features, dimension of the features, arrangement of the features, positions of the features and the like. With these embodiments, the segmentation component 710 can be configured to identify defined patterns in the image data using one or more heuristic. In some implementation, the segmentation component 710 can further classify segmented features.

The reporting component 712 can facilitate extracting or generating structured training data from diagnostic reports prepared by the interpreting clinicians in clinical practice. For example, in diagnostic radiology and cardiology, the diagnostic physician communicates his or her interpretation of the data via a textual report. The terminology, descriptors and information in these reports can be key parameters in algorithm training and development. The reporting component 712 can facilitate generating a textual diagnostic report regarding a diagnostic interpretation of the medical image data in accordance with defined ontologies, rules and terms as defined in memory by as reporting rules/terms. The reporting component 712 can further generate structured textual report data based on the textual diagnostic report. For example, in some implementations, the reporting component 712 can restrict the terms and vocabular that can be used in a diagnostic report in accordance with the reporting rules/terms. For example, the reporting component 712 can determine a subset of medical terms or information categories for potential inclusion in the textual diagnostic report based in part on the medical image data being evaluated, as well as other relevant information associated with the patient in the patients' EHR (e.g., medical history information, demographic information, medication information, etc.), omics data for the patient, lab data for the patient, and the like. In some embodiments, the reporting component 712 can employ AI and one or more classifiers to determine or infer the subset of appropriate medical terms or information categories. The reporting component 712 can further restricts content for inclusion in the textual diagnostic report based on the subset of appropriate medical terms or information categories.

In some implementations, during the creation of the interpretative report, the reporting component 712 can further facilitate contextually aware reporting and guide the physician through each step of the reporting process. For example, based on analysis of aspects of the image data being evaluated and/or other data associated with the patient for which the report is being made, meta-data and other queues, the reporting component 712 can determine an appropriate report template or an option of choices of defined information categories and present the template and/or information categories to the interpreting physician. In some implementations, the reporting component 712 can select the template and/or option of reporting information categories from a defined set included in the reporting rules/terms 722. The terms and vocabulary that can be included in the report can further be standardized and controlled by reporting component 712 and are configurable by the system administrator. In this regard, the reporting component 712 can identify contextually relevant tags and terms used in the interpretation report and generate structured diagnostic training data 506 that includes the relevant report tags and terms. In some implementations, the reporting component 712 can further provide embedded or adaptive reporting tools. In this regard, the reporting component 712 can automatically determine or infer one or more appropriate terms and/or description for including in a medical report and fill them in automatically.

In some embodiments, the reporting component 712 can employs NLP to identify one or more semantically relevant terms or phrases included in the textual diagnostic report. With these embodiments, the reporting component 712 can generate the structured textual report data using the semantically relevant terms or phrases. For example, in association with usage of a conventional clinical reporting application (e.g., clinical reporting application 408) to generate medical reports using free text and natural language, the reporting component 712 can evaluate the medical report using NPL techniques to grab and extract semantically relevant terminology from the just-completed interpretative report. In this regard, the NLP techniques can provide automated algorithms configured to parse and extract key concepts in text data that will be useful and needed in building a learning model from the diagnostic data. The reporting component 712 can further convert NPL terms into structured machine-readable terms in accordance with the ontologies, terms and rules defined in the reporting rules/terms.

The relevant data retrieval component 714 can facilitate identifying, retrieving information provided by one or more data sources/systems of the back-end integration layer 102, the health cloud, the consortium datastore 130 and the like, that is relevant to a medical report being created by a clinician in association with usage of the clinical reporting application 408 (or a similar application). In some implementations, the reporting component 712 can further automatically populate or otherwise fill out terms, description and categories included in the report based on the retrieved information. For example, in association with evaluation of a medical image study for a patient, the relevant data retrieval component 714 can identify and retrieve information included in the patients EHR regarding the patient's demographics, medical history, insurance information, recorded signs and systems, and the like and include relevant portions of the patient's EHR into the report. In other embodiments, the relevant data retrieval component 714 can determine or infer information that would be helpful or otherwise relevant to the interpreting clinician in association with evaluating the patient image data (or other diagnostic data) when generating an interpretation of the data. For example, the relevant data retrieval component 714 can identify related studies for other similar patients with similar symptoms, signs, and medical images, and provide the clinician with information regarding the related studies. In another example, the relevant data retrieval component 714 can find medical literature (e.g., textbook data, clinical research reports, recent disease reports/outbreak statistics for a potential condition reflected in the patient data, etc.) provided by information included in the domain cloud 132 related to a particular patient's imaging study, laboratory data, medical history, omics data, etc. that could facilitate diagnosis or otherwise evaluating the patient's condition. For example, the relevant data retrieval component 714 can determine that a patient for which a report is being generated is a cancer patient, and from a cross-sectional medical image of the patient's chest that there is a sarcoid that has an 80% chance of being malignant. According to this example, the relevant data retrieval component 714 can identify medical image data for other patients that have a similar sarcoid matching the current sarcoid/patient profile and provide these images to the radiologist for review and/or including in the report for the oncologist.

The inference component 726 can be configured to provide for or aid in various inferences or determinations associated one or more features and functionalities of the diagnostic data development component 410. For example, the inference component 726 can facilitate the annotation component 706 in association with inferring which features included in medical images should be annotated and what annotations (e.g., what terms and symbols) to apply to the respective features. In another example, the inference component 726 can facilitate the measurement component 708 in association with inferring, based on analysis of image data and/or a marking applied to the image, a dimension (e.g., scaled or actual) associated with an anatomical feature of interest (e.g., size of a tumor, amount of herniation of a disc relative to a reference point, depth of a fracture, etc.). In another example, the inference component 726 can facilitate the segmentation component 710 in association with identifying distinguishable features included in medical image data and separating segmenting the features from a medical image or reconstructed 3D medical image for isolated annotation, analysis and pattern recognition. In another example, the inference component 726 can facilitate the reporting component 712 in association with inferring, recommending and/or automatically entering relevant information and information categories in a medical report in accordance with the reporting rules/terms 722. In yet another example, the inference component 726 can facilitate the relevant data retrieval component 714 in association with inferring whether and what information available to the server device 504 in the various data sources/systems accessible to the server device in the back-end integration layer, the consortium datastore 130 and the health cloud is relevant to a medical report being generated by a clinician based on the patient and data set for the patient for which the medical report is being made.

In order to provide for or aid in the numerous inferences described herein, the inference component 726 can examine the entirety or a subset of the data to which it is granted access and can provide for reasoning about or infer states of the system (e.g., system 100, 500 and the like), environment, etc. from a set of observations as captured via events and/or data. An inference can be employed to identify a specific context or action, or can generate a probability distribution over states, for example. The inference can be probabilistic—that is, the computation of a probability distribution over states of interest based on a consideration of data and events. An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x4, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

The indexing component 728 can facilitate cleansing, and indexing or organizing the structured diagnostic training data 506 generated by the diagnostic data development component 410 in accordance with one or more defined data models and ontologies to facilitate efficient usage of the structured diagnostic training data 506 for model development and training. In this regard, the indexing component 728 can index and organize marked up medical image data generated by the markup comp 704, the annotated image data generated by the annotation component 706, measurement data generated by the measurement component 708, segmentation data generated by the segmentation component 710, report data generated by the reporting component 712, and in some implementations, relevant data retrieved by the relevant data retrieval component 714, in accordance with a defined data model that relates key data points associated with the respective data sets. In some implementations, the indexing component 728 can further index and associate and correlate the source data (e.g., the unstructured image data, the native image data, etc.), with its structured/annotated counterpart.

The collection component 730 can further collect the data elements, including the structured diagnostic data, an indexed data structured that organized the structured diagnostic data according to a defined data model, and in some implementations, the source data and the relevant data retrieved by the relevant data retrieval component 714, and store them the structured training data database 208. In this regard, the collection component 730 can provide or otherwise facilitate provision of the structured diagnostic training data 506 to one or more machine learning systems of the AI model development system 112, wherein based on reception of the structured diagnostic data, the one or more machine learning systems employ the structured diagnostic training data 506 as training data to generate or train one or more diagnostic models configured to provide AI based diagnostic evaluations of new medical image data.

Figure 8:
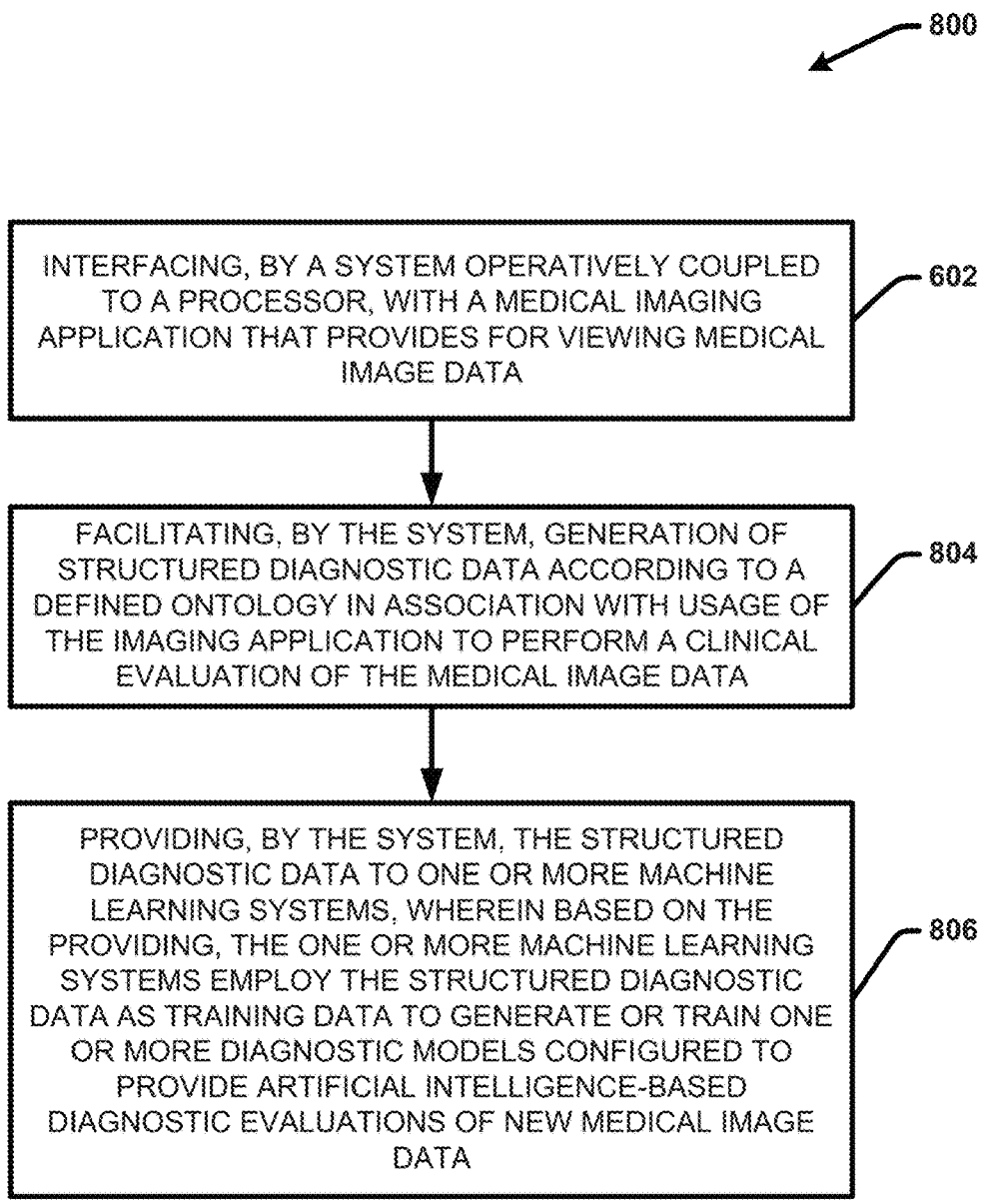
FIG. 8 illustrates flow diagram of an example, non-limiting computer implemented method that facilitates generating one or more diagnostic models in association with integrating AI informatics in healthcare systems using a distributed learning architecture, in accordance with one or more embodiments of the disclosed subject matter.

FIG. 8 illustrates flow diagram of an example, non-limiting computer implemented method 800 that facilitates generating one or more diagnostic models in association with integrating AI informatics in healthcare systems using a distributed learning architecture, in accordance with one or more embodiments of the disclosed subject matter. While, for purposes of simplicity of explanation, the methodologies described herein (e.g., method 800 and additional processes described herein) are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices. Repetitive description of like elements employed in respective embodiments is omitted for sake of brevity.

With reference to FIG. 8, at 802, a system, operatively coupled to a processor (e.g., system 100, system 500 and/or server device 504), interfacing, interfaces with a medical imaging application that provides for viewing medical image data (e.g., imaging/PACS application 406). At 804, the system facilitates generation of structured diagnostic data (e.g., structured diagnostic training data 506) according to a defined ontology in association with usage of the imaging application to perform a clinical evaluation of the medical image data. At 806, the system provides the structured diagnostic data (e.g., via the collection component 730 and/or the structured training data database 208) to one or more machine learning systems (e.g., AI diagnostic model development subsystem 508), wherein based on the providing, the one or more machine learning systems employ the structured diagnostic data as training data to generate or train one or more diagnostic models (e.g., diagnostic models 512) configured to provide artificial intelligence-based diagnostic evaluations of new medical image data.

Figure 9:
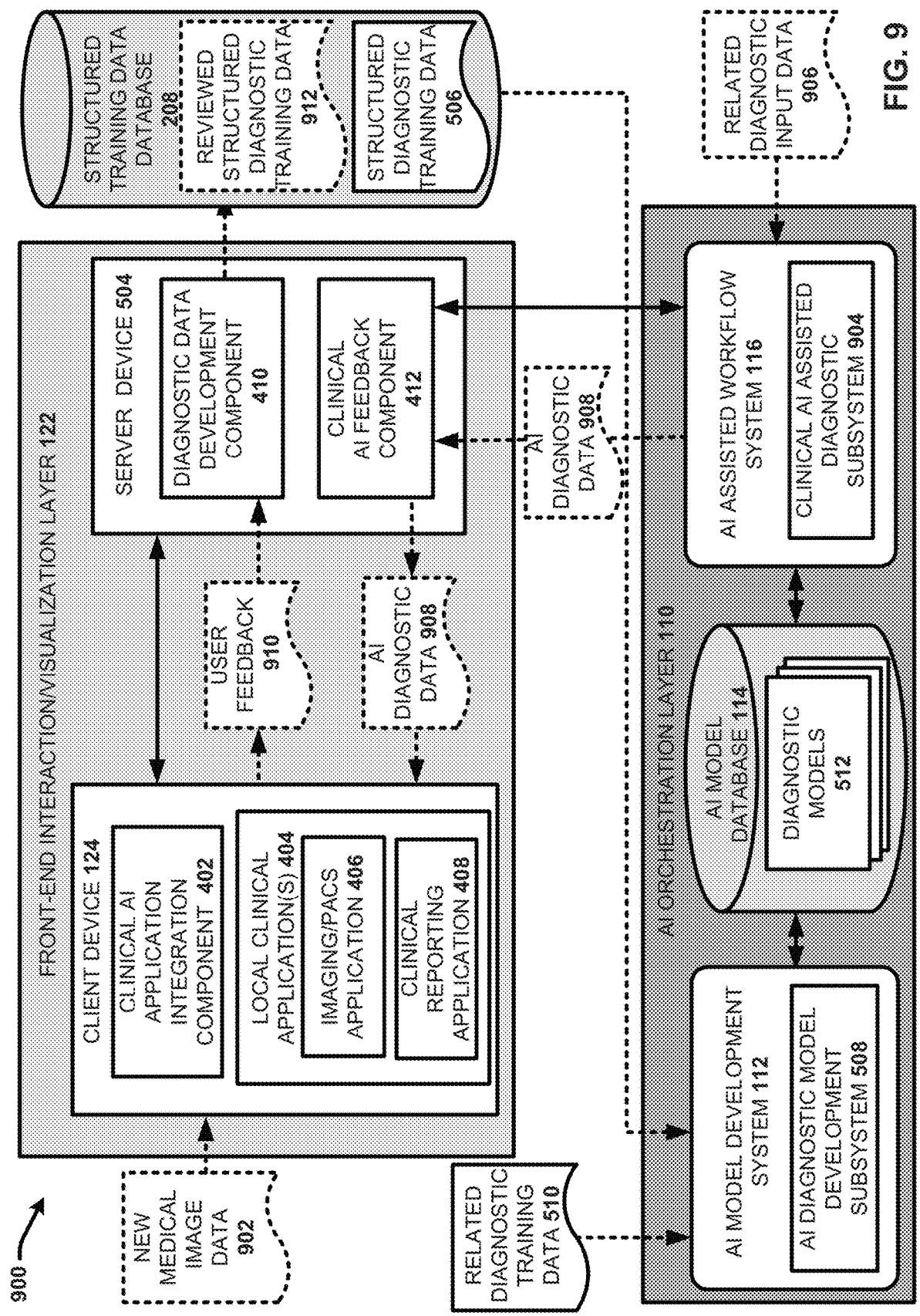
FIG. 9 illustrates a block diagram of an example, non-limiting system that facilitates applying one or more diagnostic models in association with integrating AI informatics in healthcare systems using a distributed learning architecture, in accordance with one or more embodiments of the disclosed subject matter.

FIG. 9 illustrates a block diagram of an example, non-limiting system 900 that facilitates applying one or more diagnostic models 112 in association with integrating AI informatics in healthcare systems using a distributed learning architecture, in accordance with one or more embodiments of the disclosed subject matter. In various embodiments, system 900 is a subsystem of system 100. In this regard, system 100 can include system 900 and vice versa. Various elements of system 100 (e.g., the back-end integration layer 102) are removed from system 900 merely to enable a more focused description of system 100 in association with implementation of system 100 to generate reviewed structured diagnostic training data (e.g., structured diagnostic training data 912). Thus, system 900 can include one or more elements of system 100 that are not shown in system 900 (and vice versa). Repetitive description of like elements employed in respective embodiments is omitted for sake of brevity.

System 900 presents an example embodiment of system 100 in association with application of system 100 to facilitate generating structured diagnostic training data 912 based in part on evaluation of new medical image data 902 by physicians during routine clinical practice. In this context, the medical image data is referred to as "new" medical image data to indicate that it was not seen by or otherwise used by the machine learning algorithms in association with training and development to the diagnostic models 112. In this regard, after initial development and training of the diagnostic models 112 based on the structured diagnostic training data 506, and in various implementations, related diagnostic data 510, the AI workflow assistance system 116 can facilitate integrating and applying the diagnostic models into clinical workflows that involve evaluating new medical image data for a patient (e.g., new medical image data 902). For example, in various embodiments, the AI workflow assistance system 116 can facilitate integrating and applying the diagnostic models 112 in association with usage of the imaging/PACS application 406 and/or the clinical reporting application 408, or similar applications, by physicians in association with interpreting the new medical image data 902 for patients and generating medical reports based in part on their interpretations.

As discussed above with reference to FIG. 3, in some embodiments, the AI workflow assistance system 116 can include a plurality of different AI workflow assistance subsystems that can respectively provide clinical decision support in various healthcare domains and contexts. In this regard, in the embodiment shown, the AI workflow assistance system 116 can include a clinical AI assisted diagnostic subsystem 904 that can be specifically configured provide clinical decision support associated with workflows that involve generating and/or employing information regarding a diagnostic interpretation of a patient. For example, in various example implementations described herein, the clinical AI assisted diagnostic subsystem 904 can be configured to facilitate workflows that involve evaluating medical image data to generate diagnostic information based on the image data (e.g., workflows that involve usage of the imaging/PACS application 406, the clinical reporting application 408, or other relevant applications). In various embodiments, the clinical AI assisted diagnostic subsystem 904 can also be configured to facilitate providing diagnostic interpretational information in association with clinical workflows based on other input data, such as but not limited to, patient laboratory data, monitored patient data such as vital signs and symptoms (e.g., patient data 238), patient omics data, patient health history data, and the like. In this regard, although the following description of system 900 involves a use case wherein diagnostic data is generated based at least in part on medical image data being evaluated and wherein the diagnostic data is provided to clinicians in association with their usage of the imaging/PACS application and/or clinical reporting application 408, it should be appreciated that features and functionalities of system 900 can be applied to generate other types of clinical and/or operational inferences for provision to suitable entities via various means in association with their performance of clinical and/or operational workflows.

In this regard, in one or more embodiments, in association with selecting new medical image data 902 for reviewing using the imaging/PACS application 406, the clinical AI application integration component 402 can facilitate providing the new medical image data 902 to the clinical AI assisted diagnostic subsystem 904. Alternatively, the clinical AI application integration component 402 can facilitate informing the clinical AI assisted diagnostic subsystem 904 what new medical image data 902 has been selected for reviewing and/or is currently being viewed (e.g., via one or more identifiers for the medical image data), and the clinical AI assisted diagnostic subsystem 904 can retrieve or otherwise access a copy of the medical image data provided in one or more medical image data stores or caches (e.g., of the back-end integration layer 102). For example, in the embodiment shown, the server device 504, or more particularly, the clinical AI feedback component 412 can monitor usage of the imaging/PACS application 406 to identify and extract information regarding the new medical image data 902 selected for review and/or currently being viewed. In some implementations, the server device 504 and/or the clinical AI feedback component 412 can further operate as an information relay to the clinical AI assisted diagnostic subsystem 904 and provide the clinical AI assisted diagnostic subsystem 904 with the new medical image data and/or information identifying the new medical image data 902. In other embodiments, one or more features and functionalities of the clinical AI feedback component 412 and/or the clinical AI assisted diagnostic subsystem 904 can be combined at a single device (e.g., the server device 504 or another suitable device). For example, the clinical AI feedback component 412 can include one or more components of the clinical AI assisted diagnostic subsystem 904, or vice versa.

Based on reception of the new medical image data 902 or information identifying the new medical image data 902 the clinical AI assisted diagnostic subsystem 904 can select and apply one or more appropriate diagnostic models 112 to the new medical image data 902 to generate AI diagnostic data 908, which can represent the results or output of the one or more diagnostic models 112. In various implementations, the diagnostic models 112 can be configured to evaluate related diagnostic input data (e.g., related diagnostic input data 906) in association with the new medical image data 902 to generate the AI diagnostic data 908. For example, the related diagnostic input data 906 can include raw image data associated with the new medical image data 902 (e.g., pixel data, waveform data, etc.), patient medical history data, laboratory data, omics data, monitored physiological data, reported signs/symptoms, etc. With these implementations, based on reception of the new medical image data 902 and/or information identifying the new medical image data 902 selected for viewing, the clinical AI assisted diagnostic subsystem 904 can be configured to further identify and retrieve the related diagnostic input data 906 from one or more data sources/systems (e.g., of the back-end integration layer 102) for input to the one or more diagnostic models 112.

The type of results that are generated by diagnostic models 112 can vary based on the configuration of the respective diagnostic models. For example, in some implementations, the AI diagnostic data 908 can include information that provides information regarding a diagnostic interpretation of a medical condition of the patient reflected by the new medical image data. In other implementations, the AI diagnostic data 908 can include information that identifies and/or characterizes defined features reflected in the medical image data (e.g., identified lesions, fractures, anatomical features, inflamed anatomical features, etc.).

The clinical AI assisted diagnostic subsystem 904 can further provide the AI diagnostic data 908 to the imaging/PACS application and/or the clinical reporting application 408 for provision to the physician (e.g., radiologist) in association with usage of the respective applications. For example, in the embodiment shown, the clinical AI assisted diagnostic subsystem 904 can provide the AI diagnostic data 908 to the clinical AI feedback component 412. The clinical AI feedback component 412 can further facilitate integrating the AI diagnostic data 908 into the workflow usage of the local clinical applications 404 via the clinical AI application integration component 402.

The manner in which the AI diagnostic data 908 is provided to the interpreting physician via the imaging/PACS application 406 and/or the clinical reporting application 408 can vary. For example, in some implementations in which the AI diagnostic data 908 comprises a textual, diagnostic description of a patient condition, the AI diagnostic data 908 can be configured for rendering by the imaging/PACS application 406 and/or the clinical reporting application 408 via a pop-up display window, via a notification, in response to selection of a graphical feature notifying the physician that an automated diagnostic, and the like. In other implementations, the AI diagnostic data 908 can be configured to be overlaid onto medical image data being viewed in a GUI. For example, in some implementations, the AI diagnostic data 908 can identify a specific feature in the medical image data and be associated with metadata that defines the location and dimension of the feature within the image data. With these implementations, the imaging/PACS application 406 can be configured to overlay a graphical or visual marking onto the image to identify the feature and/or the dimensions of the feature. In other implementation, the AI diagnostic data 908 can include a copy of the image data with visual artifacts or markings applied thereto that visual identifies or call out the feature of interest (e.g., with a highlighted or distinguishable color, as segmented or separated from the original image, etc.). With this implementation, the imaging/PACS application 406 can be configured to render the copy of the image data with the visual artifacts or markings applied thereto.

System 900 further provides for receiving feedback (e.g., user feedback 910 from the interpreting physician based on the provided AI diagnostic data 908. In particular, the clinical AI feedback component 412 and the clinical AI application integration component 402 can facilitate prompting the interpreting physician to provide some form of review of the AI diagnostic data regarding the accuracy of the AI diagnostic data 908. For example, in one implementation, the clinical AI feedback component 412 and the clinical AI application integration component 402 can prompt the physician to provide binary feedback indicating whether the AI diagnostic data 908 is correct or incorrect (e.g., yes or no). In another implementation, the clinical AI feedback component 412 and the clinical AI application integration component 402 can facilitate receiving user defined score that represents a personal interpretation of the level of accuracy of the AI diagnostic data 908. In another example, the clinical AI feedback component 412 and the clinical AI application integration component 402 can facilitate receiving feedback that describes in detail, whether and how the AI diagnostic data 908 is correct or incurred. For example, in some implementations, the physician can further annotate and/or mark up the medical image data with information that changes one or more aspects of the AI diagnostic data 908 to correct the diagnostic data.

In some embodiments, in association with generating a medical report based on the AI diagnostic data, if the physician accepts the AI diagnostic interpretation as accurate, the AI diagnostic data can be automatically integrated into or otherwise added to the medical report.

The clinical AI application integration component 402 can further provide the user feedback to the diagnostic data development component 410 for generating the structured diagnostic training data 912. In this regard, the diagnostic data development component 410 can associate the new medical image data with the user feedback 910 to generate the structured diagnostic training data 912. The structured diagnostic training data 912 can thus for example, include new medical image data with automated annotations, markings/and text data that was generated by one or more diagnostic models and accepted as correct. The structured diagnostic training data 912 can also include for example, include the new medical image data with information (e.g., annotations, mark-ups, text data, etc.) that was applied or provided by the clinician that accurately interprets a medical image by discarding or modifying the AI diagnostic data. In this regard, the structured diagnostic training data 912 can include evidence based validated and corrected training data that can be regularly generated over the course of routing usage of the imaging/PACS application 406 and/or the clinical reporting application.

The structured diagnostic training data 912 can further be provided to and/or retrieved by the clinical AI model development subsystem to regularly update and/or optimize the diagnostic models 112. In this regard, system 900 provides an optimization cycle for regularly receiving new training data that provides information regarding new coefficients/model parameters or identifies errors in previously set coefficients/model parameters that can be used to further adapt, train, and improve model performance.

Figure 10:
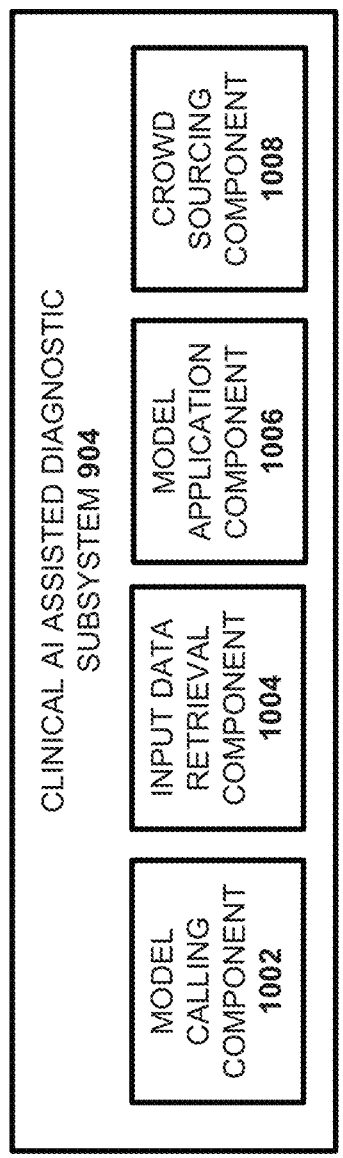
FIG. 10 illustrates a block diagram of an example, clinical AI assisted diagnostic subsystem that facilitates applying one or more diagnostic models in association with integrating AI informatics in healthcare systems using a distributed learning architecture, in accordance with one or more embodiments of the disclosed subject matter.

FIG. 10 illustrates a block diagram of an example, clinical AI assisted diagnostic subsystem 904 that facilitates applying one or more diagnostic models in association with integrating AI informatics in healthcare systems using a distributed learning architecture, in accordance with one or more embodiments of the disclosed subject matter.

In the embodiment shown, the clinical AI assisted diagnostic subsystem 904 can include model calling component 1002, input data retrieval component 1104, model application component 1106 and crowd sourcing component. As discussed infra, in various embodiments, the AI models included in the AI model database 114 can be tailed to different medical domains, data sets and the like and have different levels of granularity. For example, within a single domain such as the medical imaging domain for example, different models can be tailored to different image data types, different conditions, different body parts, different functions (e.g., identifying features with specific characteristics or diagnosis a condition based on the features and other patient related data, etc.). In this regard, the model calling component 1002 can be configured to parse the respective models included in the database to identify and call the appropriate model or models that can be applied to a current data set/patient being evaluated. For example, based on the image data set being evaluated, the type of the data (e.g., a non-contrast CT scan or a CT angiography data set, or an MRI), the model calling component 1002 can select one or more applicable models for applying to the data set to generate the AI diagnostic data 908.

In various embodiments, image data can be used as only partial input to the selected data models. In this regard, various types of related diagnostic input data 906 can be used as input to the respective models that is related to the image data set being evaluated. Accordingly, the input data retrieval component 1004 can be configured to identify and retrieve the necessary input data for the selected diagnostic model from various data sources included in the back-end integration layer 102. For example, based on an image data set selected for review, the input data retrieval component 1004 can identify the patient and other relevant data associated with the patient included in the patient's EHR. In another example, based on the image data set selected for review, the input data retrieval component 1004 can retrieve the image data set, retrieve raw image data associated with the image data set and the like.

The model application component 1006 can be configured to apply the one or more selected diagnostic models to the input data (e.g., the image data and/or the related diagnostic input data 906) to generate the related diagnostic input data 906.

The crowd sourcing component 1008 can provide one or more additional feature associated with generating a crowd sourced interpretation of medical image data in real-time. For example, in some implementations in which a radiologist is provided with AI diagnostic data 908, the radiologist may not be confident with either accepting or rejecting the results. According to this example, the crowd sourcing component 1008 can facilitate presenting the image data and associated AI diagnostic data to a plurality of specialists, radiologists, etc., in real-time or sustainably real-time to receive their opinion of the AI diagnostic results. Their polled opinions can be presented to the immediate radiologist to facilitate his or her review of the AI diagnostic results. The polled opinion data can also be associated with the image data to facilitate training and updating the models.

In another embodiment, one or more diagnostic models 112 can be configured to generate diagnostic information associated with a score that represents a degree of confidence in the results. For example, a diagnostic algorithm can be configured to evaluate tumors to determine a score for the tumor that represents a degree of confidence that is malignant or not (e.g., 90% confidant this tumor is malignant). In accordance with this embodiment, the crowd sourcing component 1008 can be configured to initiate a poll to a group of specialists to receive their opinion on the diagnostic interpretation when the confidence score associated with the interpretation is less than a defined threshold (e.g., less than 100%, less than 90%, etc.). The poll can allow the specialists to provide their interpretation of the AI results and the image data. The polled results can further be provided to the interpreting clinician along with the AI results, and/or the AI results can be adjusted based on the polled opinions.

Figure 11:
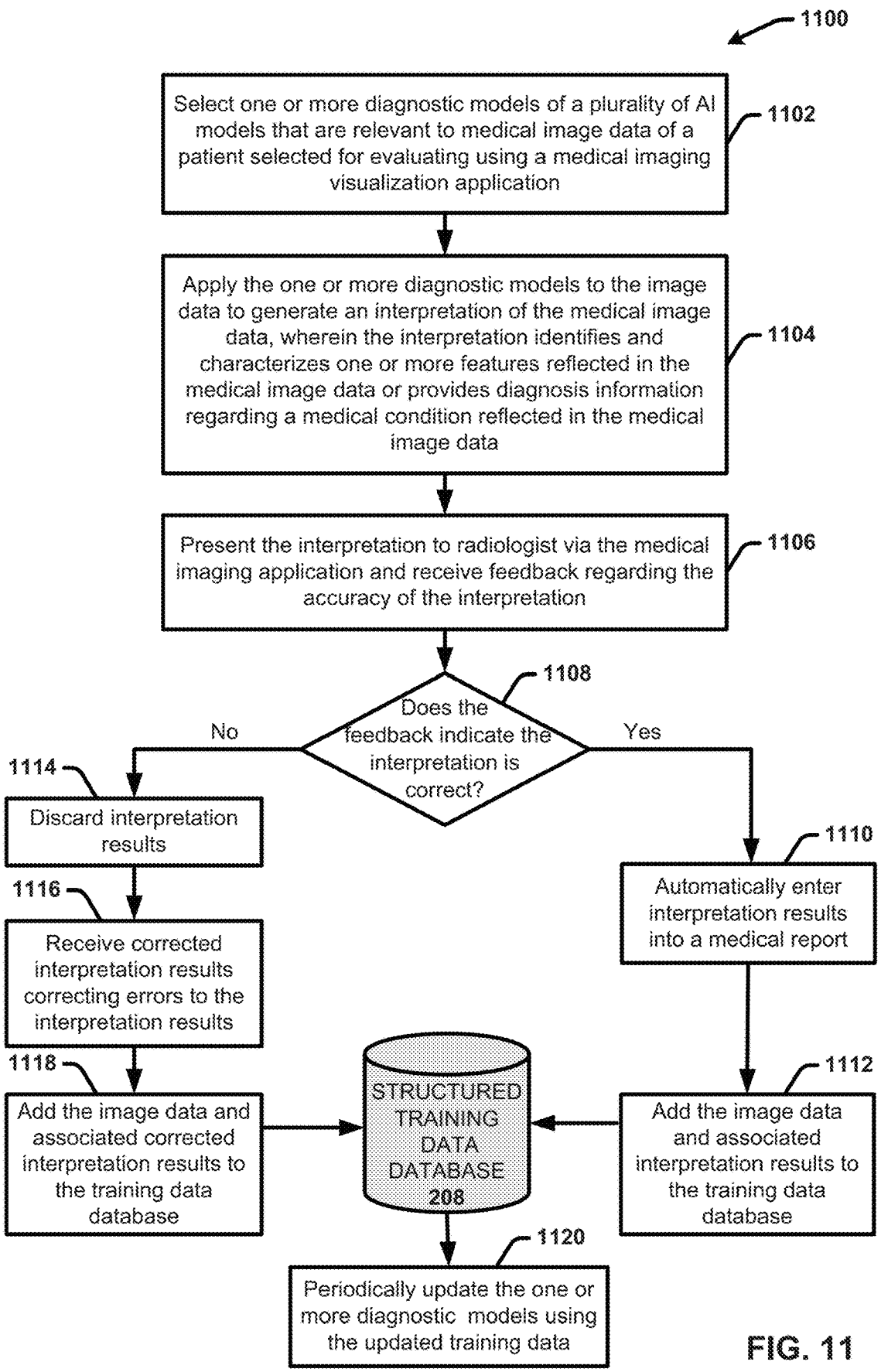
FIG. 11 illustrates a block diagram of an example, non-limiting computer implemented method that that facilitates applying one or more diagnostic models in association with integrating AI informatics in healthcare systems using a distributed learning architecture, in accordance with one or more embodiments of the disclosed subject matter.

FIG. 11 illustrates a block diagram of an example, non-limiting computer implemented method 1100 that that facilitates applying one or more diagnostic models in association with integrating AI informatics in healthcare systems using a distributed learning architecture, in accordance with one or more embodiments of the disclosed subject matter. Repetitive description of like elements employed in respective embodiments is omitted for sake of brevity.

At 1102, one or more diagnostic models of a plurality of AI models (e.g., included in the AI healthcare model database 1114) are selected that are relevant to medical image data of a patient selected for evaluating using a medical imaging visualization application (e.g., imaging/PACS application 406). At 1104, the one or more diagnostic models are applied to the image data to generate an interpretation of the medical image data, wherein the interpretation identifies and characterizes one or more features reflected in the medical image data or provides diagnosis information regarding a medical condition reflected in the medical image data. At 1106, the interpretation is presented to radiologist via the medical imaging application and feedback is received regarding the accuracy of the interpretation.

At 1108, if the feedback indicates the interpretation is correct, then method 1100 can continue to 1110, and interpretation results can be automatically entered into a medical report (e.g., a medical report generated using the clinical reporting application 408, an automated medical report generated without human input, or another suitable medical report). Then at 1112 the image data and associated interpretation results can be added to the training data database (e.g., the structured straining data database). At 1120, the new training data and/or aggregated training data included in the structured training data database 208 can be used to periodically update the one or more diagnostic models. However, if at 1108, the feedback indicates the interpretation is incorrect, at 1114, the interpretation results can be discarded (or partially discarded to remove only the portions of the results that are incorrect). Then at 1116, corrected interpretation results can be received that correct the errors in the AI based interpretation results. At 1118, the image data and the associated corrected interpretation results can then be added to the training data database and used to periodically update the one or more diagnostic models at 1120.

FIGS. 12A-12D present medical imaging visualizations generated in association with integration of one or more AI diagnostic models with a medical imaging application in accordance with one or more embodiments of the disclosed subject matter. In various embodiments, the medical imaging visualization presented in FIGS. 12A-12D can be generated by the imaging/PACS application 406 (or a similar application) in association with integration, via the clinical AI application integration component 402, of the features and functionalities provided by the clinical AI feedback component 412 and the clinical AI assisted diagnostic subsystem 904, in accordance with the techniques described herein. Repetitive description of like elements employed in respective embodiments is omitted for sake of brevity.

Figure 12A:
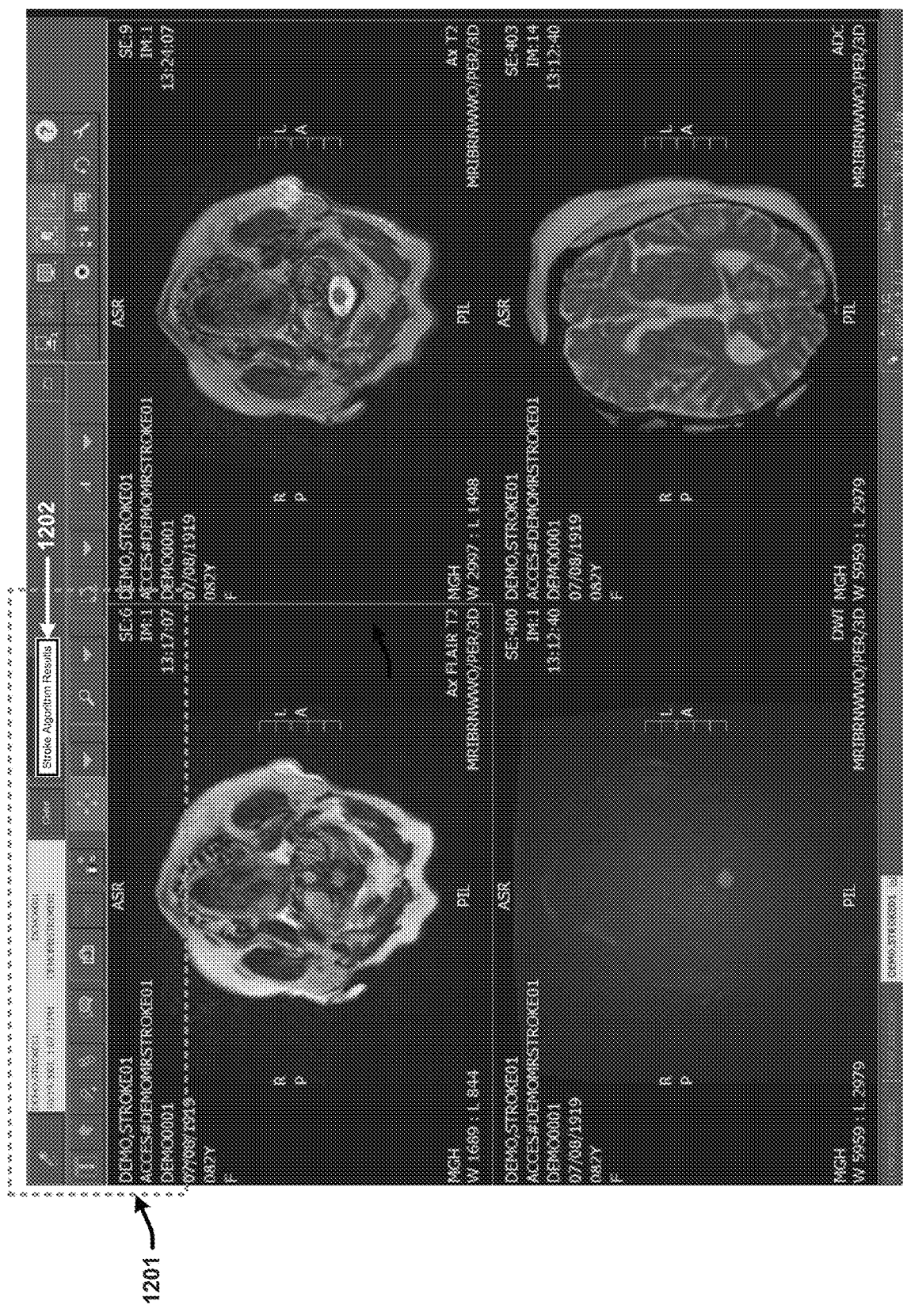
FIGS. 12A-12D present medical imaging visualizations generated in association with integration of one or more AI diagnostic models with a medical imaging application in accordance with one or more embodiments of the disclosed subject matter.
Figure 12B:
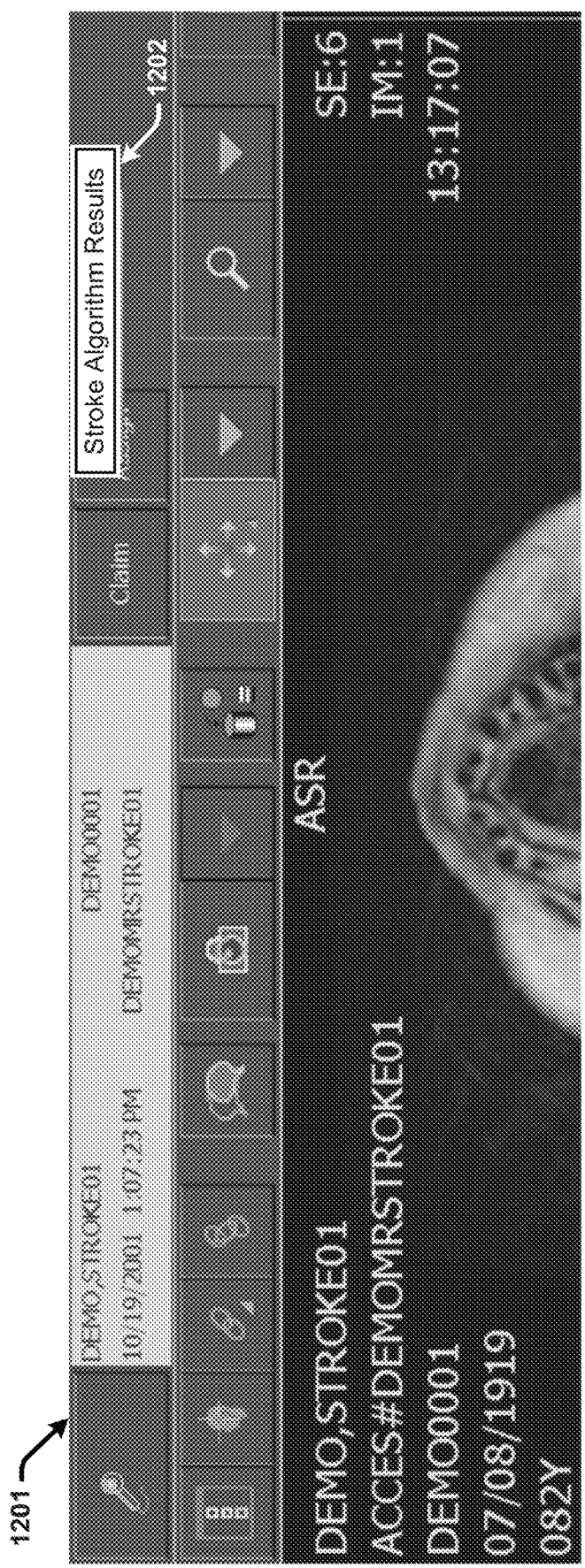
Figure 12C:
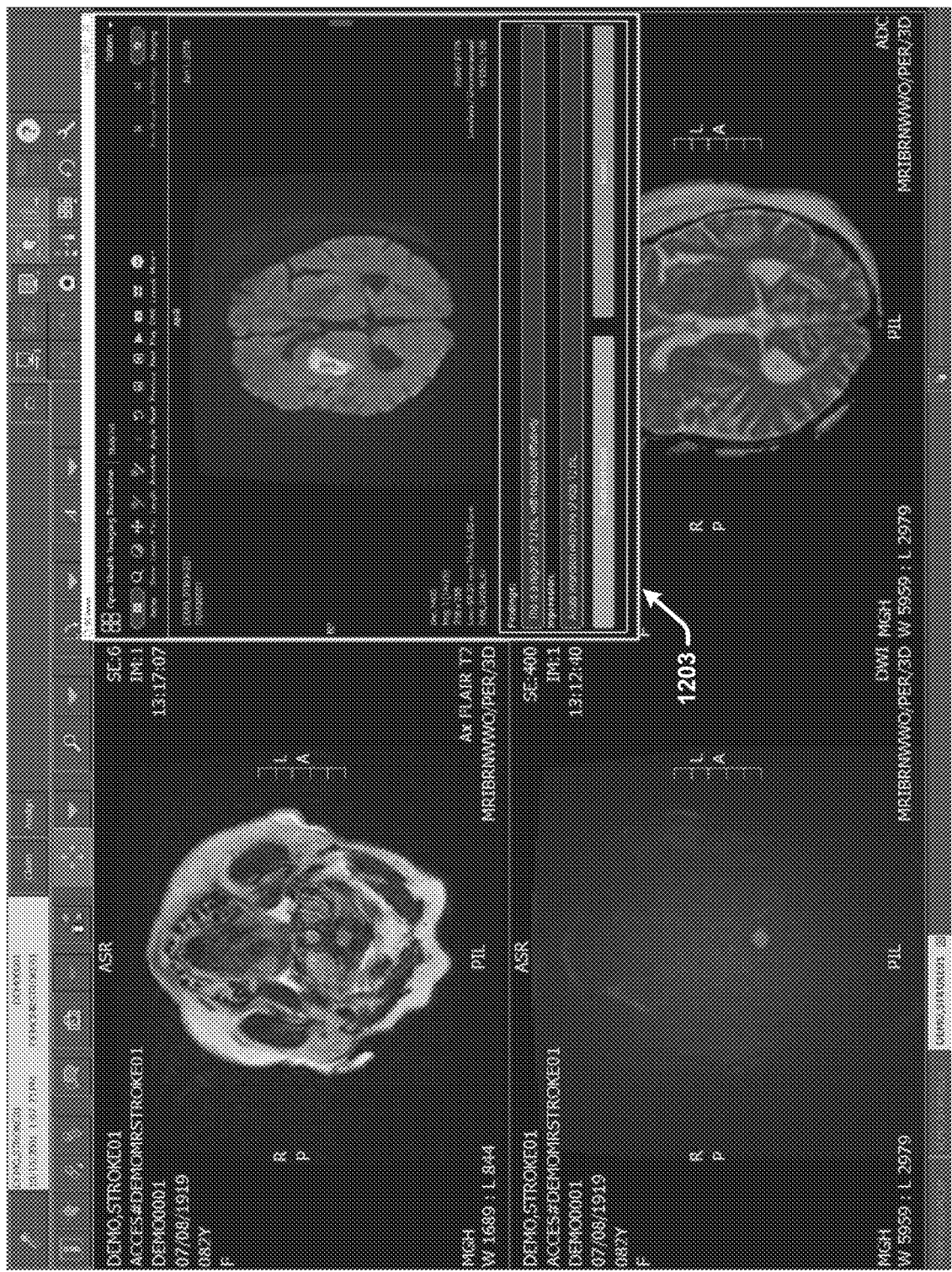
Figure 12D:
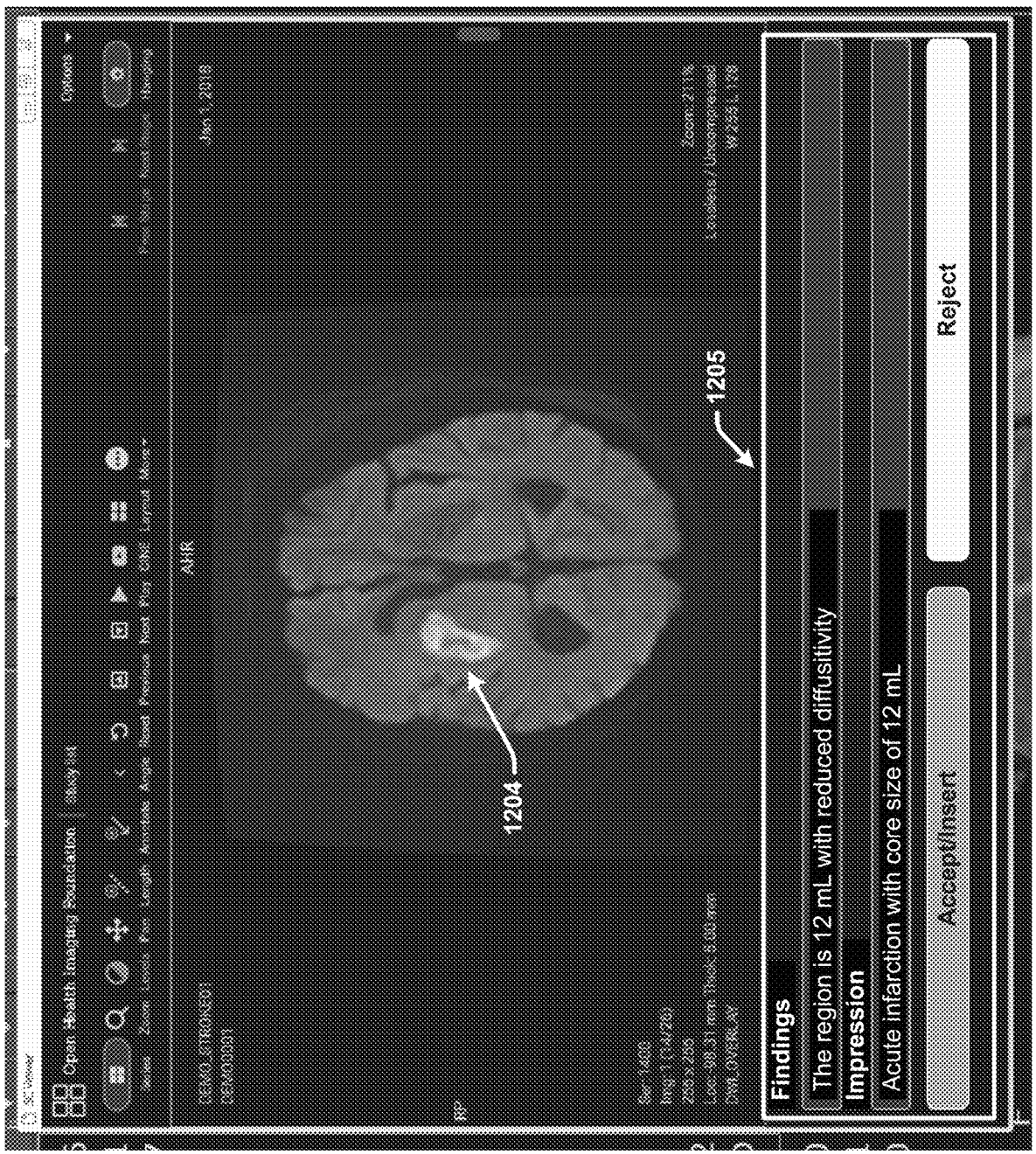

With reference initially to FIG. 12A, presented is an example visualization comprising several different MRI views of a patient MRI brain scan are presented in different windows for viewing by the physician, the visualization presented in FIG. 12A is identical to that presented in FIG. 6, with the addition of a notification message 1202 presented in the upper toolbar of the GUI. FIG. 12B presents an enlarged view of the region of visualization within dashed box 1201 including the notification message 1202. As shown in FIG. 12.B, the notification message 1202 indicates that stroke algorithm results are available. For example, in various embodiments, the notification message 1202 can be generated in response to application (e.g., via the clinical AI assisted diagnostic subsystem 904) of a diagnostic model (e.g., one or more of the diagnostic models 512) to the medical image data set being viewed that is configured to evaluate brain MRI scan data to identify and characterize features indicative of a stroke. In the example, implantation, the notification message 1202 can be selected to view or otherwise receive the results of the stroke algorithms FIG. 12C presents an example view of an example pop-up display window 1203 that can be generated (e.g., via the clinical AI assisted diagnostic subsystem 904, the clinical AI feedback component 412 and/or the imaging/PACS application 406), and overlaid (e.g., via the clinical AI application integration component 402 and/or the imaging/PACS application) onto the previous visualization in response to selection of the notification message 1202. FIG. 12D presents an enlarged view of the pop-up display window 1203. As shown in FIG. 12D, the AI diagnostic results of the stroke algorithm can comprise image data that visually identifies a feature of interest 1204 present in (one or more) of the medical images by highlighting, presenting in a different color, or otherwise visually marking the feature of interest 1204. The results of the stroke algorithm can further include text data describing one or more characteristics of the feature of interests. For example, as presented in dialogue box 1205, a description of the "findings" and an "impression" of the findings is presented. In this regard, the findings indicate that a region (e.g., feature of interest 1204) having a volume of 12 mL with reduced diffusivity was identified. The impression indicates that the region is an acute infraction with a core size of 12 mL. In the embodiment shown, the radiologist can further choose to accept and insert the results (e.g., insert into a medical report or otherwise associated the results with the image data), or reject the results by selecting the corresponding widgets.

Figure 13:
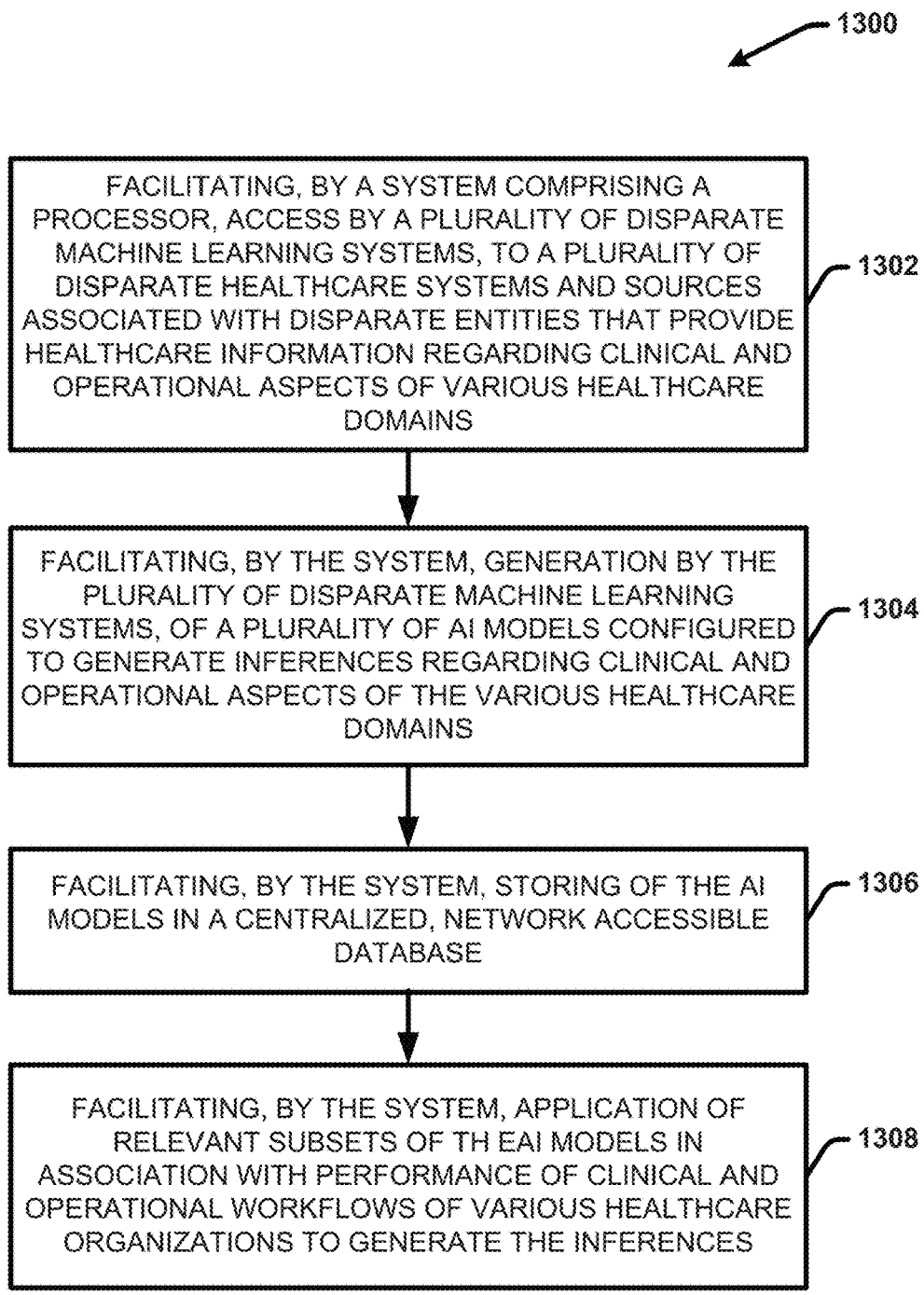
FIG. 13 illustrates a block diagram of an example, non-limiting computer implemented method that facilitates integrating AI informatics in healthcare systems using a distributed learning platform, in accordance with one or more embodiments of the disclosed subject matter.

FIG. 13 illustrates a block diagram of an example, non-limiting computer implemented method 1300 that facilitates integrating AI informatics in healthcare systems using a distributed learning platform, in accordance with one or more embodiments of the disclosed subject matter. Repetitive description of like elements employed in respective embodiments is omitted for sake of brevity.

At 1302, a system comprising a processor (e.g., system 100, system 500, system 900 and the like) facilitates (e.g., via the AI orchestration layer 110), access by a plurality of disparate machine learning systems (e.g., included in the AI model development system 112), to a plurality of disparate healthcare systems and sources (e.g., provided by the back-end integration layer 102, the consortium datastore 130, the health cloud 132 and the like) associated with disparate entities and that provide healthcare information regarding clinical and operational aspects of various healthcare domains. At 1304, the system facilitates (e.g., via the AI orchestration layer 110), generation by the plurality of disparate machine learning systems, of a plurality of AI models (e.g., diagnostic models 112 as well as other types of AI models that can included in the AI model database 114) configured to generate inferences regarding clinical and operational aspects of the various healthcare domains. At 1306, the system facilitates (e.g., via the AI orchestration layer 110), storing of the AI models in a centralized, network accessible database (e.g., the AI model database 114). At 1308, the system further facilitates (e.g., via the AI orchestration layer 110), application of relevant subsets of the AI models in association with performance of clinical and operational workflows of various healthcare organizations to generate the inferences (e.g., via the AI workflow assistance system 116 and associated subsystems).

Figure 14:
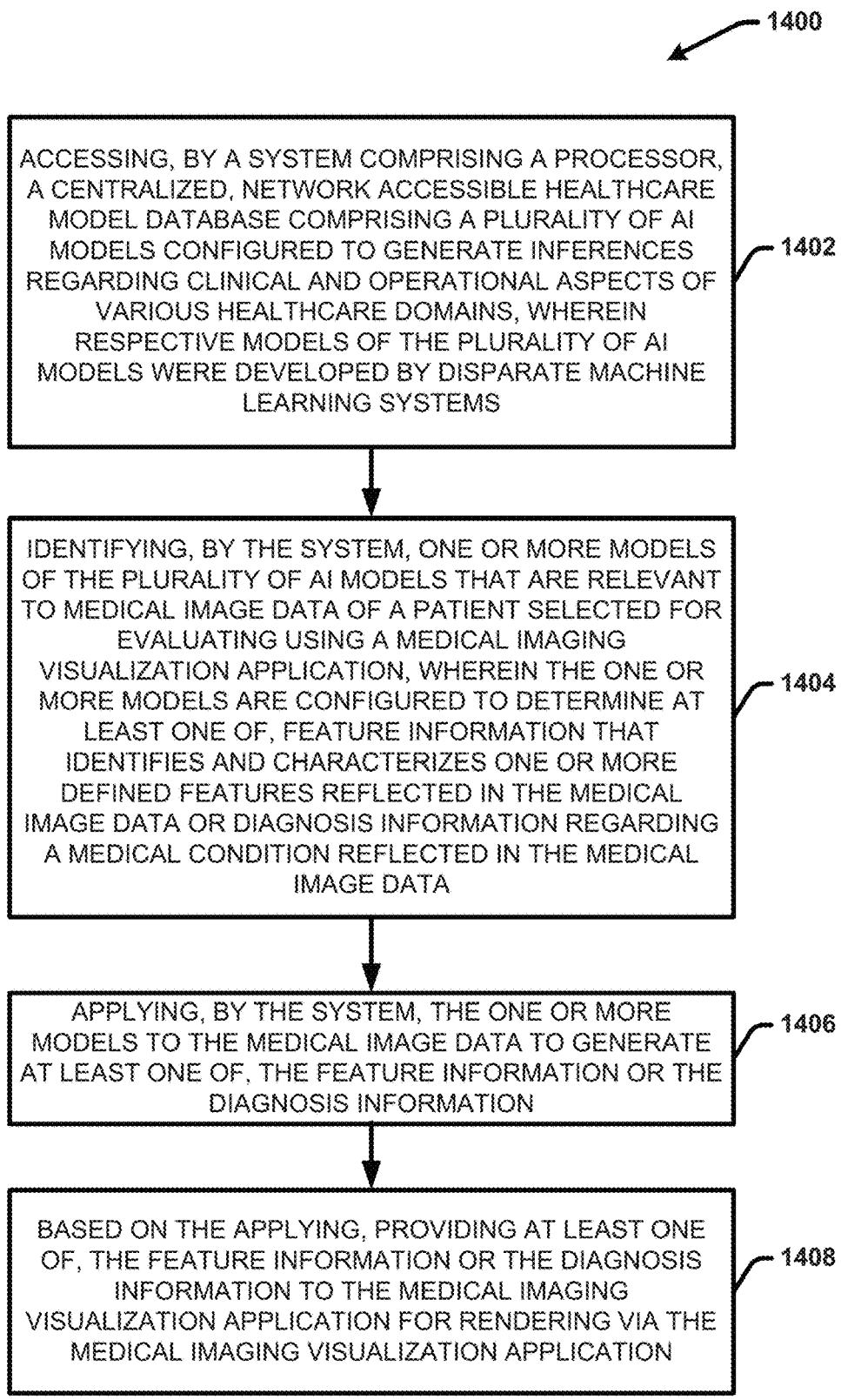
FIG. 14 illustrates a block diagram of another example, non-limiting computer implemented method that that facilitates applying one or more diagnostic models in association with integrating AI informatics in healthcare systems using a distributed learning architecture, in accordance with one or more embodiments of the disclosed subject matter.

FIG. 14 illustrates a block diagram of another example, non-limiting computer implemented method 1400 that that facilitates applying one or more diagnostic models in association with integrating AI informatics in healthcare systems using a distributed learning architecture, in accordance with one or more embodiments of the disclosed subject matter. Repetitive description of like elements employed in respective embodiments is omitted for sake of brevity.

At 1402, a system comprising a processor accesses a centralized, network accessible healthcare model database (e.g., AI model database 114) comprising a plurality of AI models configured to generate inferences regarding clinical and operational aspects of various healthcare domains, wherein respective models of the plurality of AI models were developed by disparate machine learning systems (e.g., of the AI model development system 112). At 1404, the system identifies (e.g., via the model calling component 1002) one or more models of the plurality of AI models that are relevant to medical image data of a patient selected for evaluating using a medical imaging visualization application (e.g., via imaging/PACS application 406), wherein the one or more models are configured to determine at least one of, feature information that identifies and characterizes one or more defined features reflected in the medical image data or diagnosis information regarding a medical condition reflected in the medical image data. For example, the model calling component 1002 can select one or more diagnostic models 512 based on a type of the image data, an area of the body represented in the image data, a potential medical condition that could be reflected in the image data, etc. At 1406, the system applies the one or more models to the medical image data to generate at least one of, the feature information or the diagnosis information (e.g., via the model application component 1006). At 1408, based on the applying, the system provides at least one of, the feature information or the diagnosis information (e.g., AI diagnostic data 908) to the medical imaging visualization application for rendering via the medical imaging visualization application.

For example, the feature information and/or the diagnosis information can be formatted for rending as text, as graphical overlays onto the medical image identifying, marking and/or describing a feature of interest, or the like.

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 15, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 15:
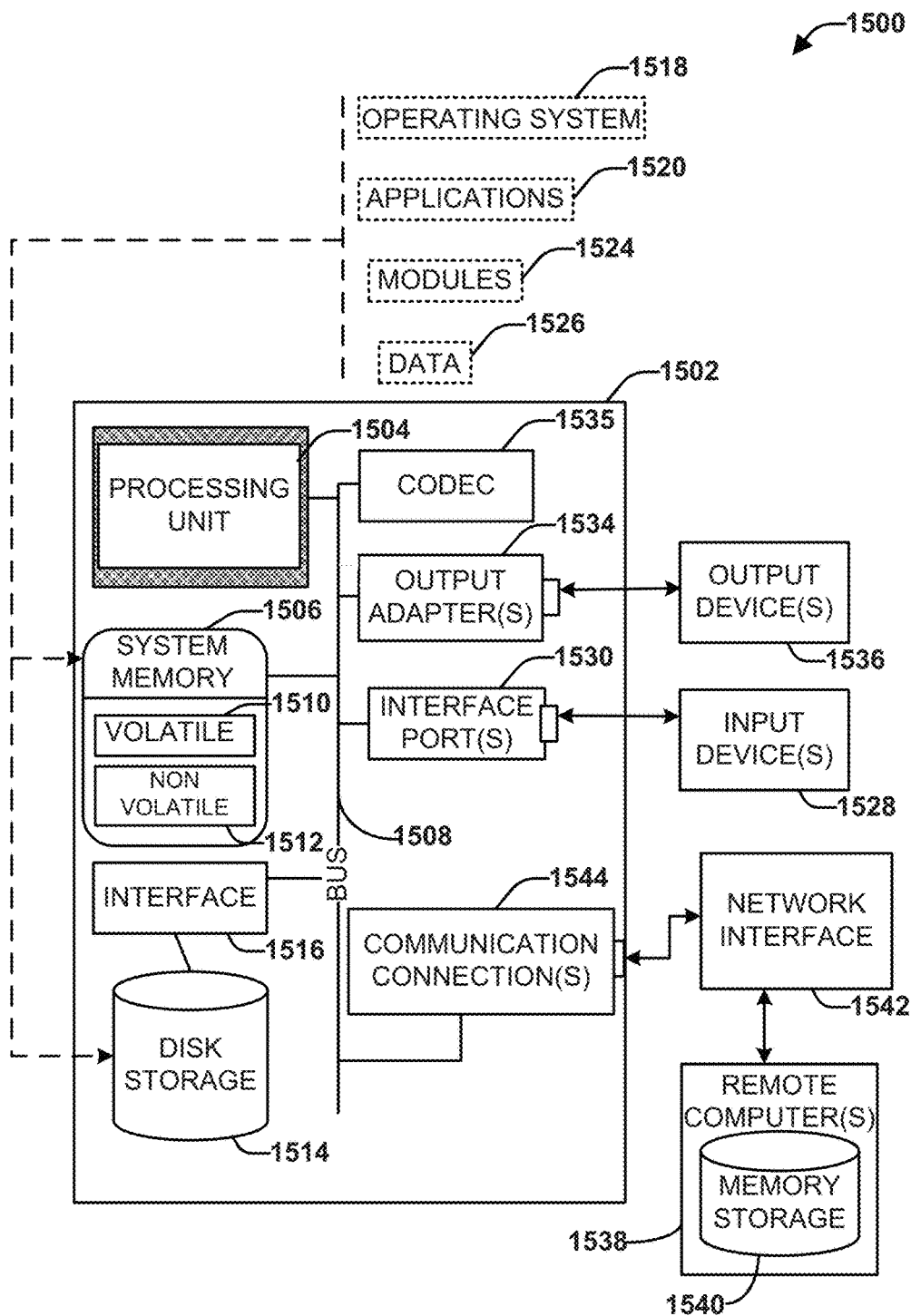
FIG. 15 illustrates a block diagram of an example, non-limiting operating environment in which one or more embodiments described herein can be facilitated.

With reference to FIG. 15, an example environment 1500 for implementing various aspects of the claimed subject matter includes a computer 1502. The computer 1502 includes a processing unit 1504, a system memory 1506, a codec 1535, and a system bus 1508. The system bus 1508 couples system components including, but not limited to, the system memory 1506 to the processing unit 1504. The processing unit 1504 can be any of various available processors. Dual microprocessors and other multiprocessor architectures also can be employed as the processing unit 1504.

The system bus 1508 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13154), and Small Computer Systems Interface (SCSI).

The system memory 1506 includes volatile memory 1510 and non-volatile memory 1512, which can employ one or more of the disclosed memory architectures, in various embodiments. The basic input/output system (BIOS), containing the basic routines to transfer information between elements within the computer 1502, such as during start-up, is stored in non-volatile memory 1512. In addition, according to present innovations, codec 1535 can include at least one of an encoder or decoder, wherein the at least one of an encoder or decoder can consist of hardware, software, or a combination of hardware and software. Although, codec 1535 is depicted as a separate component, codec 1535 can be contained within non-volatile memory 1512. By way of illustration, and not limitation, non-volatile memory 1512 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1512 can employ one or more of the disclosed memory devices, in at least some embodiments. Moreover, non-volatile memory 1512 can be computer memory (e.g., physically integrated with computer 1502 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1510 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1502 can also include removable/non-removable, volatile/non-volatile computer storage medium. FIG. 15 illustrates, for example, disk storage 1514. Disk storage 1514 includes, but is not limited to, devices like a magnetic disk drive, solid state disk (SSD), flash memory card, or memory stick. In addition, disk storage 1514 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1514 to the system bus 1508, a removable or non-removable interface is typically used, such as interface 1516. It is appreciated that disk storage 1514 can store information related to an entity. Such information might be stored at or provided to a server or to an application running on an entity device. In one embodiment, the entity can be notified (e.g., by way of output device(s) 1536) of the types of information that are stored to disk storage 1514 or transmitted to the server or application. The entity can be provided the opportunity to opt-in or opt-out of having such information collected or shared with the server or application (e.g., by way of input from input device(s) 1528).

It is to be appreciated that FIG. 15 describes software that acts as an intermediary between entities and the basic computer resources described in the suitable operating environment 1500. Such software includes an operating system 1518. Operating system 1518, which can be stored on disk storage 1514, acts to control and allocate resources of the computer system 1502. Applications 1520 take advantage of the management of resources by operating system 1518 through program modules 1524, and program data 1526, such as the boot/shutdown transaction table and the like, stored either in system memory 1506 or on disk storage 1514. It is to be appreciated that the claimed subject matter can be implemented with various operating systems or combinations of operating systems.

An entity enters commands or information into the computer 1502 through input device(s) 1528. Input devices 1528 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1504 through the system bus 1508 via interface port(s) 1530. Interface port(s) 1530 include, for example, a serial port, a parallel port, a game port, and a universal serial bus (USB). Output device(s) 1536 use some of the same type of ports as input device(s) 1528. Thus, for example, a USB port can be used to provide input to computer 1502 and to output information from computer 1502 to an output device 1536. Output adapter 1534 is provided to illustrate that there are some output devices 1536 like monitors, speakers, and printers, among other output devices 1536, which require special adapters. The output adapters 1534 include, by way of illustration and not limitation, video and sound cards that provide a means of connection between the output device 1536 and the system bus 1508. It should be noted that other devices or systems of devices provide both input and output capabilities such as remote computer(s) 1538.

Computer 1502 can operate in a networked environment using logical connections to one or more remote computers, such as remote computer(s) 1538. The remote computer(s) 1538 can be a personal computer, a server, a router, a network PC, a workstation, a microprocessor based appliance, a peer device, a smart phone, a tablet, or other network node, and typically includes many of the elements described relative to computer 1502. For purposes of brevity, only a memory storage device 1540 is illustrated with remote computer(s) 1538. Remote computer(s) 1538 is logically connected to computer 1502 through a network interface 1542 and then connected via communication connection(s) 1544. Network interface 1542 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1544 refers to the hardware/software employed to connect the network interface 1542 to the bus 1508. While communication connection 1544 is shown for illustrative clarity inside computer 1502, it can also be external to computer 1502. The hardware/software necessary for connection to the network interface 1542 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 16:
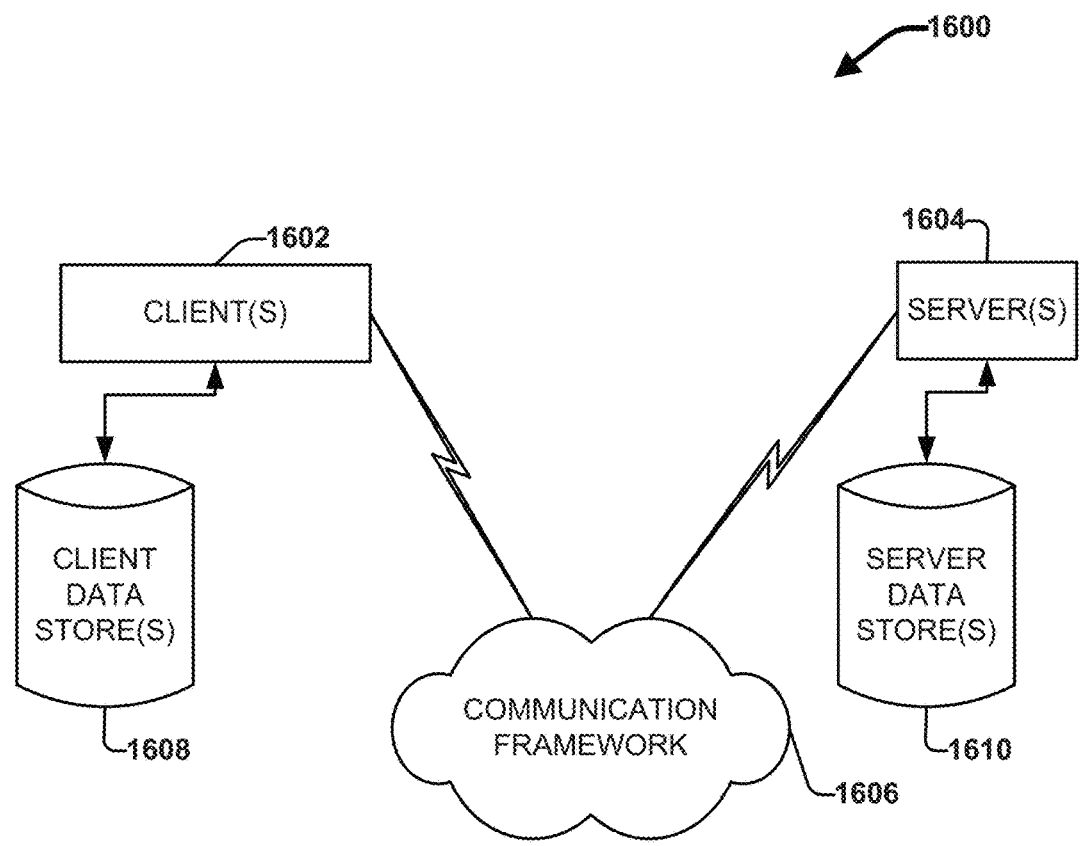
FIG. 16 illustrates a block diagram of another example, non-limiting operating environment in which one or more embodiments described herein can be facilitated.

Referring to FIG. 16, there is illustrated a schematic block diagram of a computing environment 1600 in accordance with this disclosure in which the subject systems (e.g., systems 100, 500, 900 and the like), methods and computer readable media can be deployed. The computing environment 1600 includes one or more client(s) 1602 (e.g., laptops, smart phones, PDAs, media players, computers, portable electronic devices, tablets, and the like). The client(s) 1602 can be hardware and/or software (e.g., threads, processes, computing devices). The computing environment 1600 also includes one or more server(s) 1604. The server(s) 1604 can also be hardware or hardware in combination with software (e.g., threads, processes, computing devices). The servers 1604 can house threads to perform transformations by employing aspects of this disclosure, for example. In various embodiments, one or more components, devices, systems, or subsystems of system 100, 500 and 900, can be deployed as hardware and/or software at a client 1602 and/or as hardware and/or software deployed at a server 1604. One possible communication between a client 1602 and a server 1604 can be in the form of a data packet transmitted between two or more computer processes wherein the data packet may include healthcare related data, training data, AI models, input data for the AI models and the like. The data packet can include a metadata, e.g., associated contextual information, for example. The computing environment 1600 includes a communication framework 1606 (e.g., a global communication network such as the Internet, or mobile network(s)) that can be employed to facilitate communications between the client(s) 1602 and the server(s) 1604.

Communications can be facilitated via a wired (including optical fiber) and/or wireless technology. The client(s) 1602 include or are operatively connected to one or more client data store(s) 1608 that can be employed to store information local to the client(s) 1602 (e.g., associated contextual information). Similarly, the server(s) 1604 are operatively include or are operatively connected to one or more server data store(s) 1610 that can be employed to store information local to the servers 1604.

In one embodiment, a client 1602 can transfer an encoded file, in accordance with the disclosed subject matter, to server 1604. Server 1604 can store the file, decode the file, or transmit the file to another client 1602. It is to be appreciated, that a client 1602 can also transfer uncompressed file to a server 1604 and server 1604 can compress the file in accordance with the disclosed subject matter. Likewise, server 1604 can encode video information and transmit the information via communication framework 1606 to one or more clients 1602.

Figure 17:
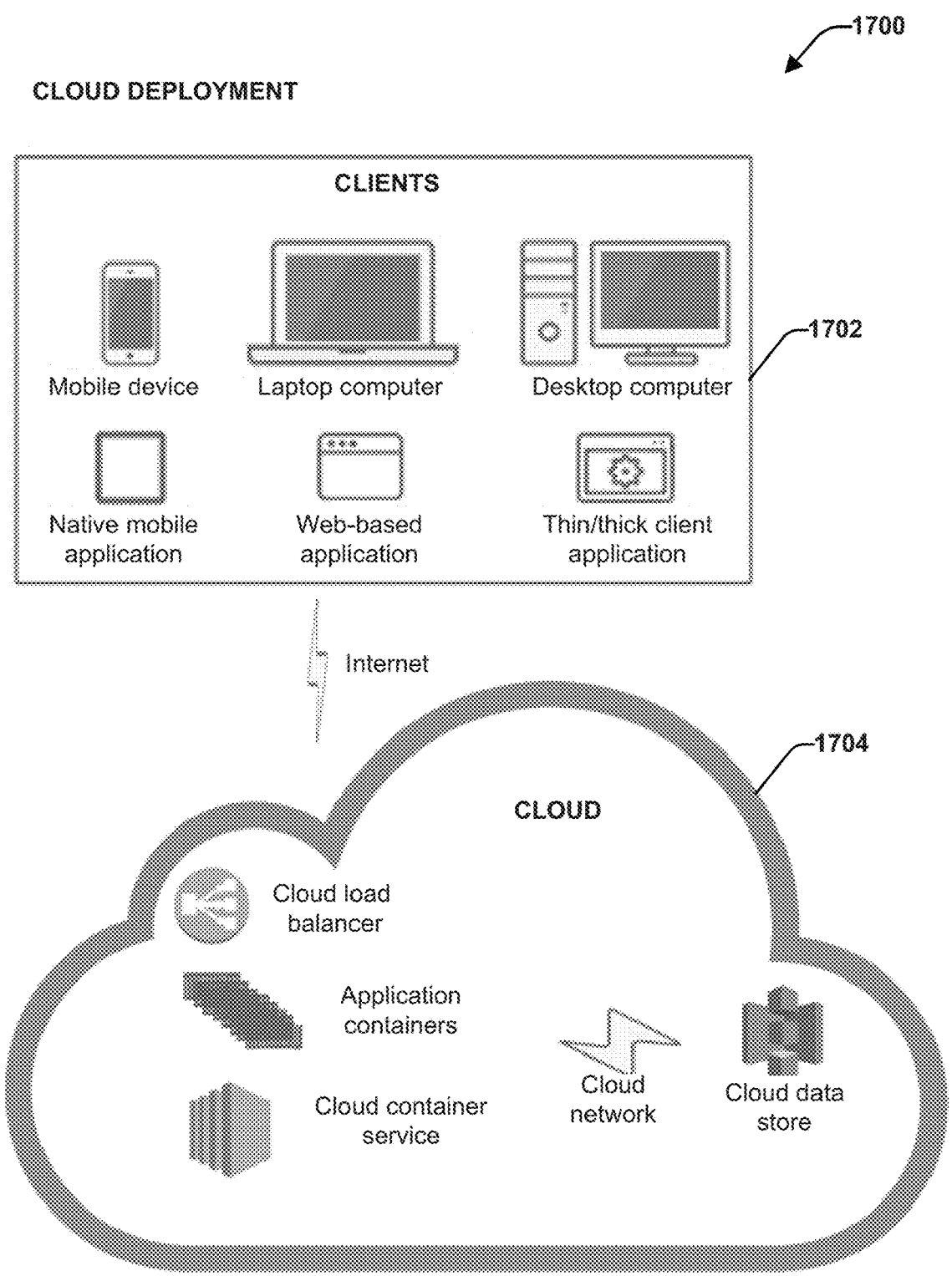
FIG. 17 illustrates a block diagram of another example, non-limiting operating environment in which one or more embodiments described herein can be facilitated.

FIG. 17 illustrates a schematic block diagram of another example computing environment 1700 in accordance with this disclosure in which the subject systems (e.g., systems 100, 500, 900 and the like), methods and computer readable media can be deployed. The computing environment 1700 includes a cloud deployment architecture consisting of one or more clients 1702 that can be communicatively coupled to a system cloud 1704 via a network (e.g., the Internet). The system cloud 1704 can include a cloud load balances, one or more application container, one or more cloud service containers, a cloud data store, and a cloud network that communicatively couples the one or more cloud components to the cloud data store. In accordance with the cloud deployment architecture, the clients 1702 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., system 100, 500, 900 and the like) deployed in the system cloud 1704. In various implementations, the one or more components of systems 100, 500 and/or 900 can be distributed between the clients 1702 and the system cloud 1704.

Figure 18:
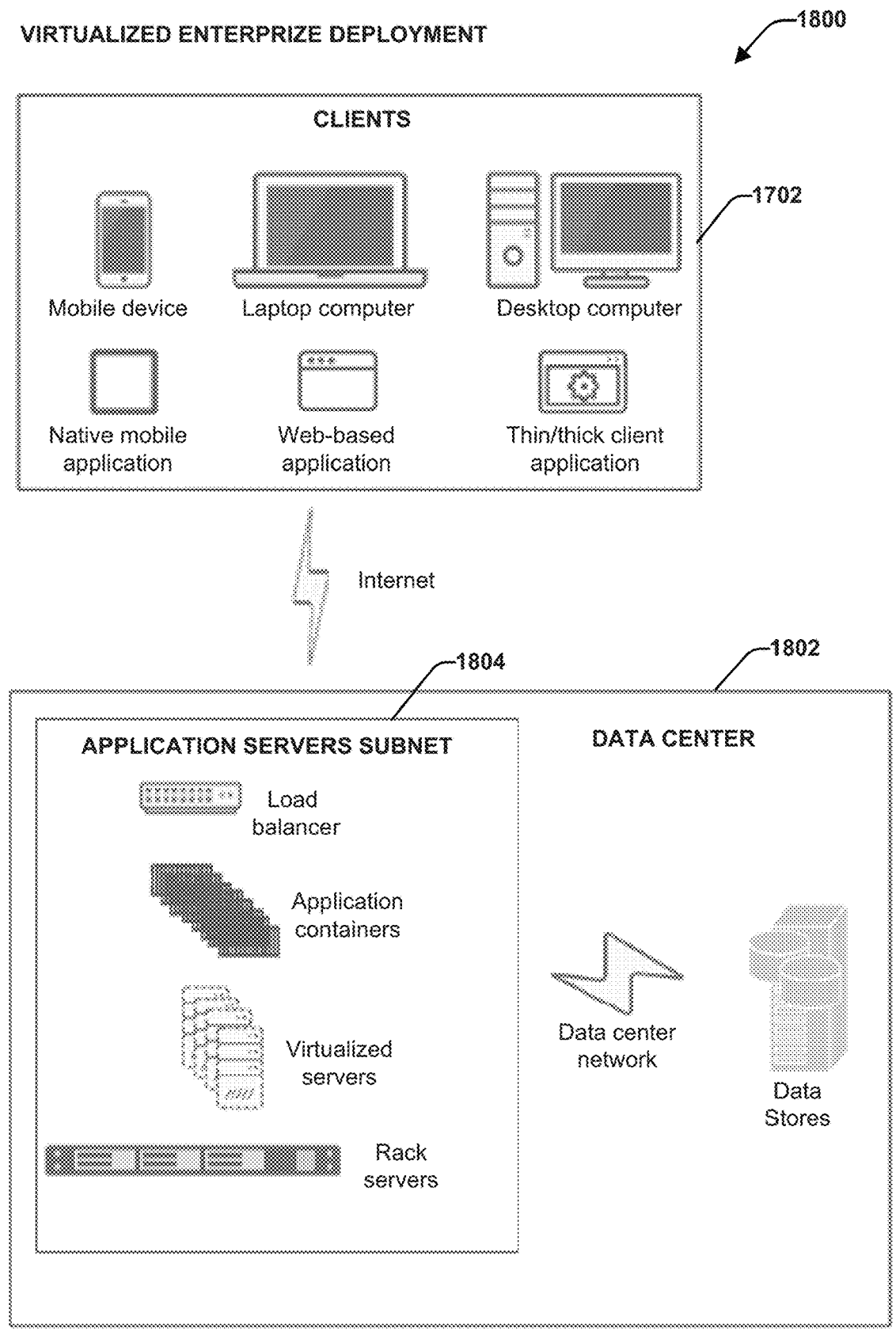
FIG. 18 illustrates a block diagram of another example, non-limiting operating environment in which one or more embodiments described herein can be facilitated.

FIG. 18 illustrates a schematic block diagram of another example computing environment 1800 in accordance with this disclosure in which the subject systems (e.g., systems 100, 500, 900 and the like), methods and computer readable media can be deployed. The computing environment 1800 includes a virtualized enterprise deployment consisting of one or more clients 1702 that can be communicatively coupled to a remote data center 1802 via a network (e.g., the Internet). The remote data center 1802 can include an application servers subnet 1804 which can provide a load balancer, one or more application containers, one or more virtualized servers and one or more rack servers. The data center 1802 can also include one or more data stores that can be communicatively coupled to the application servers subnet 1804 via a data center network. In accordance with the virtualized enterprise deployment, the clients 1702 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., system 100, 500, 900 and the like) deployed in the data center 1802 and application servers subnet 1804. In various implementations, the one or more components of systems 100, 500 and/or 900 can be distributed between the clients 1702 and the application servers subnet 1804 and the data center 1802.

Figure 19:
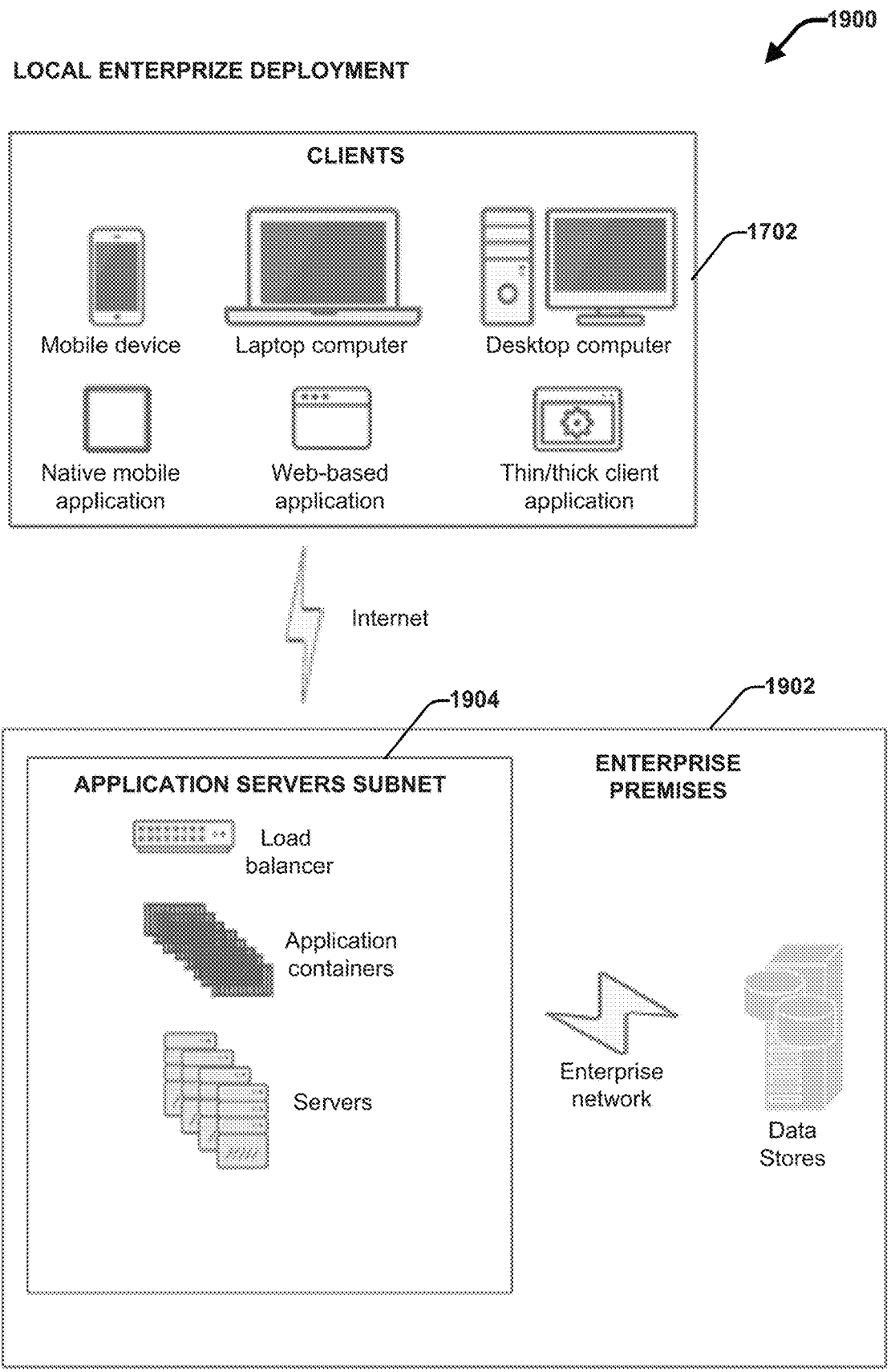
FIG. 19 illustrates a block diagram of another example, non-limiting operating environment in which one or more embodiments described herein can be facilitated.

FIG. 19 illustrates a schematic block diagram of another example computing environment 1900 in accordance with this disclosure in which the subject systems (e.g., systems 100, 500, 900 and the like), methods and computer readable media can be deployed. The computing environment 1900 includes a local enterprise deployment consisting of one or more clients 1702 that can be communicatively coupled to an application servers subnet 1904 via a network (e.g., the Internet). In accordance with this embodiment, the application servers subnet 1904 can be provided at the enterprise premises 1902 (e.g., as opposed to a remote data center 1902). The application servers subnet 1904 can include a load balancer, one or more application containers and one or more servers. The application servers subnet 1904 can be communicatively coupled to one or more data stores provided at the enterprise premises 1902 via an enterprise network. Similar to the cloud and virtualized enterprise deployments, the clients 1702 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., system 100, 500, 900 and the like) deployed at the enterprise premises 1902 and the application servers subnet 1904. In various implementations, the one or more components of systems 100, 500 and/or 900 can be distributed between the clients 1702 and the application servers subnet 1904 and the enterprise premises 1902.

Figure 20:
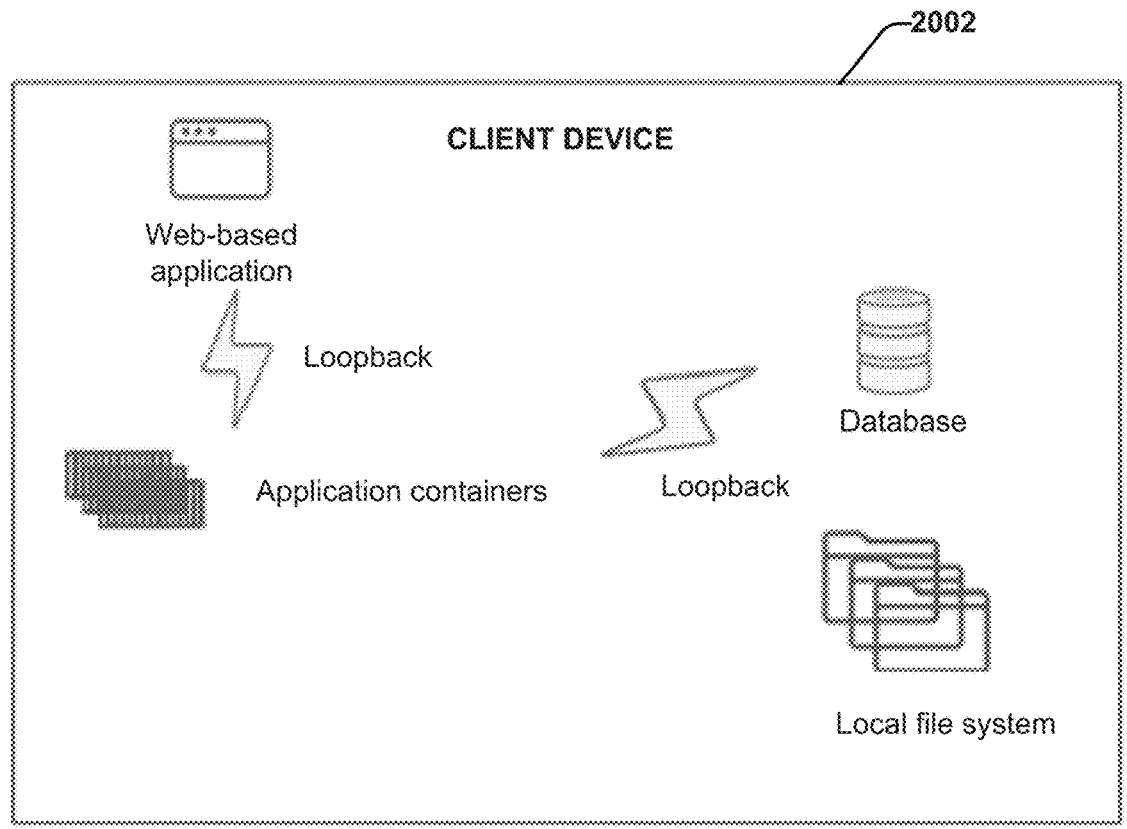
FIG. 20 illustrates a block diagram of another example, non-limiting operating environment in which one or more embodiments described herein can be facilitated.

FIG. 20 illustrates a schematic block diagram of another example computing environment 2000 in accordance with this disclosure in which the subject systems (e.g., systems 100, 500, 900 and the like), methods and computer readable media can be deployed. The computing environment 2000 includes a local device deployment in which all of the components of system 100, 500 and/or 900 are provided at a single client device 2002. With this implementation, the client device 2002 can include a web-based application which can be communicatively coupled via a loopback to one or more application containers. The one or more application containers can be communicatively coupled via a loopback to one or more databases and/or one or more local file systems.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
an interface component that facilitates accessing a medical imaging application that provides for viewing medical image data;
a training data generation component that facilitates generating structured training data according to a defined ontology in association with viewing the medical image data using the imaging application, wherein the structured training data comprises measurement data that defines a measurement for one or more features in the medical image data, and wherein the training data generation component comprises:
a measurement component that generates the measurement data based on a measurement marking applied to the one or more features in the medical image data as displayed via a graphical user interface; and
a data collection component that provides the structured training data to one or more machine learning systems, wherein based on reception of the structured training data, the one or more machine learning systems employ the structured training data as training data to generate or train one or more diagnostic models configured to provide artificial intelligence-based diagnostic evaluations of new medical image data.

2. The system of claim 1, wherein the structured training data further comprises structured markup data that identifies a location of a feature of interest relative to the medical image data, and wherein the training data generation component further comprises:
a markup component that facilitates applying a graphical marking on the feature of interest present in the medical image data as displayed via a graphical user interface and generates the structured markup data based on the graphical marking.

3. The system of claim 2, wherein the structured markup data comprises one or more medical images comprising the graphical marking and formatted according to the Digital Imaging and Communications in Medicine (DICOM) standard.

4. The system of claim 1, wherein the structured training data further comprises structured annotation data that identifies a feature of interest relative to the medical image data, and wherein the training data generation component further comprises:
an annotation component that facilitates applying an annotation to the feature of interest present in the medical image data as displayed via the graphical user interface and generates the structured annotation data based on the annotation, and wherein the annotation component restricts application of the annotation using terms or symbols that adhere to the defined ontology.

5. The system of claim 4, wherein the annotation component determines the one or more annotation terms in accordance with the defined ontology that are relevant to the medical image data and presents the one or more annotation terms via the graphical user interface for potential manual application to the feature of interest.

6. The system of claim 5, wherein the annotation component employs artificial intelligence and one or more classifiers to determine the one or more annotation terms.

7. The system of claim 5, wherein the annotation component restricts manual application of the annotations to the medical image data based on the one or more annotation terms.

8. The system of claim 1, wherein the measurement component further facilitates applying the measurement marking using one or more defined measurement marking tools of the graphical user interface.

9. The system of claim 1, wherein the measurement data comprises a dimension of the one or more features, and wherein the measurement component determines the dimension based on the measurement marking.

10. The system of claim 1, wherein the structured training data further comprises structured segmentation data that defines one or more distinct visual features extracted from the medical image data, and wherein the training data generation component further comprises:
a segmentation component that identifies the one or more distinct visual features in the medical image data, extracts the one or more distinct visual features from the medical image data, and generates structured segmentation data based on the one or more distinct visual features as extracted from the medical image data.

11. The system of claim 1, wherein the structured training data further comprises structured training data regarding a diagnostic interpretation of the medical image data, and wherein the training data generation component further comprises:
a reporting component that facilitates generating a textual diagnostic report regarding the diagnostic interpretation of the medical image data, wherein the reporting component further generates the structured training data based on the textual diagnostic report.

12. The system of claim 11, wherein the reporting component determines a subset of medical terms or information categories for potential inclusion in the textual diagnostic report based on the medical image data and the defined ontology and presents the subset of medical terms or information categories via the graphical user interface.

13. The system of claim 12, wherein the reporting component employs artificial intelligence and one or more classifiers to determine the subset of medical terms or information categories.

14. The system of claim 12, wherein the reporting component further restricts content for inclusion in the textual diagnostic report based on the subset of the medical terms or information categories.

15. The system of claim 11, wherein reporting component employs natural language processing to identify one or more semantically relevant terms or phrases included in the textual diagnostic report, and wherein the reporting component further generates the structured textual report data using the semantically relevant terms or phrases.

16. A method, comprising:
interfacing, by a system operatively coupled to a processor, with a medical imaging application that provides for viewing medical image data;
generating, by the system, structured training data according to a defined ontology in association with usage of the imaging application to perform a clinical evaluation of the medical image data, wherein the generating comprises:

generating, by the system measurement data that defines a measurement for one or more features in the medical image data based on a measurement marking applied to the one or more features in the medical image data as displayed via a graphical user interface; and providing, by the system, the structured training data to one or more machine learning systems, wherein based on the providing, the one or more machine learning systems employ the structured training data as training data to generate or train one or more diagnostic models configured to provide artificial intelligence-based diagnostic evaluations of new medical image data.

17. The method of claim 16, further comprising:
providing, by the system, a markup tool that facilitates applying a graphical marking on a feature of interest present in the medical image data as displayed via the graphical user interface, and wherein the generating the structured training data further comprises:
generating, by the system, structured markup data that identifies a location of the feature of interest relative to the medical image data based on the graphical marking.

18. The method of claim 16, further comprising:
providing, by the system, an annotation tool that facilitates applying an annotation to a feature of interest present in the medical image data as displayed via the graphical user interface, wherein the annotation tool restricts the annotation based on a defined set of terms in accordance with the defined ontology and wherein the generating the structured training data further comprises:
generating, by the system, structured annotation data based on the annotation, wherein the structured annotation data that identifies the feature of interest relative to the medical image data and associates the annotation with the feature.

19. The method of claim 18, further comprising:
determining, by the system, one or more terms included in the defined set of terms that are relevant to the medical image data; and
presenting, by the system, the one or more terms via the graphical user interface for potential application to the feature of interest.

20. A machine-readable storage medium, comprising executable instructions that, when executed by a processor, facilitate performance of operations, comprising:
interfacing with a medical imaging application that provides for viewing medical image data;
generating structured training data according to a defined ontology in association with usage of the imaging application to perform a clinical evaluation of the medical image data, wherein the generating comprises:
generating measurement data that defines a measurement for one or more features in the medical image data based on a measurement marking applied to the one or more features in the medical image data as displayed via a graphical user interface; and
providing the structured training data to one or more machine learning systems, wherein based on the providing, the one or more machine learning systems employ the structured training data as training data to generate or train one or more diagnostic models configured to provide artificial intelligence-based diagnostic evaluations of new medical image data.

* * * * *